US011061023B2

(12) United States Patent
Brousmiche et al.

(10) Patent No.: US 11,061,023 B2
(45) Date of Patent: Jul. 13, 2021

(54) FLUORESCENCE TAGGING OF GLYCANS AND OTHER BIOMOLECULES THROUGH REDUCTIVE AMINATION FOR ENHANCED MS SIGNALS

(71) Applicant: WATERS TECHNOLOGIES CORPORATION, Milford, MA (US)

(72) Inventors: Darryl W. Brousmiche, Grafton, MA (US); Matthew A. Lauber, North Smithfield, RI (US)

(73) Assignee: Waters Technologies Corporation, Milford, MA (US)

(*) Notice: Subject to any disclaimer, the term of this patent is extended or adjusted under 35 U.S.C. 154(b) by 138 days.

(21) Appl. No.: 16/312,826

(22) PCT Filed: Jun. 19, 2017

(86) PCT No.: PCT/US2017/038070
§ 371 (c)(1),
(2) Date: Dec. 21, 2018

(87) PCT Pub. No.: WO2017/222954
PCT Pub. Date: Dec. 28, 2017

(65) Prior Publication Data
US 2019/0331669 A1    Oct. 31, 2019

Related U.S. Application Data

(60) Provisional application No. 62/352,724, filed on Jun. 21, 2016.

(51) Int. Cl.
*G01N 33/533* (2006.01)
*C07D 215/48* (2006.01)

(52) U.S. Cl.
CPC ......... *G01N 33/533* (2013.01); *C07D 215/48* (2013.01)

(58) Field of Classification Search
None
See application file for complete search history.

(56) References Cited

U.S. PATENT DOCUMENTS

| | | | |
|---|---|---|---|
| 2,016,962 A | 10/1935 | Flint et al. |
| 4,003,912 A | 1/1977 | Franz |
| 4,068,528 A | 1/1978 | Gundelfinger |
| 4,138,398 A | 2/1979 | Richter et al. |
| 5,296,599 A | 3/1994 | Cohen et al. |
| 5,531,959 A | 7/1996 | Johnson et al. |
| 6,245,478 B1 | 6/2001 | Uetani et al. |
| 6,379,971 B1 | 4/2002 | Schneider et al. |
| 6,632,629 B2 | 10/2003 | Yang et al. |
| 6,716,634 B1 | 4/2004 | Myerson |
| 7,074,570 B2 | 7/2006 | Palmgren et al. |
| 7,148,069 B2 | 12/2006 | Miyano et al. |
| 7,186,739 B2 | 3/2007 | Guichard et al. |
| 7,494,815 B2 | 2/2009 | Shimbo et al. |
| 7,732,378 B2 | 6/2010 | Thompson et al. |
| 8,124,792 B2 | 2/2012 | Baginski |
| 8,198,063 B1 | 6/2012 | Baginski et al. |
| 8,445,292 B2 | 5/2013 | Baginski |
| 9,658,234 B2 | 5/2017 | Miyano et al. |
| 10,416,166 B2 | 9/2019 | Brousmiche et al. |
| 2001/0026929 A1 | 10/2001 | Yang et al. |
| 2004/0259262 A1 | 12/2004 | Ishii |
| 2005/0079624 A1 | 4/2005 | Miyano et al. |
| 2005/0158708 A1 | 7/2005 | Alroy et al. |
| 2005/0221337 A1 | 10/2005 | Seeberger et al. |
| 2006/0004220 A1 | 1/2006 | Hamprecht et al. |
| 2006/0035304 A1 | 2/2006 | Lebrilla et al. |
| 2006/0127950 A1 | 6/2006 | Bosques et al. |
| 2006/0286673 A1 | 12/2006 | Miyano et al. |
| 2007/0141723 A1 | 6/2007 | Sompuram et al. |
| 2007/0269895 A1 | 11/2007 | Aebersold et al. |
| 2008/0201095 A1 | 8/2008 | Yip et al. |
| 2008/0241856 A1 | 10/2008 | Wong et al. |
| 2008/0315084 A1 | 12/2008 | Yamada et al. |
| 2009/0050212 A1 | 2/2009 | Dourdeville et al. |
| 2009/0065687 A1 | 3/2009 | Gross et al. |
| 2009/0258437 A1 | 10/2009 | Baginski |
| 2010/0151499 A1 | 6/2010 | Collins et al. |
| 2010/0171055 A1 | 7/2010 | Dourdeville |
| 2011/0006237 A1 | 1/2011 | Tower |
| 2011/0171736 A1 | 7/2011 | Agnew et al. |
| 2012/0107942 A1 | 5/2012 | Baginski |
| 2012/0165370 A1 | 6/2012 | Tang et al. |
| 2013/0112604 A1 | 5/2013 | Keene et al. |
| 2013/0171658 A1 | 7/2013 | Fulton et al. |
| 2014/0030732 A1 | 1/2014 | Staples |

(Continued)

FOREIGN PATENT DOCUMENTS

| | | |
|---|---|---|
| CN | 1973047 A | 5/2007 |
| CN | 103918055 A | 7/2014 |

(Continued)

OTHER PUBLICATIONS

Heindel et al. J. Med. Chem. (1969) 12(5): 797-801 (Year: 1969).*
Registry File from STN for compound RN 1977407-60-5, entered on STN Aug. 22, 2016, downloaded Sep. 8, 2020 (Year: 2016).*
Registry File from STN for compound RN 1919202-16-6, entered on STN May 27, 2016, downloaded Sep. 8, 2020 (Year: 2016).*
Registry File from STN for compound RN 1970079-84-5, entered on STN Aug. 9, 2016, downloaded Sep. 8, 2020 (Year: 2016).*
Registry File from STN for compound RN 1975675-34-3, entered on STN Aug. 19, 2016, downloaded Sep. 8, 2020 (Year: 2016).*
Registry File from STN for compound RN 1915940-97-4, entered on STN May 23, 2016, downloaded Sep. 8, 2020 (Year: 2016).*

(Continued)

*Primary Examiner* — Susan M Hanley
(74) *Attorney, Agent, or Firm* — Kacvinsky Daisak Bluni PLLC

(57) ABSTRACT

Novel reagents comprising MS active, fluorescent compounds having an activated functionality for reaction with aldehydes and useful in labeling biomolecules such as glycans and methods of making the same are taught and described.

19 Claims, No Drawings

(56) References Cited

U.S. PATENT DOCUMENTS

| | | |
|---|---|---|
| 2014/0038215 A1 | 2/2014 | Smart et al. |
| 2014/0178912 A1 | 6/2014 | Liu et al. |
| 2014/0179011 A1 | 6/2014 | Brousmiche et al. |
| 2014/0200148 A1 | 7/2014 | Slade |
| 2014/0227793 A1 | 8/2014 | Gao et al. |
| 2014/0242709 A1 | 8/2014 | Brousmiche et al. |
| 2014/0274768 A1 | 9/2014 | Haab |
| 2014/0350263 A1 | 11/2014 | Brousmiche et al. |
| 2014/0370614 A1 | 12/2014 | Liu et al. |
| 2015/0057243 A1 | 2/2015 | Zhou et al. |
| 2015/0204824 A1 | 7/2015 | Lauber et al. |
| 2015/0346194 A1 | 12/2015 | Magnelli et al. |
| 2016/0018409 A1 | 1/2016 | Higel |
| 2016/0054274 A1 | 2/2016 | Cormier et al. |
| 2016/0069844 A1 | 3/2016 | Jackson et al. |
| 2016/0139136 A1 | 5/2016 | Brousmiche et al. |
| 2017/0370813 A1 | 12/2017 | Steen et al. |

FOREIGN PATENT DOCUMENTS

| | | |
|---|---|---|
| EP | 0671401 A1 | 9/1995 |
| EP | 2305692 A1 | 4/2011 |
| EP | 2990401 A1 | 3/2016 |
| JP | S59161355 A | 9/1984 |
| JP | S60186502 A | 9/1985 |
| JP | S62195361 A | 8/1987 |
| JP | H09101310 A | 4/1997 |
| JP | H10306075 A | 11/1998 |
| JP | H1180107 A | 3/1999 |
| JP | 2000510854 A | 8/2000 |
| JP | 2000329744 A | 11/2000 |
| JP | 2001526048 A | 12/2001 |
| JP | 2006038674 A | 2/2006 |
| JP | 2012512234 A | 5/2012 |
| JP | 2015091953 A | 5/2015 |
| WO | 9921580 A1 | 5/1999 |
| WO | 02074245 A2 | 9/2002 |
| WO | 2004027388 A2 | 4/2004 |
| WO | 2004086050 A2 | 10/2004 |
| WO | 2006114663 A1 | 11/2006 |
| WO | 2009070233 A1 | 6/2009 |
| WO | 2011038873 A1 | 4/2011 |
| WO | 2011146594 A2 | 11/2011 |
| WO | 2013081581 A1 | 6/2013 |
| WO | 2013084236 A1 | 6/2013 |
| WO | 2013151975 A1 | 10/2013 |
| WO | 2013192530 A2 | 12/2013 |
| WO | 2014085938 A1 | 6/2014 |
| WO | 2014194320 A1 | 12/2014 |
| WO | 2016009077 A1 | 1/2016 |
| WO | 2016069764 A1 | 5/2016 |
| WO | 2016089515 A1 | 6/2016 |

OTHER PUBLICATIONS

Extended European Search Report for EP Application No. 17815987. 7, dated Dec. 16, 2019, 8 pages.
Suzuki,et al, "Comparision of the Sensitivities of Various Derivatives of Oligosacchardies in LC/MS with Fast Atom Bombardment and Elecgtrospray Ionization Interfaces", Analytical Chemistry 68(13):2073-2083 (1996).
Cosgrave, E and McCarthy,. M Investigation of the Factors that Contribute to Glycan Separation in HI LIC, Businness Operations, Pharmaceutical Life Sciences, Waters Corporation (Year: 2014).
Bioengineering Analysis and Inspection, Wang Furong China Light Industry Press pub. Jun. 30, 2005.
CNOA for application 201580071764.2 dated Feb. 28, 2020 original and translated document, 18 pages.
Fu-Chuan, Li, et al., "Studies on Fluorescent Labeling of Marine Sulfated Polysaccharide 911", Chemical Journal of Chinese Universities, 23(9):1704-1708 (2002).
Zailin W., "Studies on Fluorescent Labeling of Several Fungal Polysaccharides", Chinese Master's Thesis, Agriculture Science and Technology, No. 5 (2013).
Takeda, K., et al., Convenient Methods for Syntheses of Active Carbamates, Ureas and Nitrosoureas Using N,N'- Disuccinimido Carbonate (DSC), Tetrahedron Letters 24(42):4569-72 (1983) Abstract.
Tarentino, A.L., et al., "2-Iminothiolane: A Reagent for the Introduction of Sylphydryl Groups into Oligosaccharides Derived from Asparagine-Linked Glycans", Glycobiology 3(3):279-285 (1993) Abstract.
Tousi "The Pursuit of Cancer Biomarkers: Liquid Chromatography and Mass Spectrometry 1-13 Platforms for Glycomic Characterization of Biospecimens" Northeastern University, Jul. 16, 2013.
Ullmer, R., et.al., "Derivatization by 6-aminoquinolyl-N-hydroxysuccinimidyl Carbamate for Enhancing the Ionization Yield of Small Peptides and Glycopeptides in Matrix-Assisted Laser Desorption/Ionization and Electrospray Ionization Mass Spectrometry", Rapid Communications in Mass Spectrometry pp. 1469-1479 (2006).
Van Wandelen, C., et al., "Using Quaternary High-Performance Liquid Chromatography Eluent Systems for Separating 6-Aminoquinolyl-N-Hydroxysuccinimidyl Carbamate-Derivatized Amino Acid Mixtures", Journal of Chromatography A, 763:11-22 (1997).
Vasilevich, N., et al., "Conversion of O-Succinimidyl Carbamates to N-(O-Carbamoyl)-Succinmonoamides and Ureas: Effects of N-Substituents and Reaction Conditions on the Reaction Pathway", Tetrahedron Letters 43:6649-6652 (2002) Abstract.
Voet, "Biochemistry" Second Edition, John Wiley & Sons, Inc. 1995, Chapters 4, 5. Abstract.
Vollhardt, "Organic Chemistry Structure and Function," Third Edition, W. H. Freeman and Company, 1999, Chapters 14, 20, 21, 26. Abstract.
Wada, Y., et al., "Comparison of the Methods for Profiling Glycoprotein Glycans—HUPO Human Disease Glycomics/Proteome Initiative Multi-Institutional Study", Glycobiology 17(4):411-422 (2007).
Walker et al., Hydrophobic Derivatization of N-linked Glycans for Increased Ion Abundance in Electrospray onization Mass Spectrometry, J Am Soc Mass Spectrom 2011; 22(8): 1309-17.
Waters Corporation "GlycoWorks High-Throughput Sample Preparation Kit" (Sep. 2013).
Watson, "Introduction to Mass Spectrometry" Raven Press, New York 1985, Chapters 1 and 4. Abstract.
Wei, W-J., et al., "Study on N-Hydroxyphthalimide as Blocking Agent for Isocyanates", Journal of Applied Polymer Science 84:1346-1352 (2002).
Wuhrer, M., et al., "Nano-Scale Liquid Chromatography-Mass Spectrometry of 2-Aminobenzamide-Labeled Oligosaccharides at Low Femtomole Sensitivity", International Journal of Mass Spectrometru 232:51-57 (2004).
Yates, "Peptide Mass Maps: A Highly Informative Approach to Protein Identification," Analytical Biochemistry 1993, 214: 397-408.
Yodoshi, M., et al: "Optimized conditions for high-perfonnance liquid chromatography analysis of oligosaccharides using 7-amino-4-methylcoumarin as a reductive amination reagent", Journal of Chromatography A Elsevier, Amsterdam, NL, vol. 1203, No. 2, pp. 137-145, Sep. 5, 2008.
Yost, "Triple Quadrupole Mass Spectrometry for Direct Mixture Analysis and Structure Elucidation," Analytical Chemistry 1979, 51(12):1251A-1264A Abstract.
Yu Y. Q., "N-linked Glycan Characterization and Profiling: Combining the Power of Accurate Mass, Reference Glucose Units, and UNIFI Software for Confident Glycan Assignments," Waters, Application Note (2013) 10 pages.
Yu Y.Q., et al., "A Rapid Sample Preparation Method for Mass Spectrometric Characterization of N-linked Glycans", Rapid Communications in Mass Spectrometry 19:2331-2336 (2005).
Zhang Li et al., "Practical Guidance of Detection by Separation", Press of University of Science and Technology of China, Jan. 2013, p. 55.
Chapter 2—Norepinephrine (NPL cited during examination procedure) Jul. 16, 2020.
Yang et al., "Solid-phase glycan isolation for glycomics analysis", Proteomics Clin Appl. Dec. 2012; 6(0): 596-608. doi:10.1002/prca. 201200045 (Year 2012).

(56) References Cited

OTHER PUBLICATIONS

Johannesen et al. "Glycan analysis via derivatization with a fluorogenic pyrylium dye", Carbohydrate Research, 352:94-100 (2012) Abstract.
Extended European Search Report for Application No. EP20188814. 6, dated Oct. 2, 2020, 7 pages.
Ahn J., et al., "Separation of 2-aminobenzamide labeled glycans using hydrophilic interaction chromatography columns packed with 1.7 μm sorbent," Journal of Chromatography B, 878: 403-8 (2010).
Anumula et al., "High Resolution and High Sensitivity Methods for Oligosaccharide Mapping and Characterization by Normal Phase High Performance Liquid Chromatography Following Derivitization with Highly Flourescent Anthranilic Acid", Glycobiology 8(7):685-694 (1998).
Author unknown, Best Practices in the Analysis of Rapifluor-MS Labeled Glycans Using the Acquity QDa Detector 5 Performance Model), Waters [online] Mar. 2016 While Paper [retrieved on Apr. 1, 2020]. Retrieved from the Internet URL: https://www.gimitec.com/file/720005655en.pdf, 19 pages.
Bartlet-Jones, "Peptide ladder sequencing by mass spectrometry using a novel, volatile degradation reagent," Rapid Commun. Mass Spectrom. 1994, 8, 737-742. Abstract.
Bereman et al., Increasing the hydrophobicity and electrospray response of glycans through derivatization with novel cationic hydrazides, Chem Commun (Camb) 2010; 26 (2): 237-9.
Black, S.D., et al., "Simple, Rapid, and Highly Efficient Separation of Amino Acid Phenylthiohydantoins by Reversed-Phase High-Performance Liquid Chromatography", Analytical Biochemstry 121:281-285 (1982).
Block et al., "2050P: HPLC/MS Analysis of Amino Acids: The Use of 6-Aminoquinolyl-N-Hydroxy-Succinimidyl Carbamate Derivatives", Poster presented at Pittsburgh Conference, Mar. 1999.
Block, E., et al., "2050P: HPLC-MS Analysis of Amino Acids", Abstract presented at Pittsburgh Conference, Mar. 1999.
Block, E.H., "LC/MS Application Notes: The Use of 6-Aminoquinolyl N Hydroxy Succinimidyl Carbamate Derivatives for HPLC/MS Analysis of Amino Acids", Presentation at Pittsburgh Conference, Mar. 1999.
Block, E.H., "The Use of 6-Aminoquinolyl-N-Hydroxy Succinimidyl Carbamate Derivatives for HPLC/MS Analysis of 4mino Acids", AMD35 Waters Alliance LC/MS System 2000.
Brancia, "Improved matrix-assisted laser desorption/ionization mass spectrometric analysis of tryptic hydrosylates of proteins following guanidation of lysine-containing peptides," Rapid Commun. Mass Spectrom. 14, 2070-2073 (2000) Abstract.
Briggs, J.B. et al., "An analytical system for the characterization of highly heterogeneous mixtures of N-linked oligosaccharides", Analytical Biochemistry, 389:40-51 (2009).
Brophy, "Electron Impact and chemical ionization mass spectra of aryl ureas," Organic Mass Spectrometry, vol. 14, No. 7, 1979, 379-386 Abstract.
Buku, "2,3-trans-3,4-trans-3,4-Dihydroxy-L-proline: An Amino Acid in Toxic Peptides of *Amanita virosa* Mushrooms," Proc. Natl. Acad. Sci. USA, 1980, 77(5): 2370-2371.
Busto, "Solid phase extraction of biogenic amines from wine before chromatographic analysis of their AQC derivatives," J. Liq. Chrom. & Rel. Technol. 1997, 20(5), 743-755 Abstract.
Byrnes, "6-Aminoquinoline as a Fluorogenic Leaving Group in Peptide Reactions: A New Fluorogenic Substrate for Chymotrypsin," Anal. Biochem. 116, 408-413 (1981) Abstract.
Campbell M. P., et al., "GlycoBase and autoGU: tools for HPLC-based glycan analysis," Bioinformatics, 24 (9): 1214-1216, (2008).
Casoli, A., et al., "Use of High-Performance Liquid Chromatography for the Determination of Amino Acids in Sparkling Wines", Am J Enol Vitic 33(3):135-139 (1982).
Cech and Enke, "Relating Electrospray Ionization Response to Nonpolar Character of Small Peptides," Anal. Chem. 2000, 72:2717-2723. Abstract.
Chalmers, "Advances in Mass Spectrometry for Proteome Analysis," Current Opinion in Biotechnology 2000, 11: 384-390. Abstract.

Bunz, S-C., et al., "Analysis of native and APTS-labeled N-glycans by capillary electrophoresis/time—0f-flight mass spectrometry", Analytical and Bioanalytical Chemistry 405:8277-8284 (2013).
Knezevic, A., et al., "High throughput plasma N-glycome profiling using multiplexed labelling and UPLC with fluorescence detection", Analyst, 136:4670-4673 (2011).
Lauber, M.A. et al., "Rapid Preparation of Released N-Glycans for HILIC Analysis Using a Labeling Reagent that Facilitiates Sensitive Fluorescence and ESI-MS Detection", Analytical Chemistry 87:5401-5409 (2015).
Schwartz, B., et al., "A Kinetic Characterization of the Glycosyltransferase Activity of *Eschericia coli* PBP1b and Development of a Continuous Fluorescence Assay", Biochemistry, 41: 12552-12561 (2002).
Song, X., et al., "Glycan microarrays off fluorescently-tagged natural glycans", Glycoconjugate Journal, 32:465-473 (2015).
West, C., et al., "Porous Graphitic Carbon: a Versatile Stationary Phase for Liquid Chromatography", J Chromatogr A 1217(19):3201-16 (2010).
CNOA for Patent Application No. 201780053453.2 dated Feb. 4, 2021, original and translated document 24 pages.
Zhang, Y., ed., Biological Sample Library Establishment and Practice, p. 102 Sun Yat-Sen University Press (Oct. 2013).
Huang, R., ed., Analytical Chemistry, National Defense Science and Technology University Press pp. 146-150 (Mar. 2014).
Cline et al., "The Aminolysis of N-Hydroxysuccinimide Esters. A Structure-Reactivity Study", J Am Chem Soc 109 (10):3087-3091 (1987).
Cohen, "Clearing the Hurdle of High Sensitivity in Biopharmaceutical Research," LC GC North America 1999, 17(4S): S9-S16.
Cohen, S. A., et al.,"Compositional Protein Analysis Using 6-Aminoquinolyl-N-Hydroxysuccinimidyl Carbamate, a Novel Derivatization Reagent", Techniques in Protein Chemistry IV pp. 289-298 (1993).
Cohen, S. A., et al., "Synthesis of a Fluorescent Derivatizing Reagent, 6-Aminoquinolyl-N-Hydroxysuccinimidyl Carbamate, and Its Application for the Analysis of Hydrolysate Amino Acids via High-Performance Liquid Chromatography", Analytical Biochemistry 211:279-87 (1993).
Communication of a notice of opposition for EP Patent No. 2761296 dated Jun. 5, 2018.
Communication pursuant to Article 94(3) EPC for Application No. EP17188121.2, dated Sep. 14, 2020, 3 pages.
Communication pursuant to Article 94(3) EPC, dated Apr. 17, 2019, for Application No. EP15855907.0, 4 pages.
Cook et al., Development and Qualification of an Antibody Rapid Deglycosylation Method, Biologicals 2012; 40 (2):109-17.
European Search Report and Written Opinion dated Feb. 2, 2016 regarding patent application No. EP 15180680.9, 7 pages.
Cooper, D., et al., "LC-MS/MS Analysis of AccQ-Tag Derivatised Amino Acids", Micromass UK Limited pp. 1-7 (2000).
Cooper, D., et al., "LC-MS/MS Analysis of AccQ-Tag Derivatised Amino Acids, Micromass Application Brief", Sep. 2000 and Jun. 2000.
Cooper, D. et al., "LC-MS-MS Analysis of Amino Acids Using AccQ-Tag derivatisation, Application Brief AB25", Micromass Jun. and Sep. 2000.
Covey, "Liquid Chromatography/Mass Spectrometry," Analytical Chemistry 1986, 58(14):1451A-1461A. Abstract.
Darren L. Holmes, Eric M. Smith, and James S. Nowick "Solid-Phase Synthesis of Artificial beta-Sheets" Journal of American Chemical Society 119: 665-7669 (1997).
De Antonis, K. M., et al., "High-Performance Liquid Chromatographic Analysis of Synthetic Peptides Using Derivatization with 6-Aminoquinolyl-N-Hydroxysuccinimidyl Carbamate", Analytical Biochemistry 223:191-197 (1994).
De Hoffmann, "Mass Spectrometry, Principles and Applications," Second Edition, John Wiley Sons Ltd. 2001, Introduction, Chapters 1, 3, and 7. Abstract.
De Hoffmann, "Tandem Mass Spectrometry: a Primer," J. Mass Spec. 1996, 31, 129-137. Abstract.

(56) References Cited

OTHER PUBLICATIONS

Dell, "Fast Atom Bombardment Mass Spectrometric Strategies for Characterizing Carbohydrate-containing Biopolymers," Biomedical and Environmental Mass Spectrometry, 1988, 16, 19-24. Abstract.
Dextran Calibration Ladder Standard. Waters (2012), 3 pages.
Dextran Calibration Ladder. Waters. Product Solution (2013) 3 pages.
European Search Report for Application No. 15855907.0, dated Jul. 6, 2018 , 12 pages.
EP Communication pursuant to Article 94(3) EPC, EP Application No. 12836127.6, dated Sep. 26, 2016.
EP Communication under Rule 71(3) EPC, EP Application No. 12836127.6, dated Mar. 15, 2017.
EP Communication with extended search report, EP Application No. 15180680.9, dated Feb. 2, 2016.
European Search Report and Written Opinion dated Aug. 26, 2014 regarding patent application No. EP12836127.6, 6 pages.
Expert Declaration by Prof. Ulf Diederichsen dated Jul. 23, 2019, 7 pp.
Extended European Search Report and Written Opinion for EP Application No. 15855907.0 dated Mar. 19, 2018, 10 pages.
Extended European Search Report for Application No. EP17820918. 5, dated Jan. 28, 2020, 7 pages.
Extended European Search Report, EP 12836127.6, dated Aug. 26, 2014.
Fekkes, "State-Of-The-Art of High-Performance Liquid Chromatographic Analysis of Amino Acids in Physiological Samples," Journal of Chromatography B. 1996, 682(1):3-22.
Field, B., et al, Chromatography Forum: LC-MS & GC-MS Archives: AAA LC-MS [online] 2003 [retrieved on Jan. 30, 2003]. Retrieved from Internet URL http://www. lcresources. com/d iscus/messages/ 5135/3143. html, 6 pages.
GlykoPrep™ Instant AB now fully commercialized. http://www. europa-bioproducts.com/latest.aspx?id=14 {accessed Sep. 8, 2014).
Gong et al., N-Glycosylamine-Mediated Isotope Labeling for Mass Spectrometry-Based Quantitative Analysis of Ncinked Glycans. Anal Bioanal Chem 2013; 405: 5825-31.
Guichard, G., et al., "Preparation of O-Succinimidyl-2-(tert-Butoxycarbonylamino)ethylcarbamate Derivatives from Beta-Amino Acids. Application to the Synthesis of Urea-Containing Pseudopeptides and Oligoureas", Journal of Org Chem 64:8702-8705 (1999).
Guile G. R. et al. "A Rapid High-Resolution High-Performance Liquid Chromatographic Method for Separating Glycan Mixtures and Analyzing Oligosaccharide Profiles," Analytical Biochemistry, 240: 210-226, (1996).
H. R. Liang, et al., "Quantitative determination of endogenous sorbitol and fructose in human nerve tissues by atmospheric-pressure chemical ionization liquid chromatography tandem mass spectrometry", Rapid Communications in Mass Spectrometry, 19(16):2284-2294, Aug. 30, 2005. Abstract.
Harvey et al., Electrospray Mass Spectrometry and Fragmentation of N-Linked Carbohydrates Derivatized at the Reducing Terminus, J Am Soc Mass Spectrom 2000, 11 (10), 900-15.
Harvey et al., Proposal for a standard system for drawing structural diagrams of N- and O-linked carbohydrates and related compounds, Proteomics 2009; 9 (15): 3796-801.
Harvey, D., "Identification of protein-bound carbohydrates by mass spectrometry" Proteomics 1:311-328 (2001).
Heinze-Krauss, I., et al., "Structure-Based Design of B-Lactamase Inhibitors. 1. Synthesis and Evaluation of Bridged Monobactams" , Journal of Med Chem 41:3961-3971 (1998) Abstract.
Hermanson, "Bioconjugate Techniques," 1996, Chapter 8. Abstract.
Higashi, T., et al., "Derivatization of Neutral Steroids to Enhance Their Detection Characteristics in Liquid Chromatography-Mass Spectrometry", Anal Bioanal Chem 378:875-882 (2004).
Higuchi, K., et al., "Chemistry of Succinimido Esters. IV*1. A Facile Preparation of N-Succinimidyl Carboxylates Using N, N'-Disuccinimidyl Carbonate", Oil Chemistry, 36(1)16-20 (1987).

Hirai, "Development of a new fluorescence labeling reagent succinimido-2-fluorenylcarbamate for highly sensitive detection of N-solanesyl-N,N-bis(3,4-dimethoxybenzyl) ethanediamine by HPLC," Anal. Chem. 1991, 40(5), 233-238. Abstract.
Hochleitner, E.O., et al., "Determination of the Stoichiometry of Protein Complexes Using Liquid Chromatography with Fluorescence and Mass Spectrometric Detection of Fluorescently Labeled Proteolytic Peptides", Proteomics 4:669-676 (2004).
Hossler et al., "Optimal and Consistent Protein Glycosylation in Mammalian Cell Culture", Glycobiology 19(9):936-949 (2009).
HP Primer Hewlett Packard, Basics of LC/MS: A Primer. 1998.
International Preliminary Report on Patentability, PCT/US2012/ 057996, dated Apr. 1, 2014.
International Search Report and Written Opinion for International App. No. PCT/US15/57848, dated Feb. 5, 2016, 5 pages.
International Search Report and Written Opinion for International Application No. PCT/US2017/038070, dated Sep. 29, 2017, 10 pages.
Kurita, K, et al., "Synthesis and Properties of Polyurethanes Derived from bis-N-Hydroxyimides and Diisocyanates", Journal of Polymer Science 17:1619-1629 (1979).
Lauber et al., Optimization of GlycoWorks HILIC SPE for the Quantitative and Robust Recovery of N-Linked Glycans from mAb-Type Samples. Waters Application Note. (2013).
Chezal, J-M., et al. "Evaluation of Radiolabeled (Hetero)Aromatic Analogues of N-(2-diethylaminoethyl)-4-iodobenzamide for Imaging and Targeted Radionuclide Therapy of Melanoma" J. Med. Chem. 51:3133-3144 (2008).
Lawrence, "Derivatization in Chromatography Introduction, Practical Aspects of Chemical Derivatization in Chromatography," Journal of Chromatographic Science 1979, 17:113-114. Abstract.
Li De et al.,"Techniques of Biomolecule Scientific Experiments", Hunan Science and Technology Press, Nov. 2001, the 1st edition, p. 32-33.
Liu et al., Investigation of Sample Preparation Artifacts Formed during the Enzymatic Release of N-Linked Glycans prior to Analysis by Capillary Electrophoresis. Anal. Chem. 2009; 81: 6823-6829.
Liu, H., et al., "Determination of Submicromolar Concentrations of Neurotransmitter Amino Acids by Fluorescence Detection Using a Modification of the 6-Aminoquinolyl-N-Hydroxysuccinimidyl Carbamate Method for Amino Acid Analysis", Journal of Chromatograpjy A, 828:383-395 (1998).
Liu, H. et al., "Femtomole Peptide Mapping by Derivatization, High-Performance Liquid Chromatography, and Fluorescence Detection", Analytical Biochemistry 294:7-18 (2001).
Liu, Hongji, et.al.; "Homogeneous Fluorescent Derivatization of Large Proteins", Journal of Chromatography A, 927: 77-89 (2001).
Louris, "New Scan Modes Accessed with a Hybrid Mass Spectrometer," Anal. Chem. 1985, 57, 2916-2924. Abstract.
Ma, "Determination of Midazolam and its Metabolites in Serum Microsamples by High-Performance Liquid Chromatography and its Application to Pharmacokineics in Rats," J Chromatography B Biomed Appl. 1996, 682 (1):109-113. Abstract.
Marino et al., "A Systematic Approach to Protein Glycosylation Analysis: A Path Through the Maze", Nature Chemical Biology 6:713-723 (2010).
Martinez-Force, E., et al., "Separation of O-Phthalaldehyde Derivatives of Amino Acids of the Internal Pool of Yeast by Reverse-Phase Liquid Chromatography", Biotechnology Technique 5(3):209-214 (1991).
Mazzocchi, Paul et al., "A Photochemical Route to Pyrrolo[1,4]Benzodiazepine Antitumor Antibiotics" Heterocycles 23 (7):1603-1606 (1985).
McLafferty, "Interpretation of Mass Spectra," Fourth Edition, University Science Books, Sausalito, CA 1993, Chapter 1. Abstract.
Mechref et al., Quantitative Glycomics Strategies, Mol Cell Proteomics 2013, 12 (4) 874-84.
Morpugo, "N-hydroxysuccinimide carbonates and carbamates are useful reactive reagents for coupling ligands to lysines on proteins," J. Biochem. Biophys.Methods 38 (1999), 17-28.
Nakashima, "Study on ππ Interaction in High Performance Liquid Chromatography," J. Liq. Chrom. Rel. Technol. 2000, 23(16), 2533-2540 Abstract.

(56) References Cited

OTHER PUBLICATIONS

Nimura, "Detection reagents used for high performance liquid chromatography," Pharmacia (1981) 17(8):707-709.
Nimura N. et al., "Activated Carbamate Reagent as Derivatizing Agent for Amino Compounds in High-Performance Liquid Chromatography", Analytical Chemistry 58:2372-2375 (1986).
Okamoto, "Sensitive Detection and Structural Characterization of Trimethyl(p-aminophenyl)-ammonium-derivatized Oligosaccharides by Electrospray Ionization-Mass Spectrometry and Tandem Mass Spectrometry," Rapid Communications in Mass Spectrometry, 1995, 9, 641-643. Abstract.
Pall Life Sciences "AcroPrep Advance Filter Plates" Pall Corporation (Mar. 2013) p. 7, col. 2, 10 Table AcroPrep Advance 96-Well Filter Plates for Ultrafiltration.
Park, S., et al., "Regioselective Covalent Modification of Hemoglobin in Search of Antisickling Agents", J Med Chem 46:936-953 (2003) Abstract.
Paschinger, K., et al., "Analysis of zwillerionic and anionic N-linked glycans from invertebrates and protisls by mass spectrometry", Glycoconjugate Journal, 33(3):273-283 (2016).
Pettersson et al., Chemical Stability of Reversed Phase High Performance Liquid Chromatography Silica under Sodium Hydroxide Regeneration Conditions, J Chromatogr A 2007; 1142 (1 ): 93-7.
Piepponen, T.P., et al., "Rapid and Sensitive Step Gradient Assays of Glutamate, Glycine, Taurine and y-Aminobutyric Acid by High-Performance Liquid Chromatography-Fluorescence Detection with o-Phthalaldehyde-Mercaptoethanol Derivatization With an Emphasis on Microdialysis Samples", Journal of Chromatography B, 757:277-283 (2001).
Pubchem CID: 43450869 Create Date: Jul. 21, 2009.
Qu, Y., et al., "Structural analysis of N- and O-glycans using ZIC-HILIC/Dialysis coupled to NMR detection", Fungal Genetics and Biology, 72:207-215 (2014).
Quirke, "Chemical Derivatization for Electrospray Ionization Mass Spectrometry. 1. Alkyl Halides, Alcohols, Phenols, Thiols, and Amines," Anal Chem. 1994, 66, 1302-1315. Abstract.
Rasmussen, "The nomenclature of fused-ring arenes and heterocycles: a guide to an increasingly important dialect of organic chemistry," ChemTexts, 2016, 2(16), 1-13.
Reubsaet, "Characterisation of ππinteractions which determine retention of aromatic compounds in reversed-phase liquid chromatography," Journal of Chromatography A, 1999, 841, 147-154. Abstract.
Roth, "Charge Derivatization of Peptides for Analysis by Mass Spectrometry," Mass Spectrometry Reviews 1998, 17:255-274 Abstract.
Rudd, "Rapid, sensitive sequencing of oligosaccharides from glycoproteins," Current Opinion in Biotechnology 1997, 8:488-497.
Ruhaak et al. Glycan Labeling Strategies and their use in Identification and Qualification, Anal Bioanal Chem 2010, 397 (8), 3457-81.
Saurina, J., et al., "Chromatographic Determination of Amino Acids by Pre-Column Derivatization Using 1,2-Napthoquinone-4-Sulfonate As Reagent", Journal of Chromatography A, 740:21-30 (1996).
Schmeer, K., et al., "Compositional Analysis of the Phenylthiocarbamyl Amino Acids by Liquid Chromatography-36 Atmospheric Pressure Ionization Mass Spectrometry with Particular Attention to the Cyst(e)ine Derivatives", Journal of Chromatography A,691285-299 (1995).
Schmidt, C.J., et al., "Amino Acid Profiling of Protein Hydrolysates Using Liquid Chromatography and Fluorescence Detection", Journal of Liquid Chromatography 2(7):1031-1045 (1979).
Schwartz, "Multistage mass spectrometry: Scan modes and new instrumentation" Dissertation 1989.
Schwartz, "Systematic Delineation of Scan Modes in Multidimensional Mass Spectrometry," Anal. Chem. 1990, 62:1809-1818 Abstract.
Search Report for GB1509402.2 dated Mar. 1, 2016.
Shimbo, "Multifunctional and Highly Sensitive Precolumn Reagents for Amino Acids in Liquid Chromatography/Tandem Mass Spectrometry," Anal. Chem. 2009, 81, 5172-5179. Abstract.
Snyder, "Introduction to Modern Liquid Chromatography," Second Edition, John Wiley & Sons, Inc. 1979, Introduction, Chapters 2, 4, 13, 14, 17. Abstract.
Synder, "Practical HPLC Method Development," Second Edition, John Wiley & Sons, Inc. 1997, Chapters 3, 4. Abstract.
Spengler, "Peptide sequencing of charged derivatives by postsource decay MALDI mass spectrometry," Int. J. Mass Spectrom. Ion Processes 1997, 169/170, 127-140. Abstract.
Statement of grounds appeal for European patent application No. 15180680.9, dated May 20, 2020, 4 pages.
Stockmann, "Ultrahigh Throughput, Ultrafiltration-Based NGlycomics Platform for Ultraperformance Liquid Chromatography (ULTRA3)," Anal. Chem. 2015, 87, 8316-8322. Abstract.
Struwe et al. 'Aminoquinolines as fluorescent labels for hydrophilic interaction liquid chromatography of oligosaccharides', Biological Chemistry, 2012, vol. 393, pp. 757-765.
Summons to attend oral proceedings pursuant to Rule 115(1) EPC for Application No. EP15180680.9, dated Jul. 18, 2019, 4 pages.
Summons to attend oral proceedings pursuant to Rule 115(1) EPC for Application No. EP15180680.9, dated Jun. 17, 2019, 9 pages.
Supplementary European Search Report, EP12836127.6 dated Sep. 12, 2014 and Response dated Mar. 19, 2015.
Ciucanu et al., A Simple and Rapid Method for the Permethylation of Carbohyrates, Carbohydr. Res. 1984, 131, 209-217.
International Search Report and Written Opinion for International Application No. PCT/US2017/038072, dated Oct. 3, 2017, 9 pages.
International Search Report and Written Opinion for PCT/GB2016/051605 dated Sep. 15, 2016.
International Search Report and Written Opinion for International Application No. PCT/US2017/014790, dated Apr. 27, 2017.
International Search Report and Written Opinion for International application No. PCT/US15/60326, dated Feb. 2, 2016, 6 pages.
International Search Report and Written Opinion for International application No. PCT/US2012/057996 dated Jan. 31, 2013.
Isbell, H.S. et al., "Effect of pH in the Mutarotation and Hydrolysis of Glycosylamines", JAGS letter to editor, 72:1043-1044 (1950).
Iwaki, "Activated carbamate reagent chiral derivatizing agent for liquid chromatographic optical resolution of enantiomeric amino compounds," Chromatographia 1987, 23(12), 899-902 Abstract.
Iwaki, "Amino acid analysis by reversed-phase high-performance liquid chromatography automatic pre-column derivatization with activated carbamate reagent," Journal of Chromatography, 407 (1987) 273-279 Abstract.
Jupille, "UV-Visible Absorption Derivatization in Liquid Chromatography," Journal of Chromatographic Science 1979, 17:160-167. Abstract.
Keough, "Atmospheric Pressure Matrix-Assisted Laser Desorption/Ionization Ion Trap Mass Spectrometry of Sulfonic Acid Derivatized Tryptic Peptides," Rapid Communications in Mass Spectrometry 2001, 15: 2227-2239. Abstract.
Kimzey, Michael et al., "Development of an Instant Glycan Labeling Dye for High Throughput Analysis by Mass Spectrometry", Prozyme Advancing Glycosciences, May 13, 2015, 4 pages.
Kinzel, O., et al., "Identification of MK-5710 ((8aS)-8a-methyl-1,3-dioxo-2-((1S,2R)-2-phenylcyclopropyl]-N-(1-phenyl-1H-pyrazol-5-yl)hexahydro-imidazo [1,5-a]pyrazine-7(1 H)-carboxamide), a potent smoothened antagonist for use in Hedgehog pathway dependent malignancies, Part 2", Bioorganic & Medicinal Chemistry Letters 21:4429-4435 (2011).
Klapoetke, S, et al., "The Evaluation of a Novel Approach for the Profiling and Identification of N-linked Glycans With a Procainamide Tag by HPLC With Fluorescent and Mass Spectrometric Detection", Journal of Pharmaceutical and Biomedical Analysis 53(3):315-324 (2010).
Kuster, B., et al: "Structural Determination of N-linked carbohyrdrates by matrix-assisted laser desorption/ionization-mass spectrometry following enzymatic release within sodium dodecyl sulphate-polyacrylamide electrophoresis gels: application to species-specific glycosylat", Electrophoresis: Liquid Phase Separation Techniques: Microfulidics, Naoanalysis, Proteomics, Wiley Interscience, DE, vol. 19, No. 11, pp. 1950-1959, Aug. 1, 1990.
EP12836127.6 Opposition Communication dated Jul. 23, 2019. 10 pages.

(56) References Cited

OTHER PUBLICATIONS

Communication pursuant to Article 94(3) EPC in European Patent Application No. 17815987. 7, dated Dec. 4, 2020, 5 pages.
Amendment and Response filed in U.S. Appl. No. 12/365,880, filed Feb. 4, 2009, dated Sep. 9, 2011, 17 pages.
Communication pursuant to Article 94(3) EPC, for Application No. EP17820918.5, dated Nov. 26, 2020, 5 pages.
Neville, D.C.A., et al., "Development of a Single Column Method for the Separation of Lipid- and Protein-Derived Oligosaccharides", Journal of Proteome Research, 8(2):681-687 (2009).
Decision on Rejection, Chinese Application No. 201280047599.3, dated Dec. 5, 2016, Original and translated.
Extended European Search Report for Application No. 17767589.9, dated Jan. 30, 2020, 11 pages.
Non-Final Office Action, U.S. Appl. No. 14/193,418, dated Nov. 15, 2016.
Non-Final Office Action, U.S. Appl. No. 14/342,131, dated Nov. 4, 2016.
Notice of Rejection, JP Application No. 2014-533416, dated Jan. 10, 2017. Original and Translated.
Office Action, U.S. Appl. No. 14/458,760, dated Apr. 12, 2017.
Response to EP Communication with extended search report, EP Application No. 15180680.9, dated Sep. 2, 2016.
Response to Non-Final Office Action, U.S. Appl. No. 14,342,131 dated Feb. 6, 2017.
Response to Non-Final Office Action, U.S. Appl. No. 14/193,418, dated Feb. 15, 2017.
Response to notice of opposition for EP Patent No. 2761296 filed Oct. 19, 2018.
Response to Office Action, U.S. Appl. No. 14/458,760, dated Jun. 12, 2017.
Response to Restriction Requirement, U.S. Appl. No. 14/342,131 dated Sep. 28, 2016.
Restriction Requirement, U.S. Appl. No. 14/342,131, dated Aug. 17, 2016.
Saurina, J., et al., "Determination of Amino Acids by Ion-Pair Liquid Chromatography With Post-Column Derivatization Using 1,2-Naphthoquinone-4-Sulfonate", Journal of Chromatography A,676:311-319 (1994).
Notice for Reasons for Rejection, dated Jul. 23, 2012, in Japanese Application No. 2009-269796 OD and Trans.

\* cited by examiner

FLUORESCENCE TAGGING OF GLYCANS AND OTHER BIOMOLECULES THROUGH REDUCTIVE AMINATION FOR ENHANCED MS SIGNALS

CROSS-REFERENCE TO RELATED APPLICATIONS

This application is a national phase filing claiming the benefit of and priority to International Patent Application No. PCT/US2017/038070, filed on Jun. 19, 2017, which claims priority to U.S. Provisional Patent Application No. 62/352,724 filed Jun. 21, 2016, incorporated herein by reference.

STATEMENT REGARDING FEDERALLY SPONSORED RESEARCH OR DEVELOPMENT

None.

THE NAMES OF PARTIES TO A JOINT RESEARCH AGREEMENT

None.

BACKGROUND OF THE INVENTION

Analysis of glycans is used for protein research and can be important to clinical chemists and pharmaceutical manufacturers, especially where glycosylation profiling of proteins is monitored to ensure consistency of a therapeutic product. As such, fluorescent labeling of glycans is beneficial because the sensitivity and selectivity of glycan detection can be improved as well as the chromatographic behavior. However, upon derivation with a reagent having the fluorescent moiety, the functional group of the compound is estimated. Mass spectrometry ("MS") is then required to identify the specific compound. Furthermore, certain tagging reagents have good fluorescence signal, but a poor MS signal.

There is a need, therefore, for compounds which can react with glycans and other biomolecules to provide a derivative compound (or one that is tagged or labeled by the reagent), and/or a conjugate glycan, that produces reliable mass spectrometry and fluorescence signals.

SUMMARY OF THE INVENTION

Provided herein are MS active compounds useful in fluorescence labeling of glycans such as oligosaccharides, N-linked glycans, O-linked glycans and other biomolecules including, but not limited to, proteins and peptides that contain an aldehyde group or a ketone group. These MS active, fluorescent compounds have three functional components: (a) a tertiary or quaternary amino group or other MS active atom; (b) a highly fluorescent moiety, and (c) an amine group that can react with a ketone or aldehyde group of the glycan or other biomolecule. The amine group provides effective labeling of glycans through reductive amination. The fluorescent moiety provides the fluorescent signal. The tertiary amino group (otherwise sometimes referred to herein as the MS active atom) provides a strong MS signal.

In particular, compounds of the various formulas are described herein. Each compound can be a reagent for fluorescence labeling and enhanced MS signaling of glycans and other biomolecules. The terms "labeling" and "tagging" are used interchangeably through this specification.

The MS active, fluorescence tagging compounds can be of the structural Formula I:

Formula I
and salts or solutes thereof,
wherein
FL is a fluorophore, such as a phenyl, quinoline, naphthalene, coumarin, quinolinones or rhodamine compound;
$R^3$ is

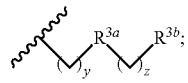

$R^{3a}$ is selected from ester, amide, amine, oxygen, urea, carbamate, carbonate, sulfur, thiourea, thiocarbamate, alkyl or carbonyl;
$R^{3b}$ is

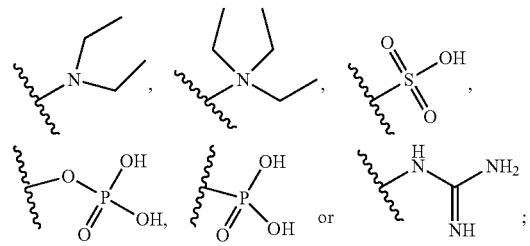

y=0-12; and
z=1-12.

In an embodiment, the compound of Formula I is selected from

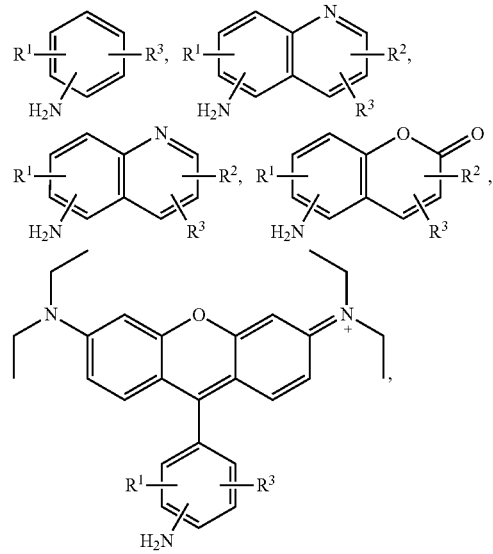

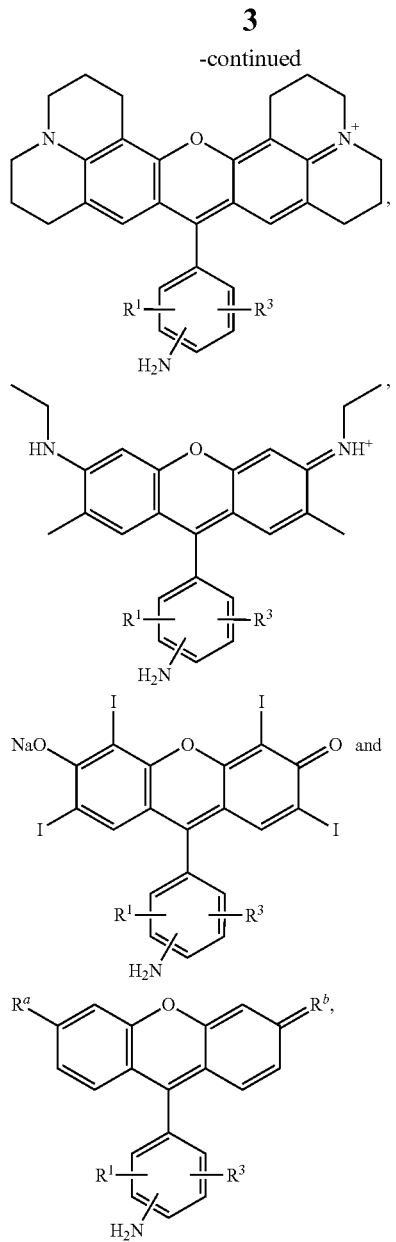

and salts or solvates thereof, wherein $R^1$ and $R^2$ are independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^3$ is

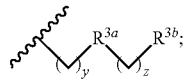

$R^{3a}$ is selected from ester, amide, amine, oxygen, urea, carbamate, carbonate, sulfur, thiourea, thiocarbamate, alkyl or carbonyl;

$R^{3b}$ is

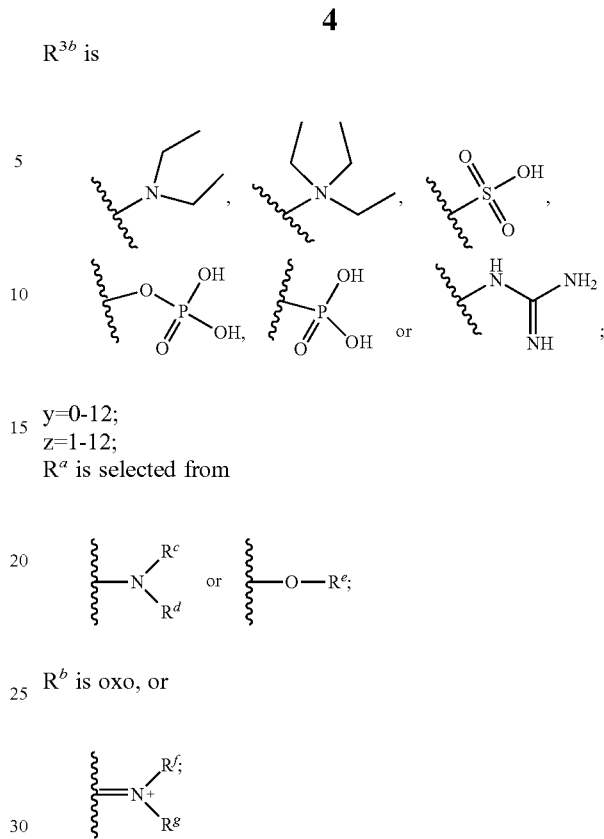

y=0-12;
z=1-12;
$R^a$ is selected from

[structures: $-N(R^c)(R^d)$ or $-O-R^e$]

$R^b$ is oxo, or

[structure: $=N^+(R^f)(R^g)$];

and $R^c$, $R^d$, $R^e$, $R^f$ and $R^g$ are independently selected from hydrogen and optionally substituted alkyl.

The compounds described herein can have optical centers and therefore can occur in different enantiomeric and diastereomeric configurations. The present compounds further include enantiomers, diastereomers and other stereoisomers of such compounds of each formula, as well as racemic compounds and racemic mixtures and other mixtures of stereoisomers thereof.

DETAILED DESCRIPTION

Biopolymers, such as glycans, play significant roles in physiological and pathological processes. Labeling (otherwise referred to herein as "tagging") glycans with fluorescent reagent compounds can improve detection of the glycan. Quantitative analysis of glycans from normal and disease specimens can provide insight into disease onset and progression. Relative glycan quantification can be accomplished through modification of the glycans with either chromogenic or fluorogenic tags for optical measurement or isotopic tags for mass spectrometric analysis. Yang et. al., *Glycan Analysis by Isobaric Aldehyde Reactive Tags and Mass Spectrometry*, 85 ANAL CHEM. 8188 (2013). The ion abundance of N-linked glycans in electrospray ionization mass spectrometry ("ESI MS") can be increased by derivatizing the glycans with neutral, hydrophobic reagents. Walker et. al., *Hydrophobic Derivatization of N-linked Glycans for Increased Ion Abundance in Electrospray Ionization Mass Spectrometry*, 22 J. AM. SOC. MASS SPECTROM. 1309 (2011). In other words, hydrophobic derivatization of glycans can increase ion abundance in ESI MS. In addition, we have uncovered that by using a reagent or tagging compound having a high pKa, MS signaling of the derivatized or tagged glycan is further enhanced.

Hence, provided herein are novel compounds useful in the fluorescence tagging of glycans and with enhanced MS signaling such as N-linked glycans O-linked glycans and other bio-molecules including, but not limited to, proteins, peptides and amino acids. These compounds are useful to analyze glycans and/or other biomolecules in a sample. To analyze a glycan or other biomolecule, the glycan can be labeled with one of the compounds described herein and then subjected to liquid chromatography, and mass spectrometry and fluorescence detection.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to and including 20, preferably 1 to 10, and more preferably 1 to 6, carbon atoms. Alkyl groups can be optionally substituted as defined herein without changing or effecting the fluorescent or mass spec properties of the molecule. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—$CH_2$—).

The term "alkylamino," as used herein can be a mono- or dialkylated groups (also referred to "dialkylamino") such as, for example, N-methylamino, N-ethylamino, N,N-dimethylamino, N,N-ethylmethylamino and the like and combination, refers to —NRR', wherein R is independently selected from the group consisting of hydrogen and alkyl, and R' is alkyl, any of which can themselves be optionally substituted and the dialkyamino group can further comprise a spacer (sometimes referred to as a linker or linker group). A molecular spacer or simply a "spacer" in chemistry is any part of a molecule that provides a connection between two other functional parts of a molecule, for example, the rapid reacting portion, the MS active portion and the fluorescent portion.

The term "parent molecular moiety" as used herein means and includes a phenyl, quinoline, naphthalene, coumarin, quinolinones or rhodamine The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which can themselves be optionally substituted.

The term "aryl," as used herein, alone or in combination, means a carbocyclic aromatic system containing one, two or three rings wherein such rings can be attached together in a pendent manner or can be fused. The term "aryl" embraces aromatic radicals such as benzyl, phenyl, naphthyl, anthracenyl, phenanthryl, indanyl, indenyl, annulenyl, azulenyl, tetrahydronaphthyl, heteroaryl (e.g., pyridine) and biphenyl.

The terms "benzo" and "benz," as used herein, alone or in combination, refer to the divalent radical $C_6H_4$= derived from benzene. Examples include benzothiophene and benzimidazole.

The term "carbamate," as used herein, alone or in combination, refers to an ester of carbamic acid (—NHCOO—) which can be attached to the parent molecular moiety from either the nitrogen or acid end, and which can be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cycloalkyl" refers to a carbocyclic substituent obtained by removing a hydrogen from a saturated carbocyclic molecule and having three to fourteen carbon atoms. In one embodiment, a cycloalkyl substituent has three to ten carbon atoms. Examples of cycloalkyl include cyclopropyl, cyclobutyl, cyclopentyl and cyclohexyl.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, can have an iodo, bromo, chloro or fluoro atom within the radical. Dihalo and polyhaloalkyl radicals can have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—$CF_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms can optionally be oxidized and the nitrogen heteroatom can optionally be quaternized. The heteroatom(s) O, N and S can be placed at any interior position of the heteroalkyl group. Up to two heteroatoms can be consecutive, such as, for example, —$CH_2$—NH—$OCH_3$.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom can be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the compounds are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups can be optionally substituted unless specifically prohibited.

The term "optionally substituted" means the anteceding group can be substituted or unsubstituted. When substituted, the substituents of an "optionally substituted" group can include, without limitation, one or more substituents independently selected from the following groups or a specific designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents can be joined together to form a fused five-, six-, or seven-membered carbocyclic or heterocyclic ring consisting of zero to three heteroatoms, for example forming methylenedioxy or ethylenedioxy. An optionally substituted group can be unsubstituted (e.g., $—CH_2CH_3$), fully substituted (e.g., $—CF_2CF_3$), monosubstituted (e.g., $—CH_2CH_2F$) or substituted at a level anywhere in-between fully substituted and monosubstituted (e.g., $—CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a moiety can be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which can be optionally substituted. Such R and R' groups should be understood to be optionally substituted as defined herein. Whether an R group has a number designation or not, every R group, including R, R' and R'' where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups can be attached to a parent molecular moiety or can occupy a position in a chain of elements from either end as written. Thus, by way of example only, an unsymmetrical group such as $—C(O)N(R)—$ can be attached to the parent molecular moiety at either the carbon or the nitrogen.

The term "bond" refers to a covalent linkage between two atoms, or two moieties when the atoms joined by the bond are considered to be part of larger substructure. A bond can be single, double, or triple unless otherwise specified. A dashed line between two atoms in a drawing of a molecule indicates that an additional bond can be present or absent at that position. The development and production of therapeutic proteins is becoming the fastest-growing segment of the pharmaceutical industry. The efficacy, stability and protein secretion of these large molecule drugs depend on their Post Translational Modifications ("PTMs"). Glycosylation is the most complex and common PTM and plays a vital role in the safety and efficacy of many therapeutic proteins such as recombinant antibodies. Several studies have shown the correlation between glycosylation variations caused by cell line selection and changes in culture medium parameters. Patrick Hossler et al., *Optimal and Consistent Protein Glycosylation in Mammalian Cell Culture*, 19 GLYCOBIOLOGY 926 (2009). These variations can have a profound effect on the biological activities of the mAb drugs, which leads to changes in drug potency in the final product. Regulatory agencies require monitoring of batch-to-batch recombinant antibody drug production quality and mandate detailed assessment of the protein glycosylation microheterogeneity and consistency.

The term "urea" means and includes a compound having the chemical formula $CO(NH_2)_2$ where the molecule has two $—NH_2$ groups joined by a carbonyl ($C=O$) functional group The compounds described herein can also form hydrogen bonds with other compounds. A hydrogen bond is an electromagnetic attractive interaction between polar molecules, where hydrogen is bonded to an electronegative atom such as nitrogen or oxygen. The hydrogen bond represents a strong dipole-dipole attraction. These hydrogen-bond attractions can occur between molecules (intermolecular) or within different parts of a single molecule (intramolecular). When a hydrogen atom is attached to an electronegative atom, it is considered a hydrogen bond donor. The electronegative atom is considered a hydrogen bond acceptor, whether it is bonded to a hydrogen atom or not.

Asymmetric centers exist in the compounds presented herein. These centers are designated by the symbols "R" or "S," depending on the configuration of substituents around the chiral carbon atom. It should be understood that the compounds encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of certain stereochemistry are either commercially available or can be made and resolved by techniques known in the art. Additionally, the compounds described can exist as geometric isomers and includes all cis, trans, syn, anti, entgegen (E), and zusammen (Z) isomers as well as the appropriate mixtures thereof. Additionally, compounds can exist as tautomers. All tautomeric isomers are provided. Additionally, the present compounds can exist in unsolvated as well as solvated forms with pharmaceutically acceptable solvents such as water, ethanol, and the like. In general, the solvated forms are considered equivalent to the unsolvated forms.

Hence, the compounds described herein can also be in the form of a salt or solvate, or acid addition salts. Through a reaction with either organic or inorganic acids, compounds presented herein or groups of compounds can form a salt. For example, in acid-base neutralization, an acid and a base react to form water and a salt. Basically, to react together, there must be the transfer of protons between acids and bases. Also, different acids can produce different ions. For example, an Arrhenius acid produces hydronium ions when it dissociates in water. Similarly, a Bronsted-Lowry acid is a proton donor that donates hydrogen ions to the base. Hence, proton acceptors and proton donors are the basis for the reaction and are referred to sometimes as a conjugate base or a conjugate acid. A conjugate pair refers to acids and bases with common features, where there is an equal loss/gain of protons between the pairs. For example $NH_4^+$ is the conjugate acid to the base $NH_3$ because $NH_3$ gains a hydrogen ion to form $NH_4^+$ as $H_2O$ donates a hydrogen ion to form $OH^-$, the conjugate base. On the other hand, under a different theory, a Lewis acid accepts an electron pair and a Lewis base donates an electron pair donor. Accordingly, the proton $H^+$ can be an electron pair acceptor. Moreover, a compound can be both, a Lewis acid and a Lewis base, depending on the reaction. For example, methyl iodide can behave as both, a Lewis acid and a Lewis base, where the methyl group is donated to form a salt.

The compounds of the formulas described herein can have one or more quaternary nitrogen. The quaternary nitrogen has a positive charge on the nitrogen and can be associated with a counterion and include all quaternary amine-counterion complexes of compounds when a compound includes a quaternary amine group.

The terms tagging, conjugating and derivatizing when referred to in the context of an association between a compound of Formula I through Formula X refers to the bond formation of one of the compounds with an aldehyde containing compound.

The term "oxo" indicates that the chemical compound contains oxygen linked to another atom by a double bond and can denote that the compound is derived from a specified compound by replacement of a methylene group with a carbonyl group. In addition, oxo is sometimes used as a prefix (i.e., in IUPAC nomenclature) for the functional group =O, a substituent oxygen atom connected to another atom by a double bond.

Examples of acids which can be employed to form a salt of any of the compounds provided herein include inorganic acids and organic acids as well known to those skilled in the art such as, but not limited to, N-hydroxysuccinimide, hydrochloric, hydrofluoric, hydroiodic, hydrobromic, sulfuric, hydrosulfuric, thiosulfuric, hydrocyanic, phosphoric, phosphorous, hydrochlorous, chlorous, nitrous, nitric, chloric, perchloric, sulfurous, oxalic, maleic, succinic, and citric. Salts can also be formed by coordination of the compounds with an alkali metal or alkaline earth ion. In addition, other acids can form a salt including, but not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid (D), isobutyric acid, lactic acid (DL), lactobionic acid, lauric acid, maleic acid, malic acid (–L), malonic acid, mandelic acid (DL), methanesulfonic acid, naphthalene-1,5, disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (–L), salicylic acid, sebacic acid, stearic acid, succinic acid, sulfuric acid, tartaric acid (+L), thiocyanic acid, toluenesulfonic acid (p), undecylenic acid.

For the compounds described herein, the counterion can be the conjugate base formed after reacting a compound or groups of compounds with an acid. In other words, counterion holds the opposite charge to that of the compound or compounds it is associated with. Thus, with respect to possible salts of the compounds herein having a conjugate acid of $NH_4^+$, the counterion represents the anionic part of the salt. In addition, it can be possible to have four organic substituents on the nitrogen. These species are not amines but are quaternary ammonium cations having a charged nitrogen center. Quaternary ammonium salts can exist with many kinds of anions.

Hence, counterions of a salt compound described herein can include, but are not limited to, any of the following common anions and oxoanions: N-hydroxysuccinimidyl, hydride ($H^-$), fluoride ($F^-$), chloride ($Cl^-$), bromide ($Br^-$), iodide ($I^-$), oxide ($O^{2-}$), hydroxide ($OH^-$), peroxide ($O_2^{2-}$), sulfide ($S^{2-}$), hydrogen sulfide ($HS^-$), selenide ($Se^{2-}$), nitride ($N^{3-}$), azide ($N_3^-$), phosphide ($P^{3-}$), arsinide ($As^{3-}$), carbide ($C^{4-}$), cyanide ($CN^-$), hypochlorite ($ClO_1^-$), chlorite ($ClO_2^-$), chlorate ($ClO_3^-$), perchlorate ($ClO_4^-$), sulfite ($SO_3^{2-}$), sulfate ($SO_4^{2-}$), hydrogen sulfate ($HSO_4^-$), thiosulfate ($S_2O_3^{2-}$), nitrite ($NO_2^-$), nitrate ($NO_3^-$), phosphite ($PO_3^{2-}$), phosphate ($PO_4^{3-}$), (mono)hydrogen phosphate ($HPO_4^{2-}$), dihydrogen phosphate ($H2PO_4^-$), carbonate ($CO_3^{2-}$), hydrogen carbonate ($HCO_3^-$), oxalate ($C_2O_4^{2-}$), cyanate ($NCO^-$), isocyanate ($OCN^-$), thiocyanate ($SCN^-$), chromate ($CrO_4^{2-}$), dichromate ($Cr_2O_7^{2-}$), permanganate ($MnO_4^-$).

Derivatization Through Reductive Amination

Compounds for labeling biomolecules such as N and O glycans, with MS active fluorescent compounds of Formula I, as well as conjugates resulting therefrom are provided. In an embodiment, a biomolecule (such as a glycan) are tagged, derivatized or conjugated through an aldehyde or ketone with an amine of one or more of the compounds provided herein containing fluorescent, MS active properties through reductive amination. If a carbonyl functionality (e.g. ketone, aldehyde) is present on the reagent, it is possible that the reagent could self-react and/or form linear polymers under the conditions of reductive amination. Therefore, considerations must be made towards the same.

General conditions for the reductive amination reaction can be applied for tagging. For example, the reaction can be conducted in the presence reducing agents such as sodium cyanoborohydride or sodium triacetoxyborohydride. The reaction can be conducted in a mixture of citric acid and/or acetic acid with an organic solvent such as dimethylsulfoxide. The reaction can also be conducted in a solvent selected from tetrahydrofuran, dichloromethane, 1,2-dichloroethane, ethanol, methanol or isopropanol, toluene and xylene, and mixtures thereof.

The following schematic depicting labeling (tagging) a glycan using a compound of Formula I through reductive amination:

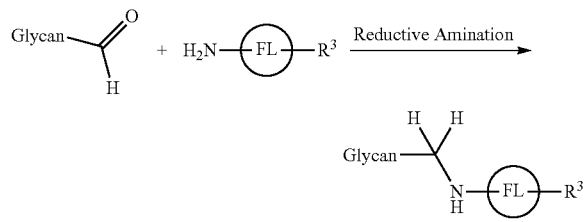

wherein FL and R³ are as described above.

The following schematic shows the tagging of an amine containing glycan through reductive amination:

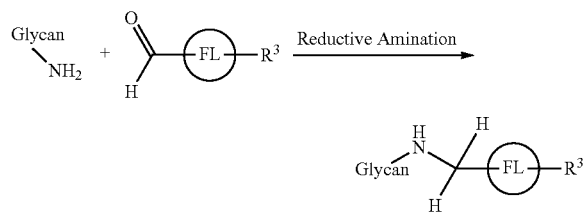

wherein FL and R³ are as described above.

Quinoline Based MS Active Fluorescence Tagging Compounds MS active, fluorescence tagging compounds can be a quinoline derivative of the structural Formula II:

Formula II

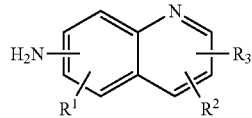

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^3$ is

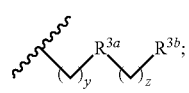

$R^{3a}$ is selected from ester, amide, amine, oxygen, urea, carbamate, carbonate, sulfur, thiourea, thiocarbamate, alkyl or carbonyl;

$R^{3b}$ is,

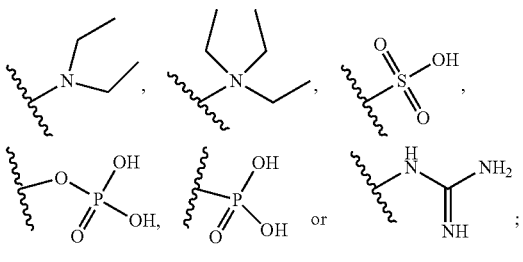

y=0-12;
z=1-12;
and salts or solvates thereof.

Compounds of structural Formula II are provided, with the proviso that said compound of Formula II is other than 6-amino-N-[2-(diethylamino)ethyl]-2-quinolinecarboxamide, and with the proviso that when y is one, $R^{3a}$ is amide, $R^{3b}$ is other than

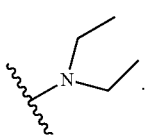 [SMILES: *N(CC)CC]

In an embodiment, the compound of Formula II, with the proviso that when y is zero, $R^{3a}$ is amine, oxygen or sulfur and z is two, $R^{3b}$ is other than

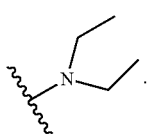

In an embodiment, the compound of Formula II, with the proviso that when y is one and $R^{3a}$ is an amide, and z is two or three, $R^{3b}$ is other than

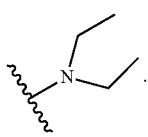 [SMILES: *N(CC)CC]

In yet another embodiment, compounds of Formula IIA are provided as follows:

Formula IIA

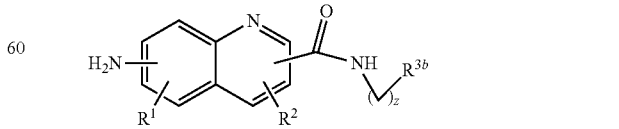

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

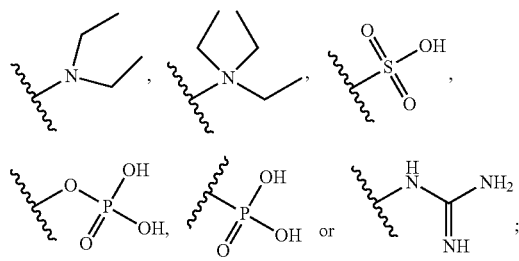

z=1-12;
and salts or solvates thereof.

In an embodiment, the compound of Formula IIA is other than 6-amino-N-[2-(diethylamino)ethyl]-2-quinolinecarboxamide.

Compounds of the structural Formula IIB are provided as follows:

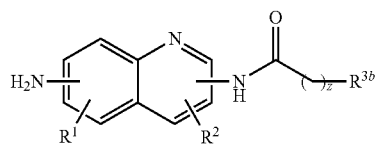

Formula IIB wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

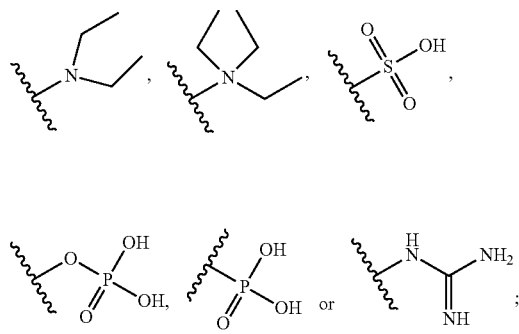

z=1-12;
and salts or solvates thereof.

Compounds of the structural Formula IIC are provided as follows:

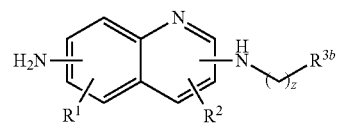

Formula IIC wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

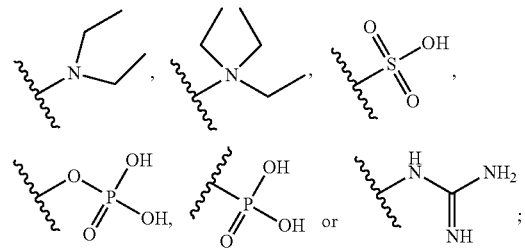

z=1-2;
and salts or solvates thereof.

In an embodiment, the compound of Formula IIC is provided with the proviso that when z is two, $R^{3b}$ is other than

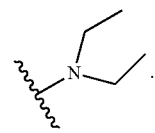 [SMILES: *N(CC)CC]

Compound of Formula IID are provided as followed:

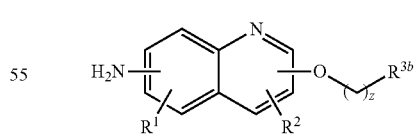

Formula IID wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

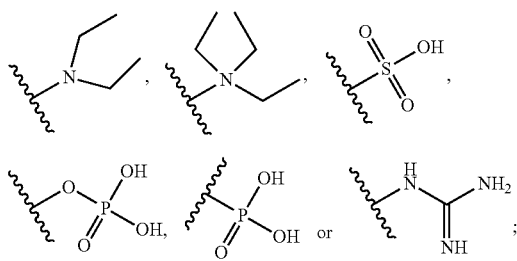

z=1-12;
and salts or solvates thereof.

In an embodiment, a compound of Formula IID is provided with the proviso that when z is two, $R^{3b}$ is other than

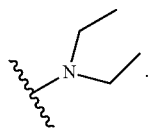

Also provided are compounds of the structural Formula IIE:

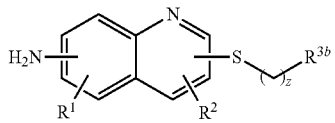

Formula IIE wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

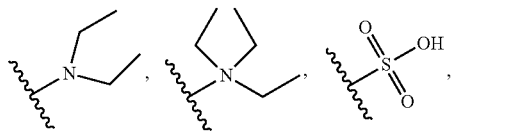

z=1-12;
and salts or solvates thereof.

In an embodiment, compounds of Formula IIE are provided with the proviso that when z is two, $R^{3b}$ is other than

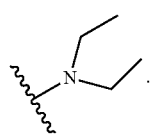 [SMILES: *N(CC)CC]

Compounds of Formula IIF are further provided as follows:

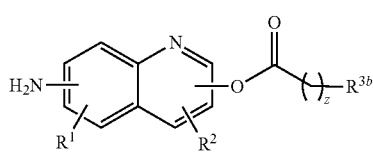

Formula IIF wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

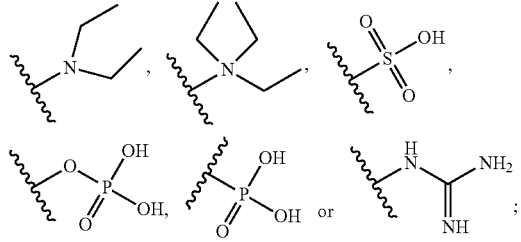

z=1-12;
and salts or solvates thereof.

Further provided herein are compounds of Formula IIG:

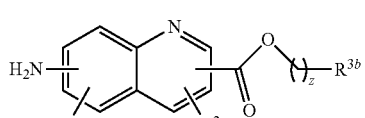

Formula IIG wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

R$^{3b}$ is

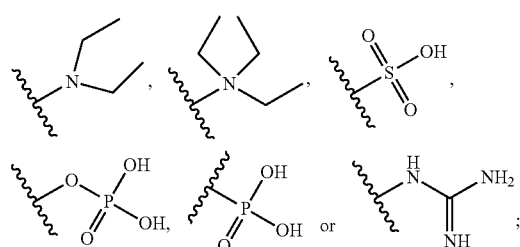

z=1-12;
and salts or solvates thereof.

In addition, provided below are exemplary compounds (Table A) of the structural Formulas II, IIA, IIB, IIC, IID, IIE, BF or IIG which can be useful for fluorescent labeling of glycans and subsequent analysis by means of liquid chromatography and mass spectrometry. The compounds of structural Formulas II, IIA, IIB, IIC, IID, IIE, BF or IIG can be optionally substituted with any group that does not substantially reduce the fluorescence of the compound.

TABLE A

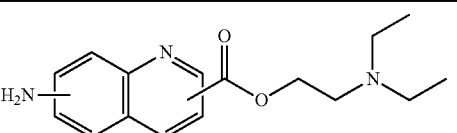
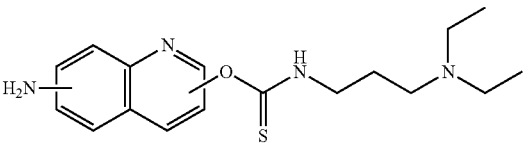
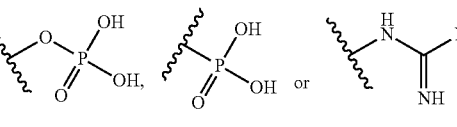
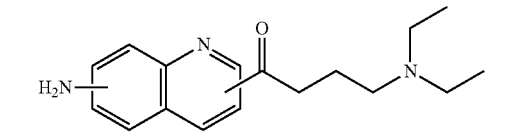
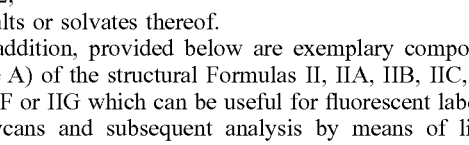
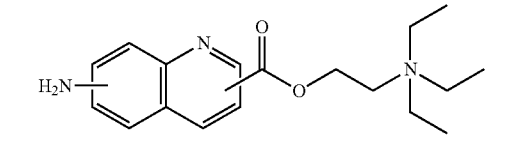
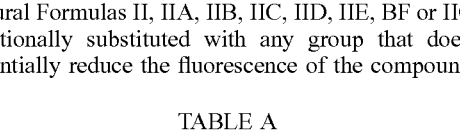
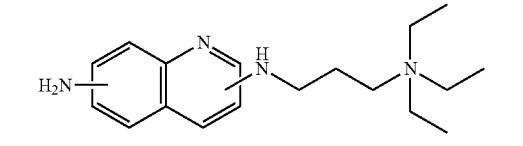

TABLE A-continued

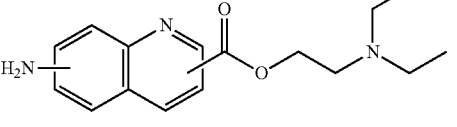
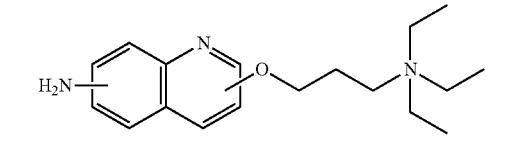
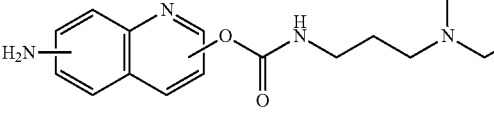
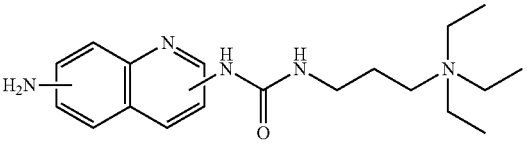
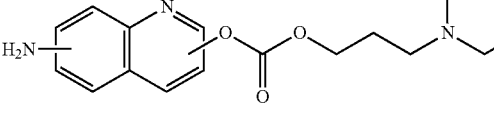
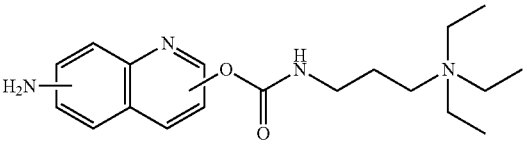
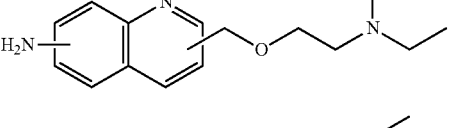
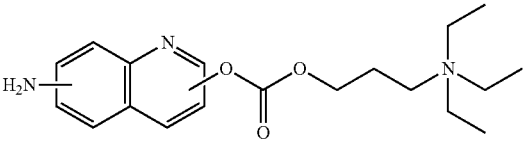
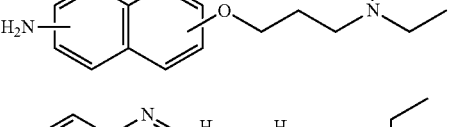
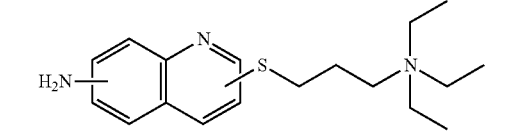

TABLE A-continued
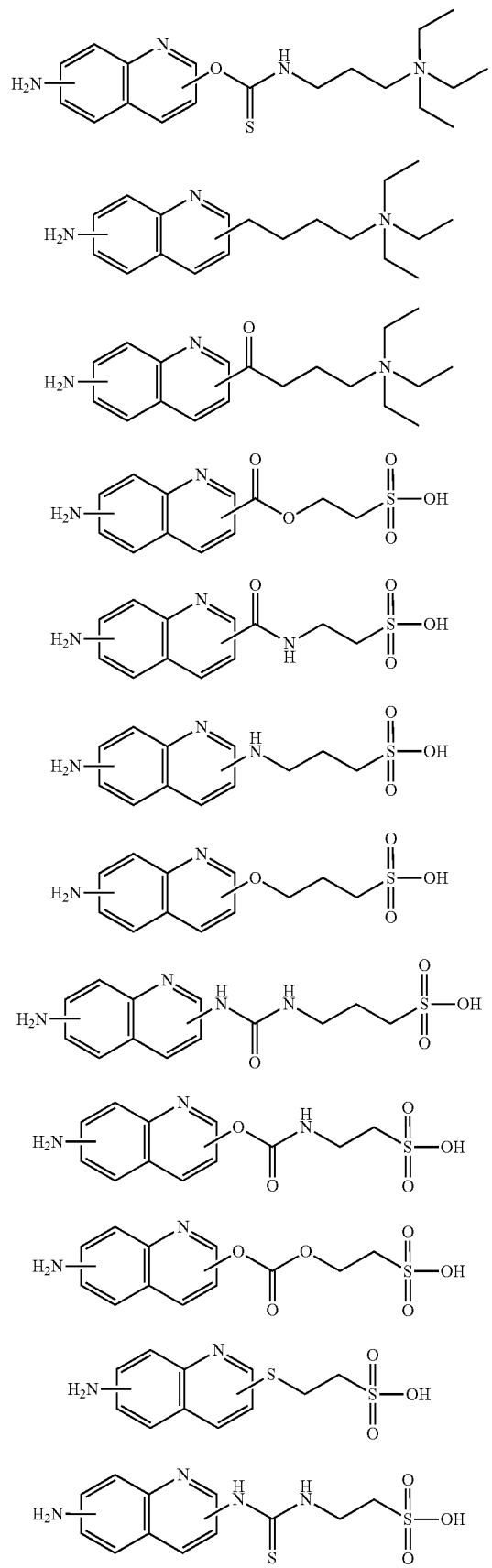
TABLE A-continued
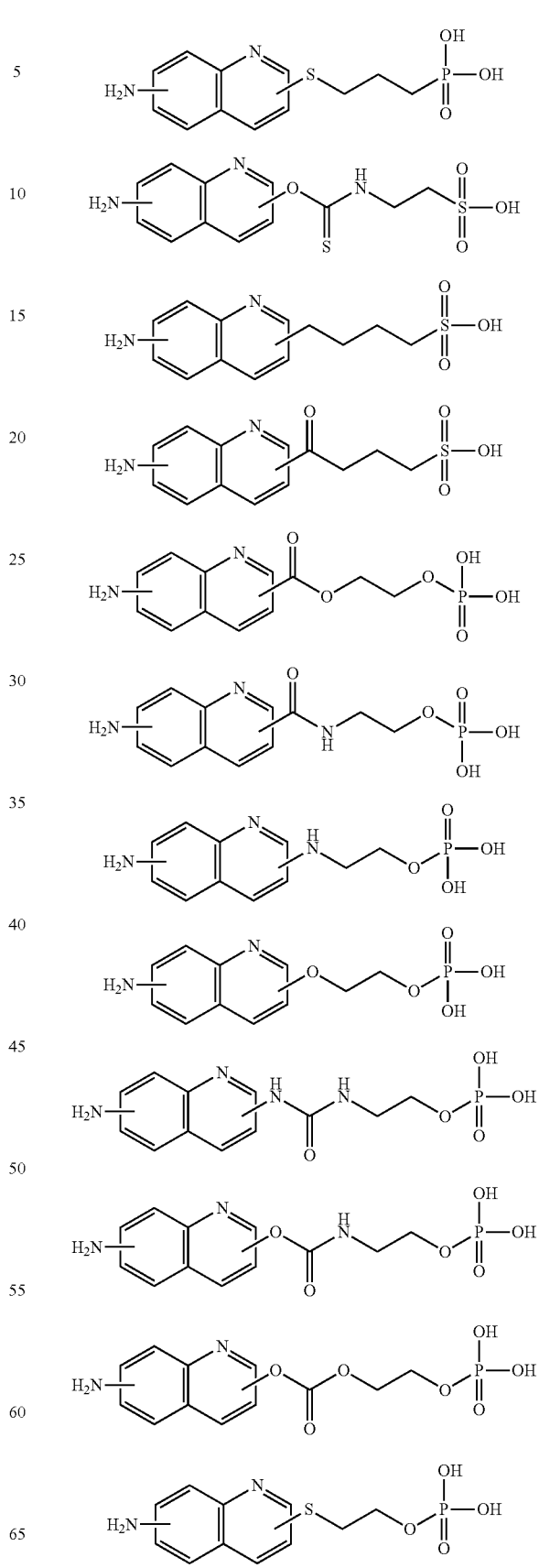

TABLE A-continued
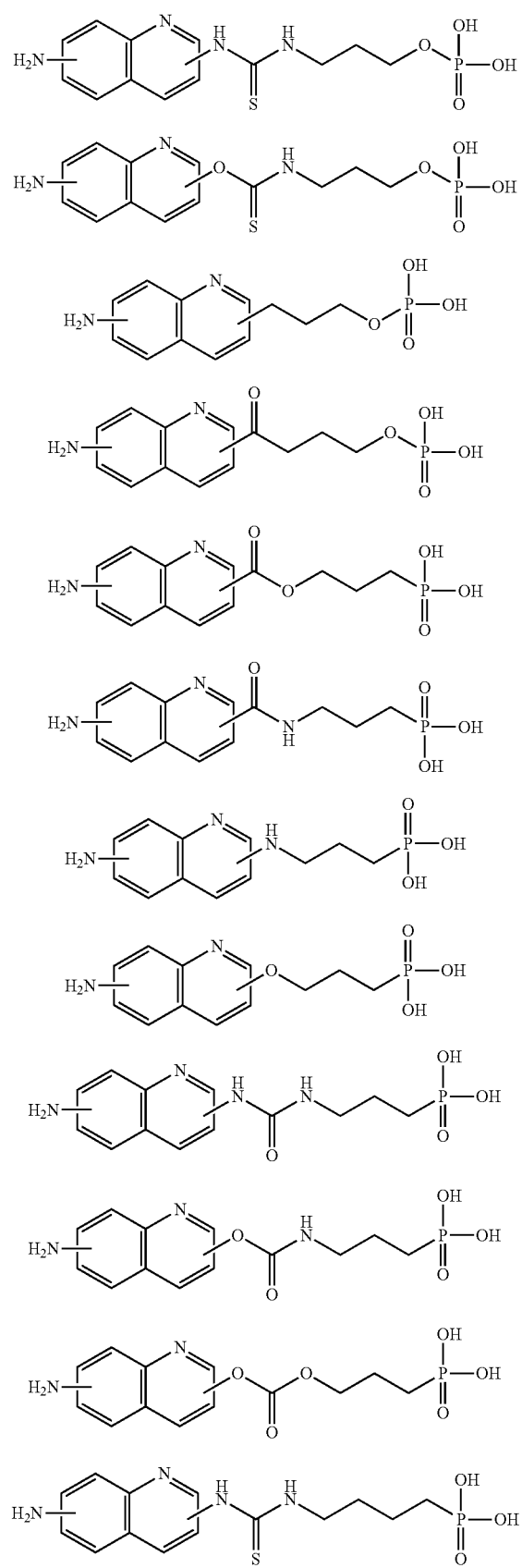
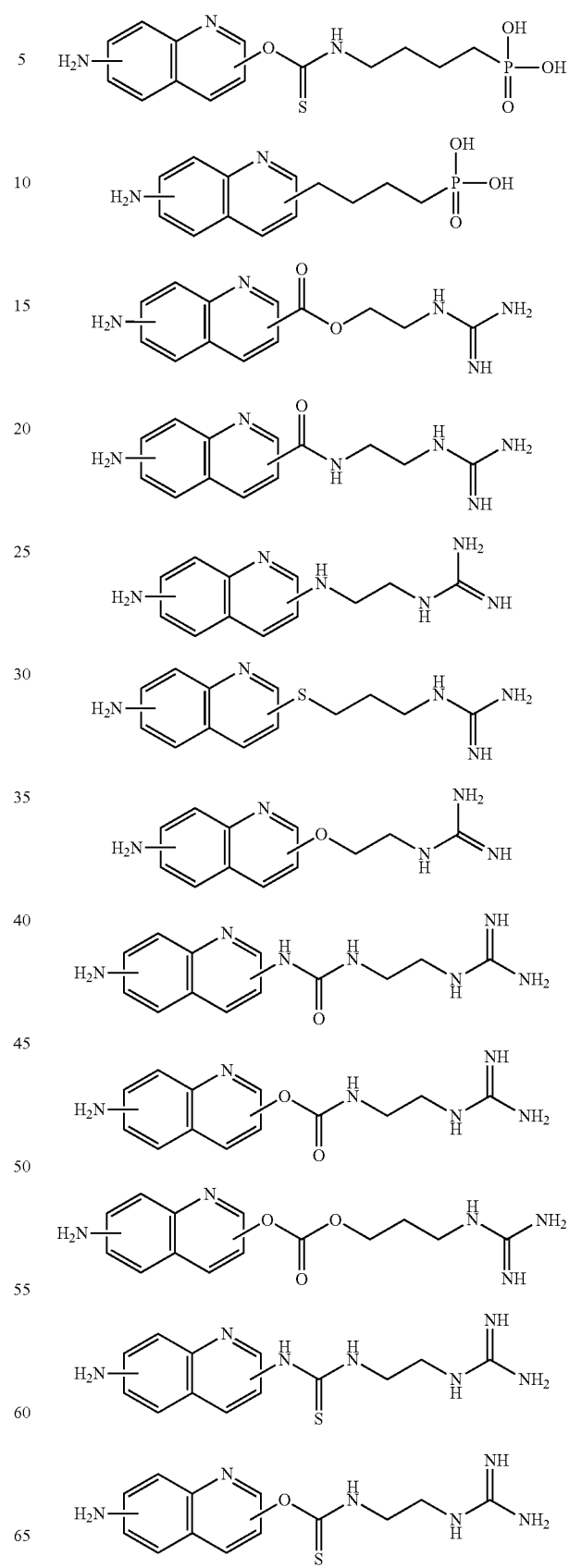

TABLE A-continued

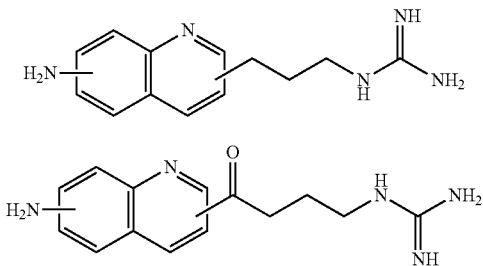

Provided herein are compounds of Formula II, IIA, IIB, IIC, IID, IIE, IIF or IIG wherein $R^1$ is hydrogen. In an embodiment, the compounds of Formula II, IIA, IIB, IIC, IID, IIE, IIF or IIG include compounds wherein $R^2$ is hydrogen. The compounds of Formula II, IIA, IIB, IIC, IID, IIE, IIF or IIG are also provided wherein $R^1$ and $R^2$ are hydrogen.

Methods for tagging, derivatizing or conjugating biomolecules containing at least one ketone group or aldehyde group with a compound of Formula II, IIA, IIB, IIC, IID, IIE, IIF or IIG, or a compound of Table A by reductive amination reaction are further provided. The reaction between a compound of Formula II and an aldehyde containing biomolecule, such as a glycan can be conducted under conditions that facilitate reductive amination in the presence of a reducing agent, such as from sodium cyanoborohydride or sodium triacetoxyborohydride. The reaction can be carried out in a solution or suspension of a compound of Formula II, IIA, IIB, IIC, IID, IIE, IIF or IIG, or a compound of Table A in an acidic media, for example in citric acid or acetic acid, and mixing with a solution or suspension of a reducing agent such as cyanoborohydride or sodium triacetoxyborohydride in an organic solvent, for example, tetrohydrofuran or dimethylsulfoxide.

Methods for analyzing a biomolecule containing an aldehyde group, such as a glycan, in a sample containing at least one biomolecule by means of liquid chromatography and mass spectrometry are provided. These methods comprise the step of labeling the biomolecule in the sample by reacting with a compound of Formula II, IIA, IIB, IIC, IID, IIE, IIF or IIG, or a compound of Table A for a time and under conditions suitable to facilitate the labeling through reductive amination; and subjecting the labeled conjugate to liquid chromatography and mass spectrometry.

Analytical kits for assaying glycans and other biomolecules comprise (i) a labeling module comprising a compound of Formula II and salts and solvate thereof; and optionally one or more of the following:
  (i) a deglycosylation module comprising one or more endoglycosidases, a buffer, and one or more surfactants, or one or more compounds that can perform a chemical release of glycoprotein; and
  (ii) a separation device for clean-up such as a solid phase extraction device, or a centrifugal filtration device or the like.

Solid phase extraction ("SPE") is a sample preparation technology that utilizes solid particle, chromatographic packing material, usually contained in a cartridge type device, to chemically separate the different components of a sample. The SPE device having a chromatographic bed can perform four critical functions to make the analysis of the sample more successful including: (1) simplification of complex sample matrix along with compound purification; (2) reduction in ion suppression or enhancement in MS applications; (3) capability to fractionate sample matrix to analyze compounds by class; and (4) trace concentration enrichment of very low level compounds. In SPE, samples are typically in the liquid state although specialty applications may be run with some samples in the gas phase.

The separation device of the kit described herein, however, can include, but is not limited to, devices using reversed phase chromatography, ion exchange chromatography and hydrophilic interaction chromatography ("HILIC") and include devices which utilize graphitic stationary phases such as porous graphitized carbon and mobile phases acidified by formic acid or are separated by capillary electrophoresis. In addition, desalting, buffer exchanges or diafiltration are methodologies associated with removing salts or solvents in solutions containing biomolecules. The removal of salts or the exchange of buffers can be accomplished in a centrifugal device such as the Amicon Ultra-0.5 device by concentrating the sample, then reconstituting the concentrate to the original sample volume with any desired solvent. The process of "washing out" can be repeated until the concentration of the contaminating microsolute has been sufficiently reduced. Noteworthy, as part of the kit, glycoproteins can be chemically deglycosylated through alkaline beta-elimination or hydrazinolysis as well as by endoglycosidases.

Glycans and other biomolecules can be conjugated to MS active fluorescent compounds of Formula II and salts or solvates thereof. The following schematic shows the tagging of a glycan using a compound of Formula II through reductive amination:

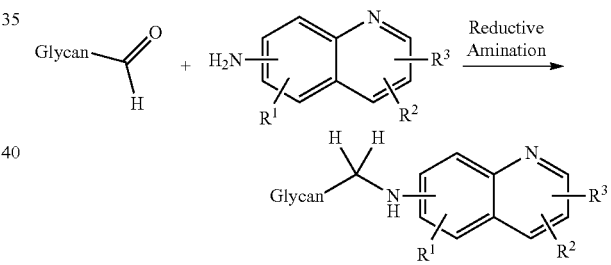

where FL $R^1$, $R^2$ and $R^3$ are as described herein.

Therefore, methods of tagging biomolecules (also referred to herein sometimes as biomolecules), such as glycans, with the MS active fluorescent compounds of Formula II, as well as conjugates resulting therefrom are provided.

Coumarin Based MS Active Fluorescence Tagging Compounds

The MS active, fluorescence tagging compounds can be a coumarin derivative of Formula III:

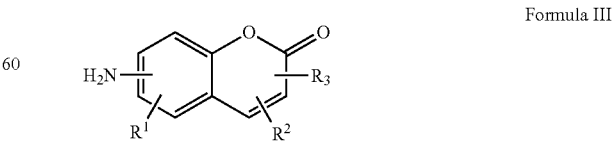

Formula III wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^3$ is

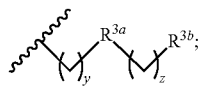

$R^{3a}$ is selected from ester, amide, amine, oxygen, urea, carbamate, carbonate, sulfur, thiourea, thiocarbamate, alkyl or carbonyl;

$R^{3b}$ is

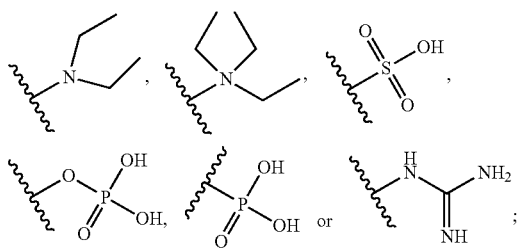

y=0-12;
z=1-12;
and salts or solvates thereof.

Provided herein are compounds of Formula III, with the proviso that when y is zero, $R^{3a}$ is ester and z is two, $R^{3b}$ is other than

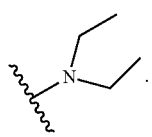 [SMILES: *N(CC)CC]

In an embodiment, the compounds of the structural Formula IIIA are:

Formula IIIA

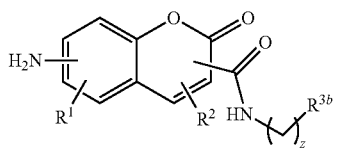

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

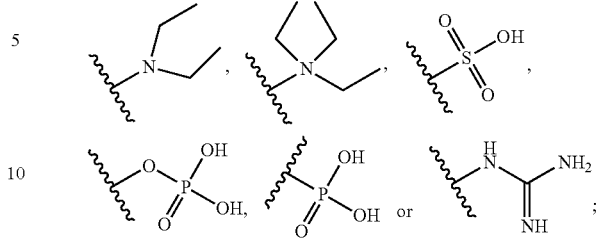

z=1-12;
and salts or solvates thereof.

In an embodiment, provided herein are compounds of the Formula IIIB:

Formula IIIB

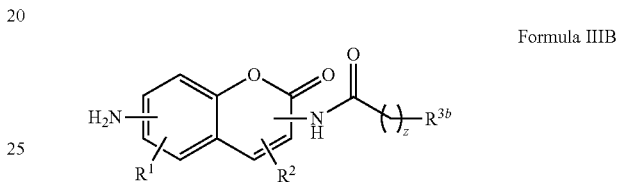

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

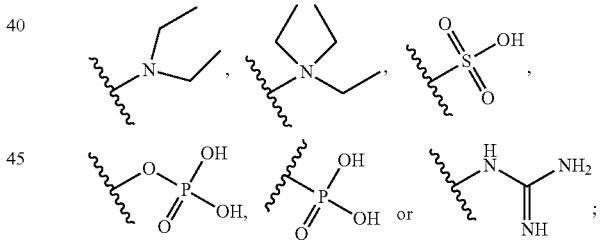

z=1-12;
and salts or solvates thereof.

In an embodiment, provided herein are compounds of Formula IIIC:

Formula IIIC

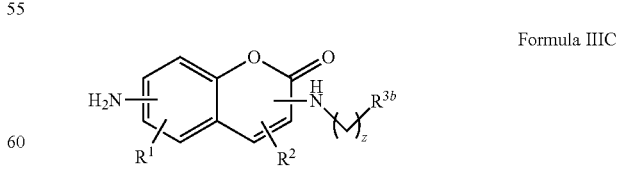

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

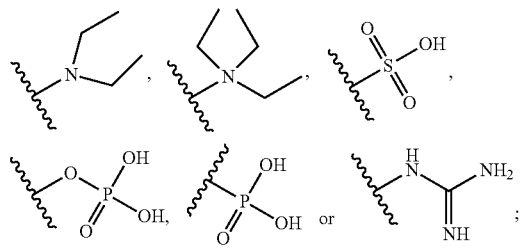

z=1-12;
and salts or solvates thereof.

In yet another embodiment, provided herein are compounds of the structural Formula IIID:

Formula IIID

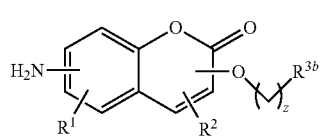

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

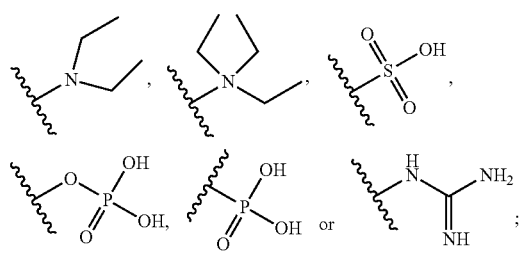

z=1-12;
and salts or solvates thereof.

In an embodiment, provided herein are compounds of the structural Formula IIIE:

Formula IIIE

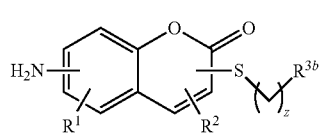

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

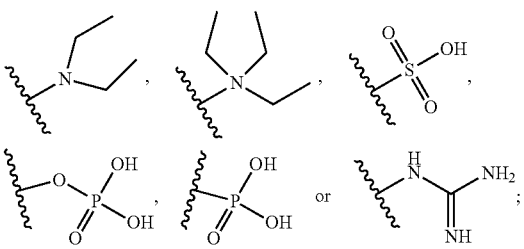

z=1-12;
and salts or solvates thereof.

In an embodiment, provided herein are compounds of the structural Formula IIIF:

Formula IIIF

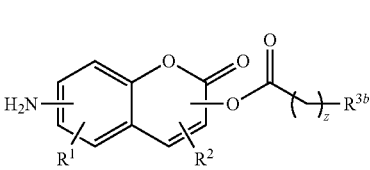

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

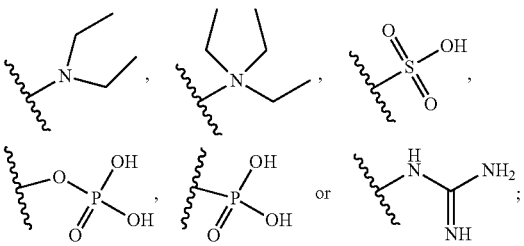

z=1-12;
and salts or solvates thereof.

In an embodiment, provided herein are compounds of Formula IIIG:

Formula IIIG

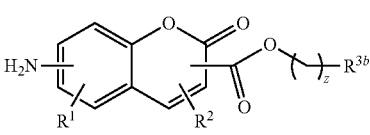

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

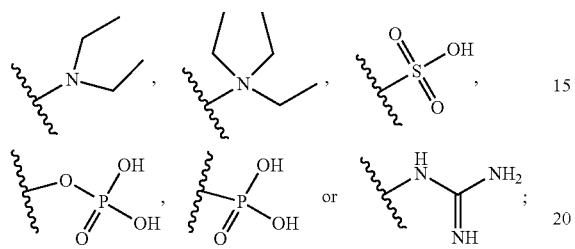

z=1-12;

and salts or solvates thereof.

In an embodiment, compounds are provided of the structural Formula IIIG, with the proviso that when y is zero, and z is two, $R^{3b}$ is other than

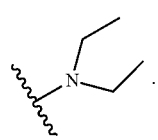 [SMILES: *N(CC)CC]

In addition, provided below are exemplary compounds (Table B) of the structural Formulas III, IIIA, IIIB, IIIC, IIID, IIIE, IIIF or IIIG which can be useful for fluorescent labeling of glycans and subsequent analysis by means of liquid chromatography and mass spectrometry. The compounds of structural Formulas III, IIIA, IIIB, IIIC, IIID, IIIE, IIIF or IIIG could be optionally substituted with any group that does not substantially reduce the fluorescence of the compound.

TABLE B

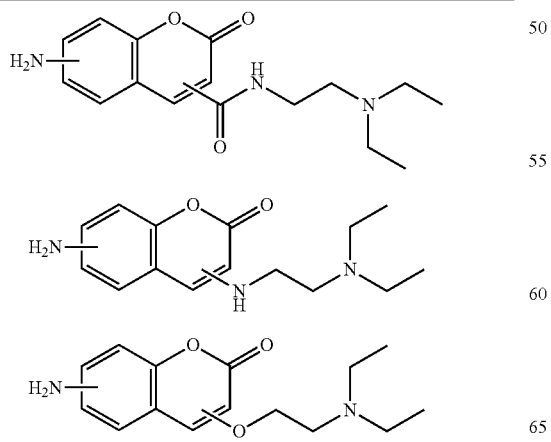

TABLE B-continued

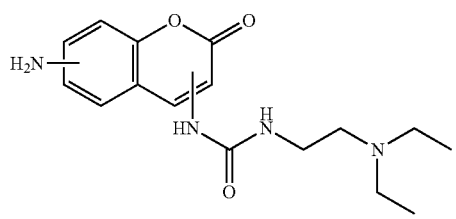

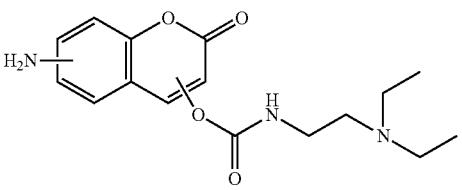

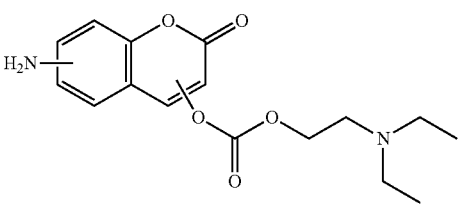

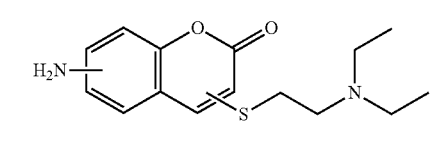

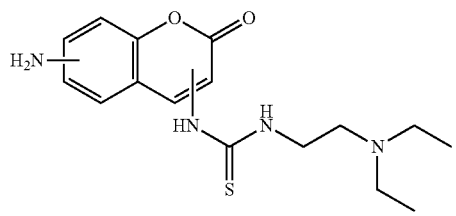

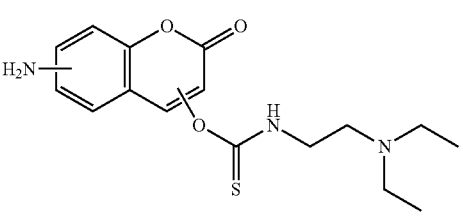

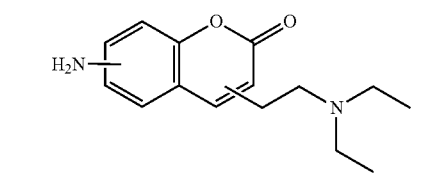

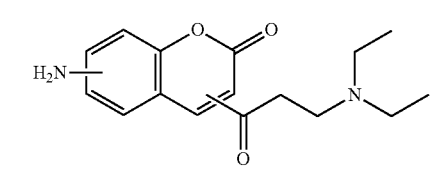

TABLE B-continued
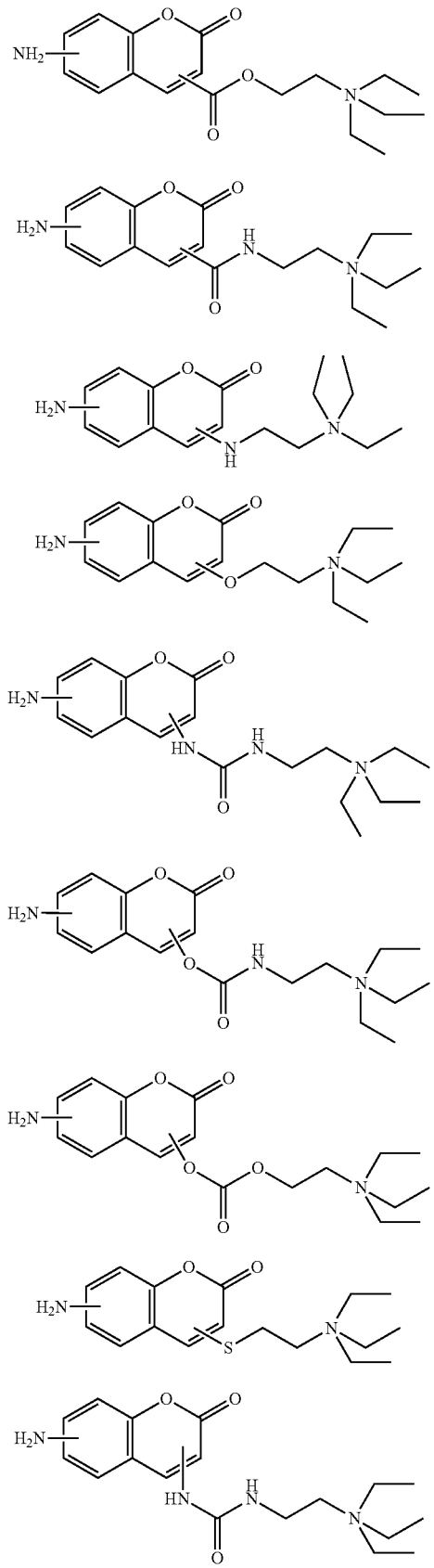
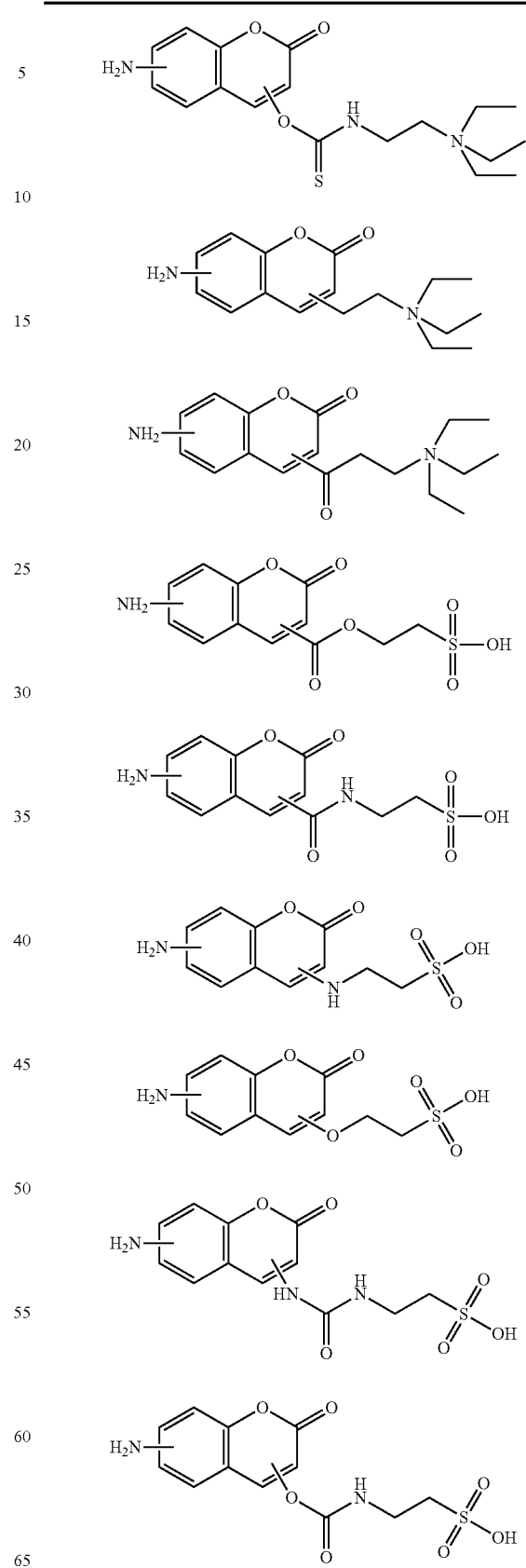

TABLE B-continued
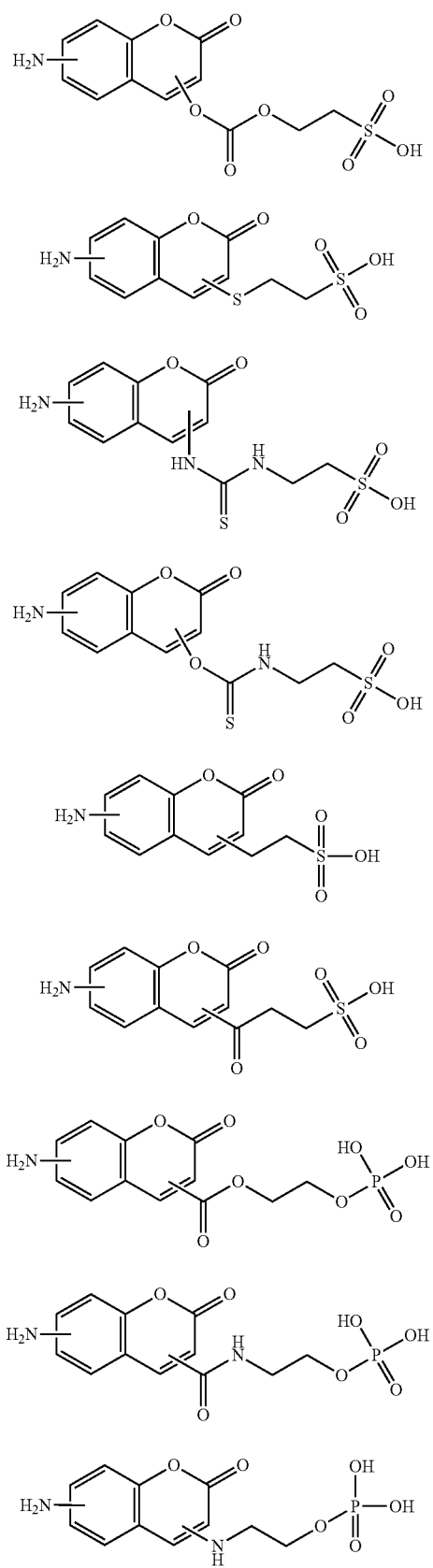
TABLE B-continued
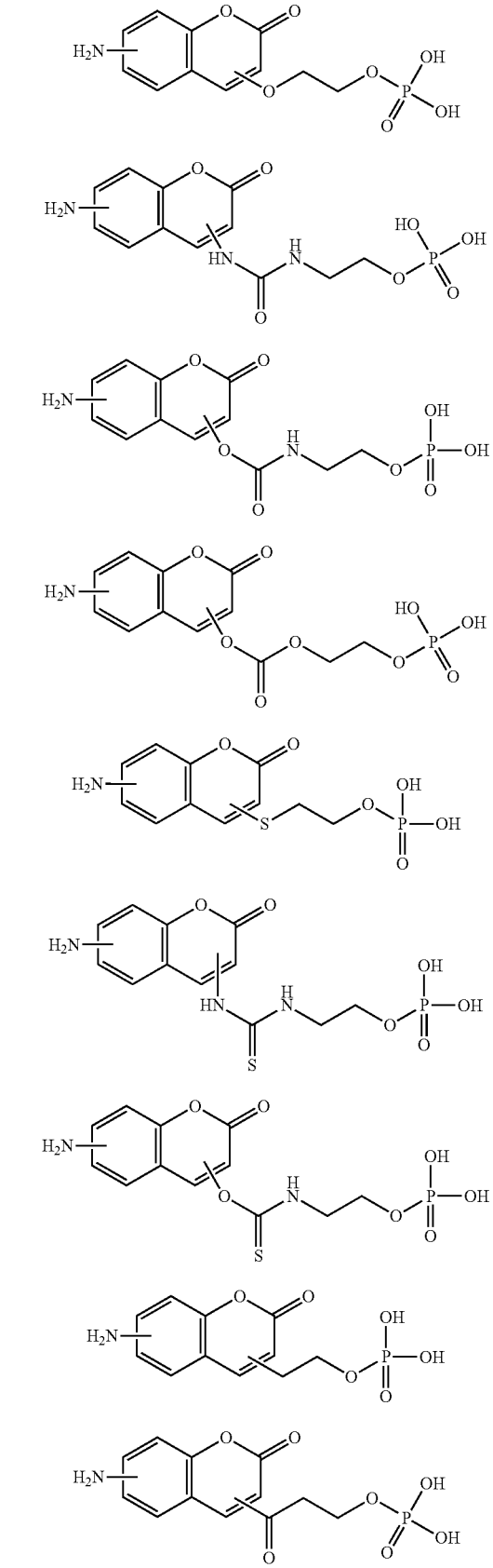

TABLE B-continued
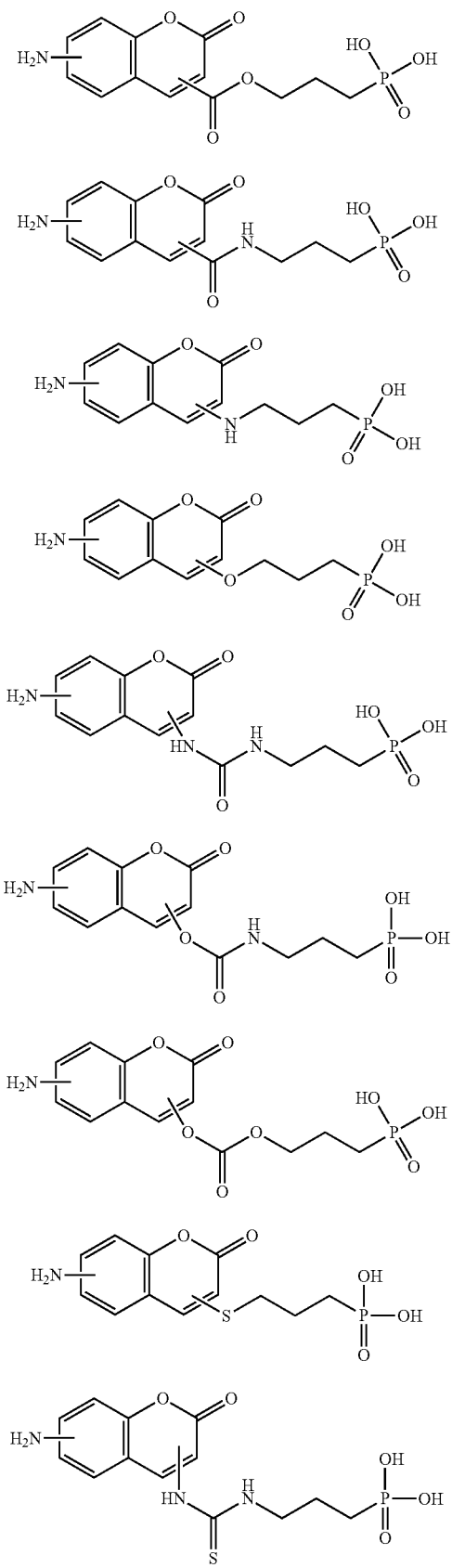
TABLE B-continued
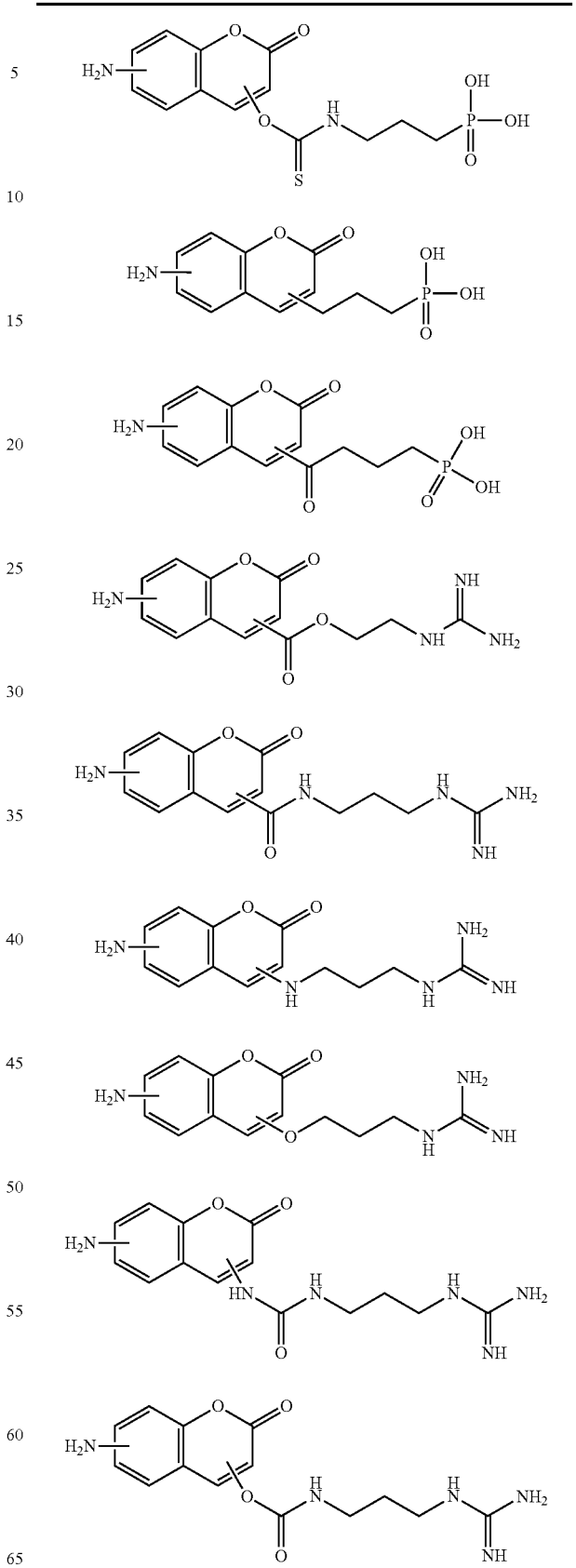

TABLE B-continued

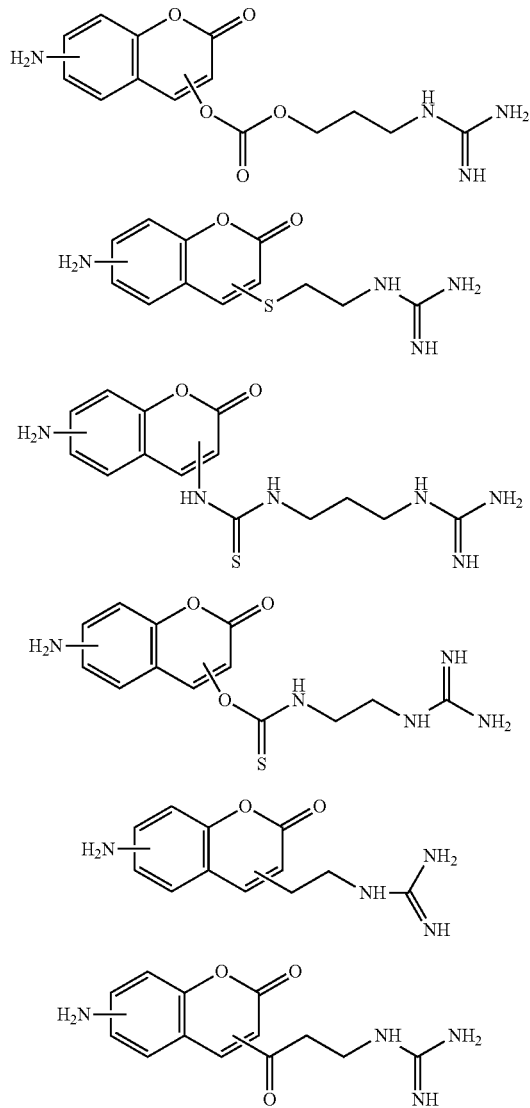

In an embodiment, provided herein are compounds of Formula III, IIIA, IIIB, IIIC, IIID, IIIE, IIIF or IIIG wherein $R^1$ is hydrogen. In an embodiment, provided herein are compounds of Formula III, IIIA, IIIB, IIIC, HID, IIIE, IIIF or IIIG wherein $R^2$ is hydrogen.

In an embodiment, provided herein are compounds of Formula III, IIIA, IIIB, IIIC, IIID, IIIE, IIIF or IIIG wherein $R^1$ and $R^2$ are hydrogen.

Methods for tagging, derivatizing or conjugating glycans and other biomolecules containing at least one ketone group or an aldehyde group with a compound of Formula III, IIIA, IIIB, IIIC, IIID, IIIE, IIIF or IIIG or a compound of Table B by reductive amination reaction are also provided. The reaction between a compound of Formula III and an aldehyde containing biomolecule, such as a glycan can be conducted under conditions that facilitate reductive amination in the presence of a reducing agent selected from sodium cyanoborohydride or sodium triacetoxyborohydride. The reaction can be carried out in a solution or suspension of a compound of Formula III, IIIA, IIIB, IIIC, IIID, IIIE, IIIF or IIIG or a compound of Table B in an acidic media, for example in citric acid or acetic acid, and mixing with a solution or suspension of a reducing agent such as cyanoborohydride or sodium triacetoxyborohydride in an organic solvent, for example, tetrohydrofuran or dimethylsulfoxide.

Further provided are methods for analyzing a biomolecule containing an aldehyde group, such as a glycan, in a sample containing at least one biomolecule, such as a glycan, by means of liquid chromatography and mass spectrometry. The analytical method comprises the steps of labeling the biomolecule, such as a glycan, in the sample by reacting with a compound of Formula III, IIIA, IIIB, IIIC, IIID, IIIE, IIIF or IIIG or a compound of Table B for a time and under conditions suitable to facilitate the labeling through reductive amination; and subjecting the labeled conjugate to liquid chromatography and mass spectrometry.

Analytical kits for assaying biomolecules, such as glycans, are provided where the kits comprise (i) a labeling module comprising a compound of Formula III and salts and solvate thereof; and optionally one or more of the following:

(i) a deglycosylation module comprising one or more endoglycosidases, a buffer, and one or more surfactants, or one or more compounds that can perform a chemical release of glycoprotein; and (ii) a separation device for clean-up such as a solid phase extraction device or a centrifugal filtration device or the like.

Biomolecules, such as glycans, can be conjugated to MS active fluorescent compounds of Formula III and salts or solvates thereof. The following schematic shows the tagging of a glycan using a compound of Formula III through reductive amination:

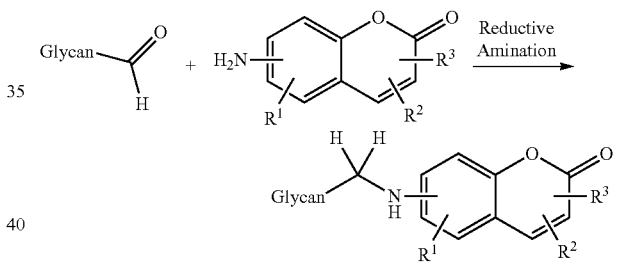

wherein FL $R^1$, $R^2$ and $R^3$ are as described above.

Hence, the methods of tagging glycans, with MS active fluorescent compounds of Formula III, as well as conjugates resulting therefrom are provided.

Naphthalene Based MS Active Fluorescence Tagging Compounds

The MS active, fluorescence tagging compounds can be a naphthalene derivative of Formula IV:

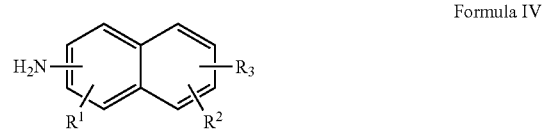

Formula IV wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

R³ is

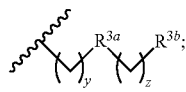

R³ᵃ is selected from ester, amide, amine, oxygen, urea, carbamate, carbonate, sulfur, thiourea, thiocarbamate, alkyl or carbonyl;
R³ᵇ is

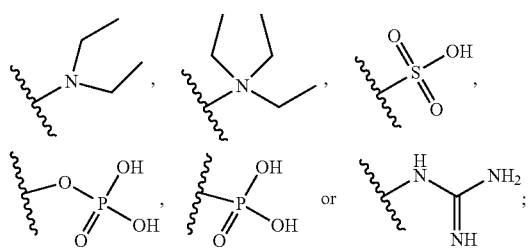

y=0-12;
z=1-12;
and salts or solvates thereof.

In an embodiment, provided herein are compounds of Formula IV, with the proviso that when y is two, R³ᵃ is other than ester.

In an embodiment, provided herein are compounds of Formula IV, with the proviso that when y is zero, R³ᵃ is oxygen, amide or ester, and z is two or three, R³ᵇ is other than

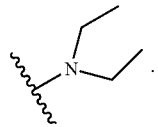 [SMILES: *N(CC)CC]

In an embodiment, provided herein are compounds of Formula IV, with the proviso that when y is zero and R³ᵃ is oxygen or amine, and z is three, R³ᵇ is other than —S(O)₃H.

In an embodiment, provided herein are compounds of Formula IVA:

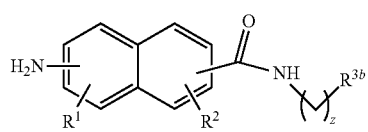

Formula IVA wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

R³ᵇ is

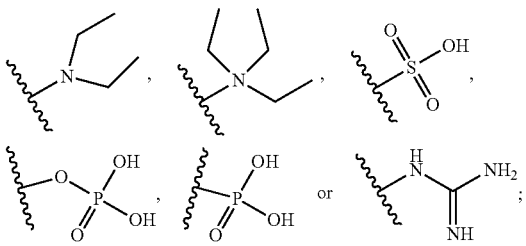

z=1-12;
and salts or solvates thereof.

In an embodiment, provided herein are compounds of Formula IVB:

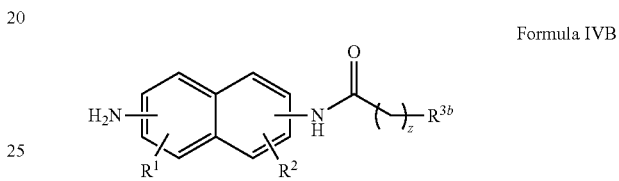

Formula IVB wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
R³ᵇ is

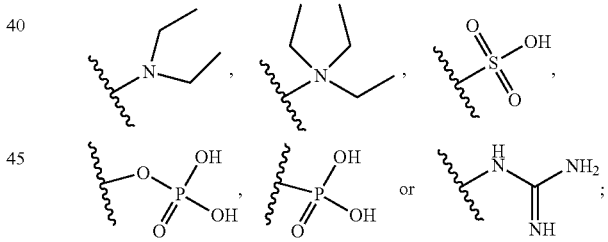

z=1-12;
and salts or solvates thereof.

In an embodiment, provided are compounds of Formula IVC:

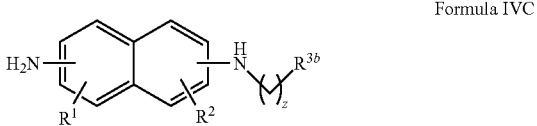

Formula IVC wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

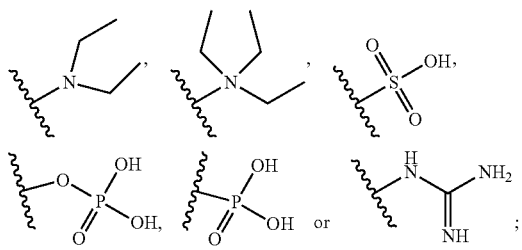

z=1-12;
and salts or solvates thereof.

In an embodiment, provided are compounds of Formula IVC with the proviso that when z is two, $R^{3b}$ is other than

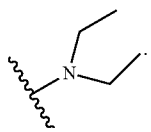

In an embodiment, provided are compounds of Formula IVD:

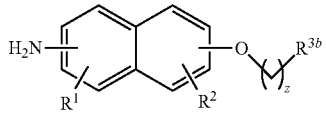

Formula IVD wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

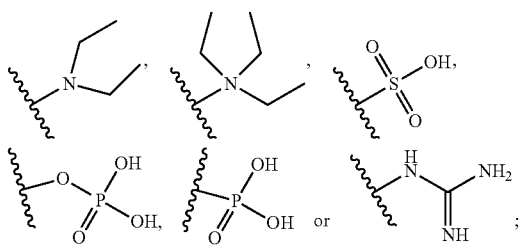

z=1-12;
and salts or solvates thereof.

In an embodiment, provided are compounds of Formula IVD with the proviso that when z is two, $R^{3b}$ is other than

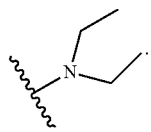 [SMILES: *N(CC)CC]

In an embodiment, provided are compounds of Formula IVE:

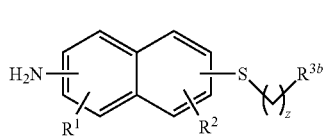

Formula IVE wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

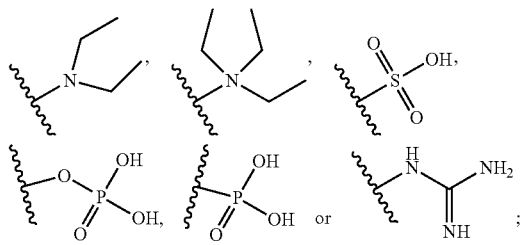

z=1-12;
and salts or solvates thereof.

In an embodiment, provided are compounds of structural Formula IVE with the proviso that when z is two, $R^{3b}$ is other than

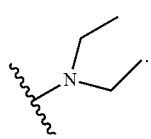 [SMILES: *N(CC)CC]

In an embodiment, provided are compounds of Formula IVF:

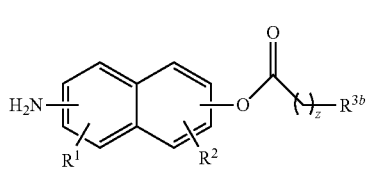

Formula IVF wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

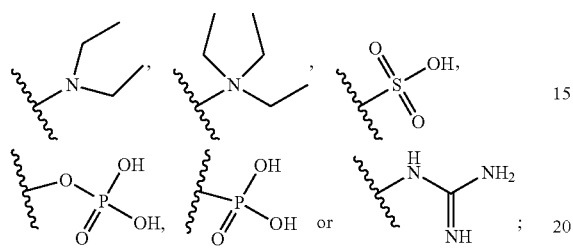

z=1-12;
and salts or solvates thereof.

In an embodiment, provided are compounds of Formula IVG:

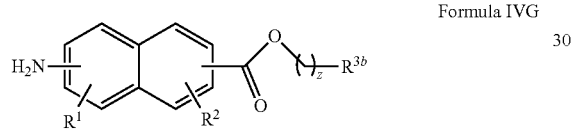

Formula IVG wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R_{3b}$ is

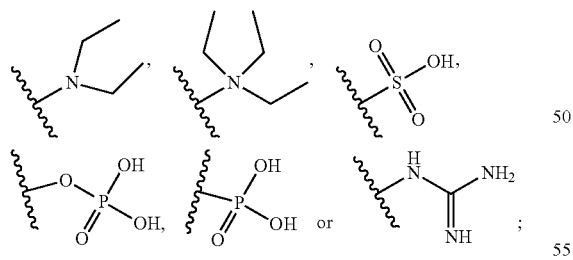

z=1-12;
and salts or solvates thereof.

In addition, provided below are exemplary compounds (Table C) of the structural Formulas IV, IVA, IVB, IVC, IVD, IVE, IVF or IVG which can be useful for fluorescent labeling of glycans and subsequent analysis by means of liquid chromatography and mass spectrometry. The compounds of structural formulas IV, IVA, IVB, IVC, IVD, IVE, IVF or IVG can be optionally substituted with any group that does not substantially reduce the fluorescence of the compound.

TABLE C

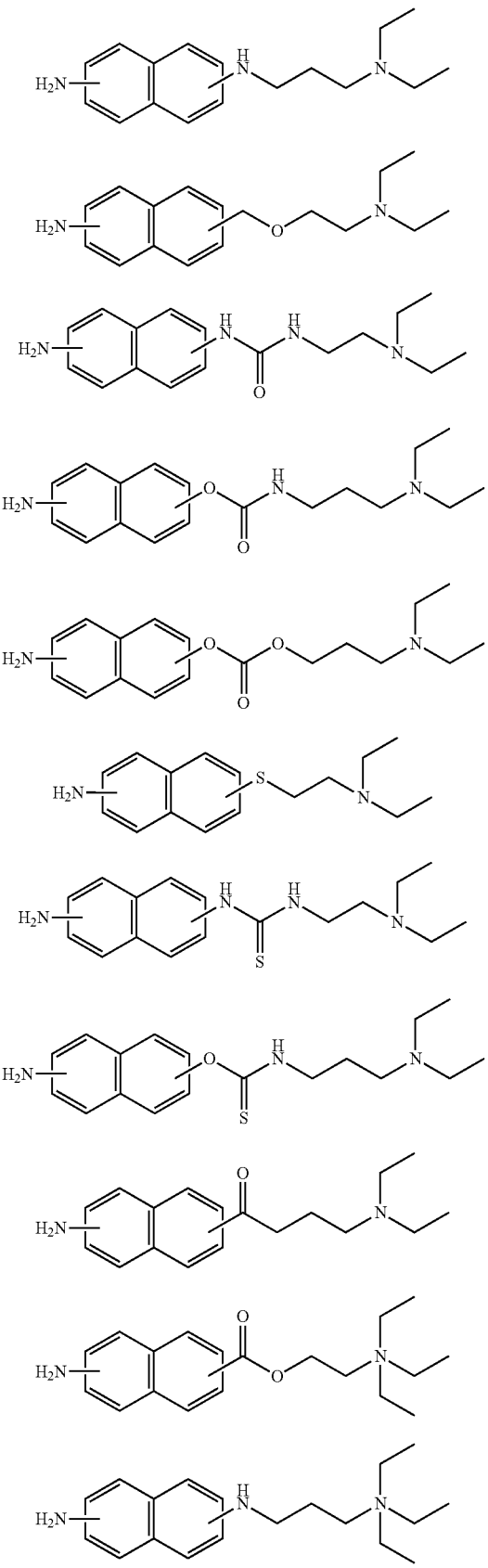

TABLE C-continued
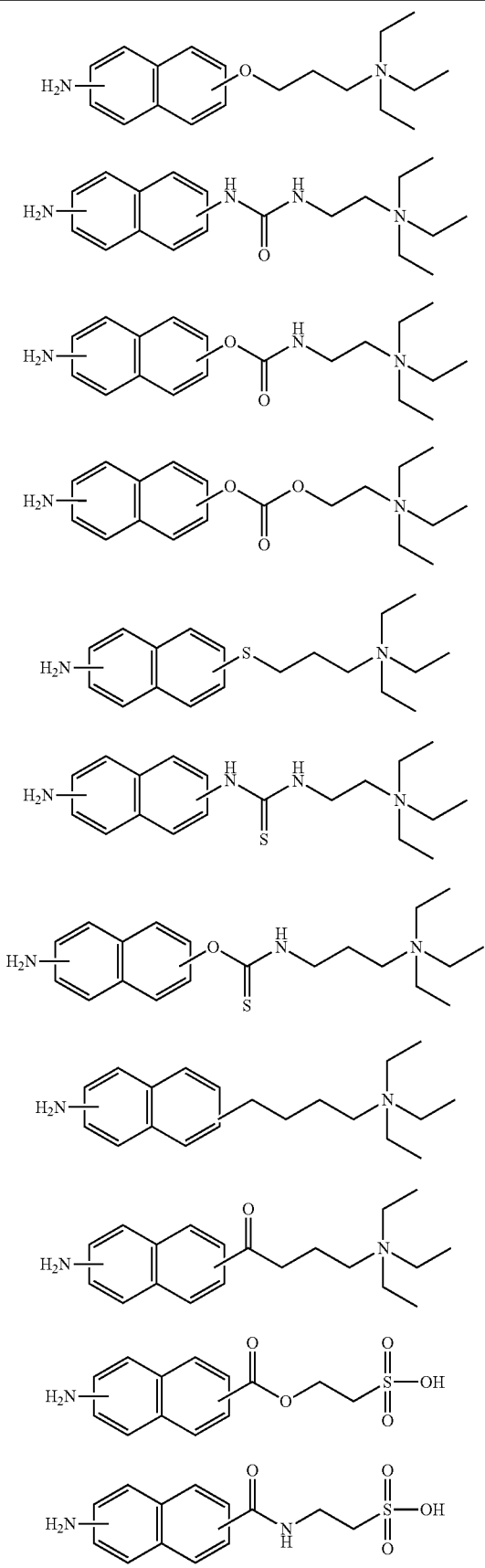
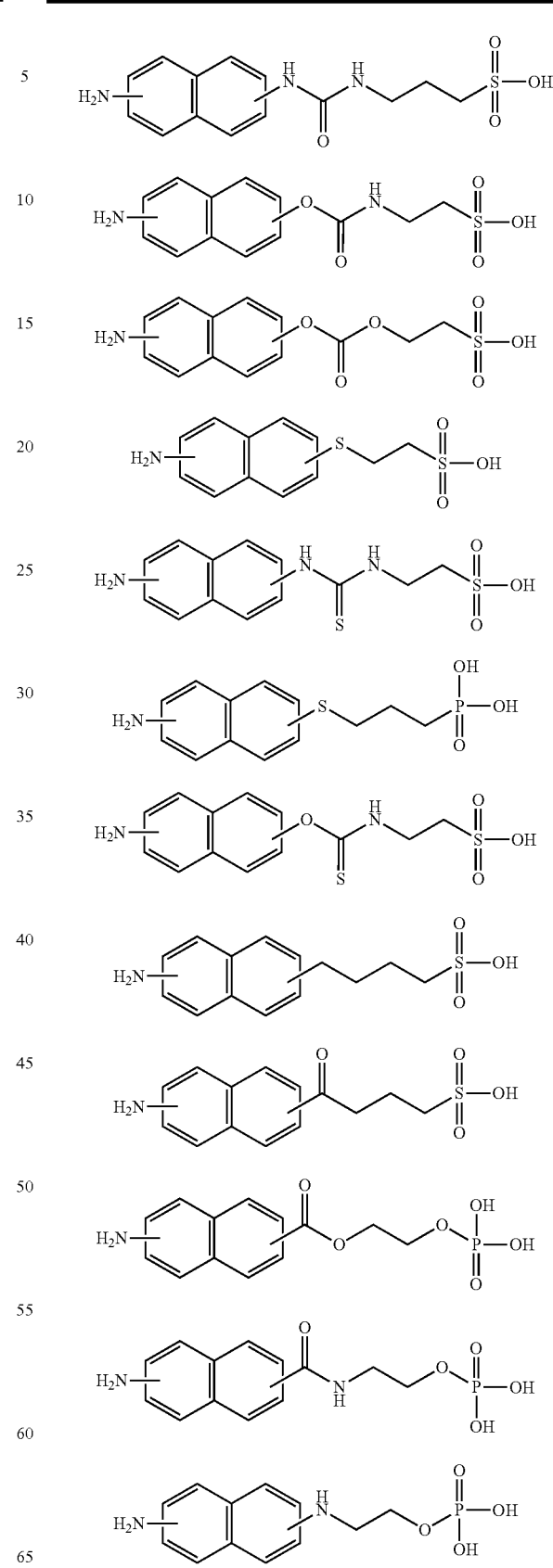

TABLE C-continued

TABLE C-continued

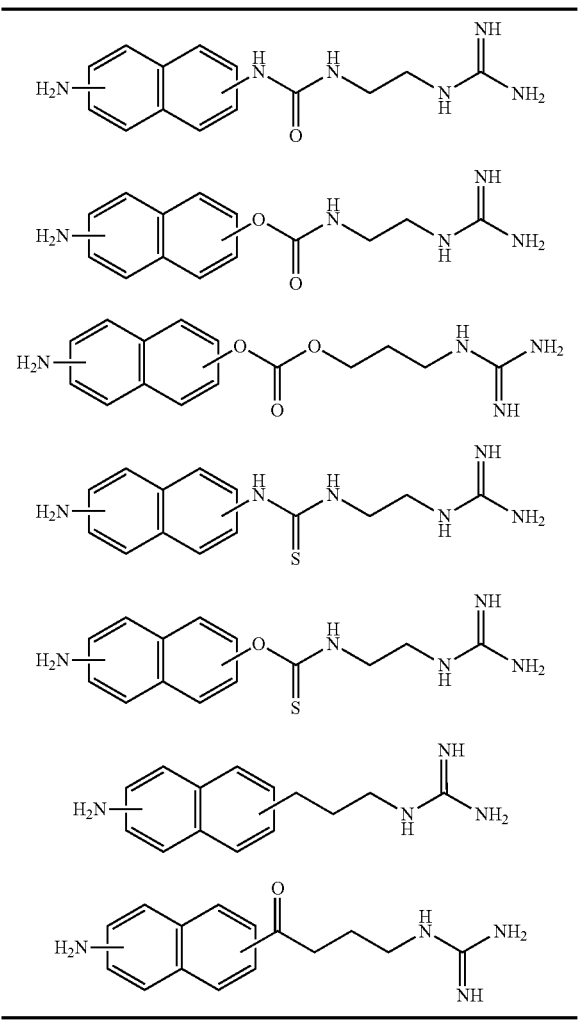

In an embodiment, provided herein are compounds of Formula IV, IVA, IVB, IVC, IVD, IVE, IVF or IVG wherein $R^1$ is hydrogen. In an embodiment, provided herein are compounds of Formula IV, IVA, IVB, IVC, IVD, IVE, IVF or IVG wherein $R^2$ is hydrogen. In an embodiment, provided herein are compounds of Formula IV, IVA, IVB, IVC, IVD, IVE, IVF or IVG wherein $R^1$ and $R^2$ are hydrogen.

The methods for tagging, derivatizing or conjugating glycans and other biomolecules containing at least one ketone group or an aldehyde group are also provided with a compound of Formula IV, IVA, IVB, IVC, IVD, IVE, IVF or IVG by reductive amination reaction are also provided. The reaction between a compound of Formula IV and an aldehyde containing biomolecule, such as a glycan can be conducted under conditions that facilitate reductive amination in the presence of a reducing agent, such as sodium cyanoborohydride or sodium triacetoxyborohydride. The reaction can be carried out in a solution or suspension of a compound of Formula IV, IVA, IVB, IVC, IVD, IVE, IVF or IVG in an acidic media, for example in citric acid or acetic acid, and mixing with a solution or suspension of a reducing agent such as cyanoborohydride or sodium triacetoxyborohydride in an organic solvent, for example, tetrahydrofuran or dimethylsulfoxide.

Methods for analyzing a biomolecule containing an aldehyde group, such as a glycan, in a sample containing at least one biomolecule, such as a glycan, by means of liquid chromatography and mass spectrometry are also provided. The analytical methods comprise the steps of labeling the biomolecule, such as a glycan, in the sample by reacting with a compound of Formula IV, IVA, IVB, IVC, IVD, IVE, IVF or IVG for a time and under conditions suitable to facilitate the labeling through reductive amination; and subjecting the labeled conjugate to liquid chromatography and mass spectrometry.

Analytical kits for assaying biomolecules, such as glycans, can include (i) a labeling module comprising a compound of Formula IV and salts and solvate thereof; and optionally one or more of the following:

(i) a deglycosylation module comprising one or more endoglycosidases, a buffer, and one or more surfactants, or one or more compounds that can perform a chemical release of glycoprotein; and (ii) a separation device for clean-up such as a solid phase extraction device or a centrifugal filtration device or the like.

Glycans can be conjugated to MS active fluorescent compounds of Formula IV and salts or solvates thereof. The following schematic shows the tagging of a glycan using a compound of Formula IV through reductive amination:

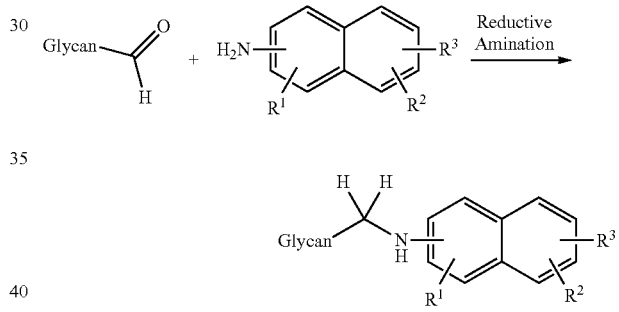

Wherein FL $R^1$, $R^2$ and $R^3$ are as described above.

Therefore, methods of tagging glycans with MS active fluorescent compounds of Formula IV, as well as conjugates resulting therefrom are provided herein.

Rhodamine Based MS Active Fluorescence Tagging Compounds

The MS active, fluorescence tagging compounds can be a rhodamine derivative of Formula V, VI, VII, VIII or IX:

Formula V

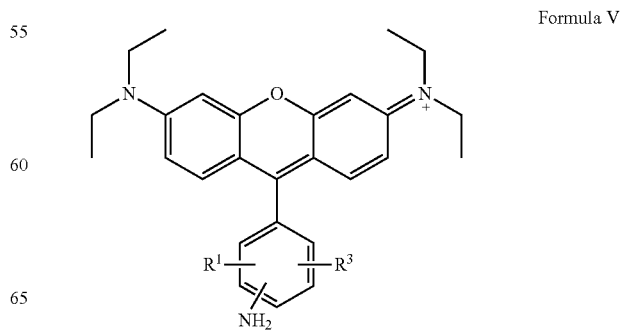

-continued

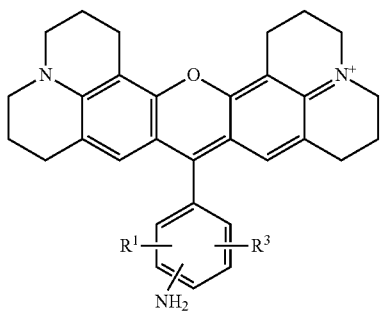

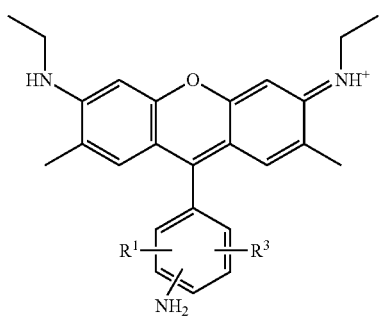

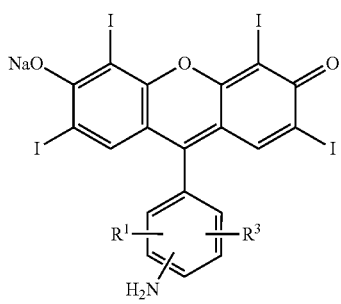

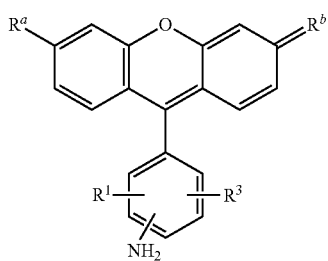

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^3$ is

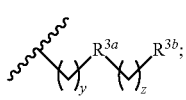

$R^{3a}$ is selected from ester, amide, amine, oxygen, urea, carbamate, carbonate, sulfur, thiourea, thiocarbamate, alkyl or carbonyl;

$R^{3b}$ is

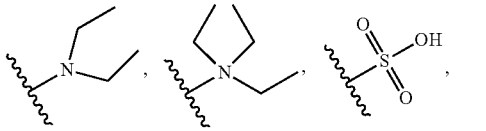

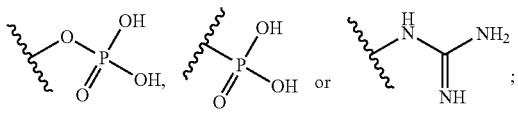

$y=0-12$;
$z=1-12$;
$R^a$ is selected from

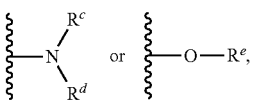

$R^b$ is OXO or;

$R^c$, $R^d$, $R^e$, $R^f$ and $R^g$ are independently selected from hydrogen and optionally substituted alkyl; and salts or solvates thereof.

In an embodiment, provided herein are compounds of Formula VA, VIA, VIIA, VIIIA or IXA:

Formula VA

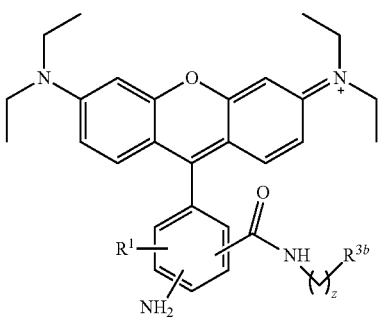

Formula VIA

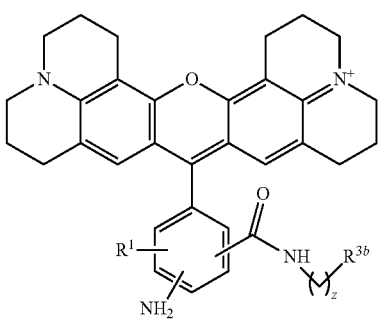

-continued

Formula VIIA

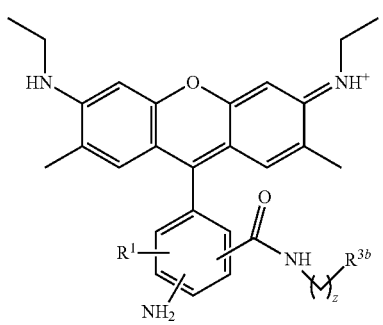

Formula VIIIA

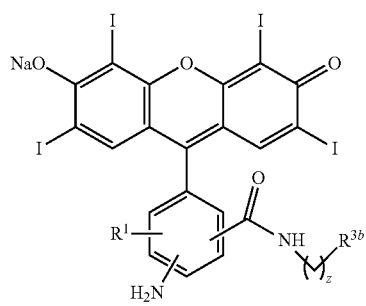

Formula IXA

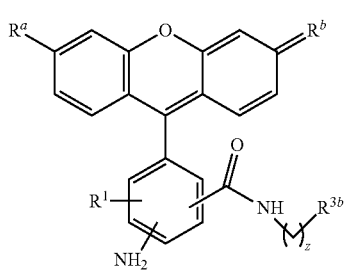

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

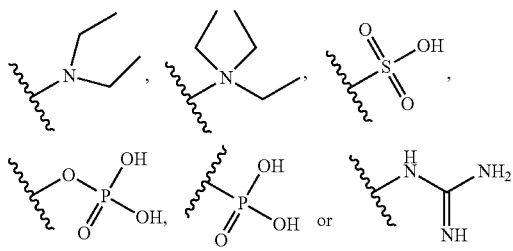

z=1-12; $R^a$ is selected from

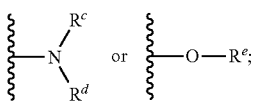

$R^b$ is oxo or

$R^c$, $R^d$, $R^e$, $R^f$ and $R^g$ are independently selected from hydrogen and optionally substituted alkyl; and salts or solvates thereof.

In an embodiment, provided herein are compounds of Formula VB, VIB, VIIB, VIIIB or IXB:

Formula VB

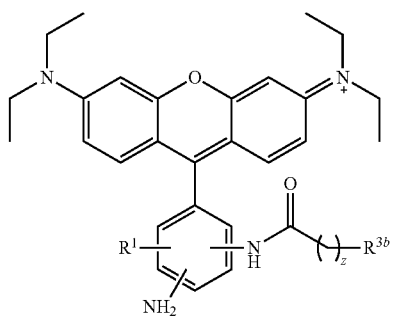

Formula VIB

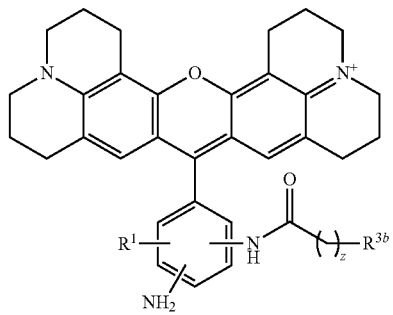

Formula VIIB

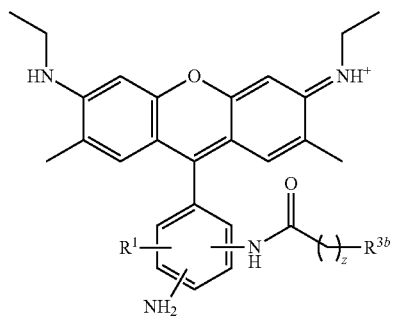

Formula VIIIB

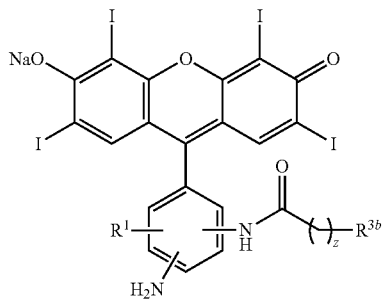

-continued

Formula IXB

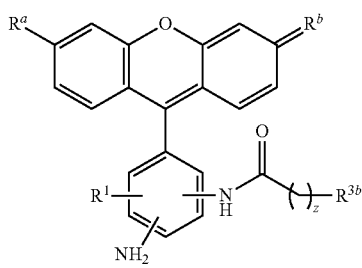

wherein each R₁ and R₂ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

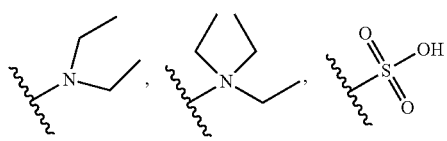

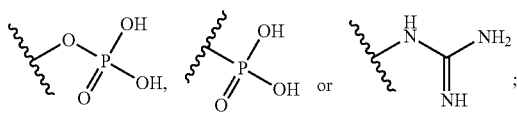

z=1-12;

$R^a$ is selected from

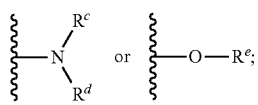

$R^b$ is oxo or

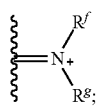

$R^c$, $R^d$, $R^e$, $R^f$ and $R^g$ are independently selected from hydrogen and optionally substituted alkyl; and salts or solvates thereof.

In yet another embodiment, provided are compounds of Formula VC, VIC, VIIC, VIIIC or IXC:

Formula VC

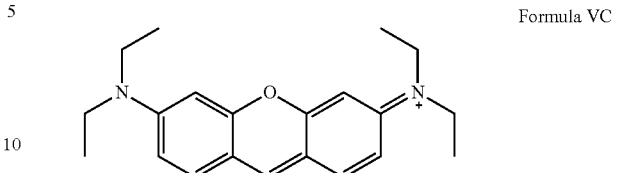

Formula VIC

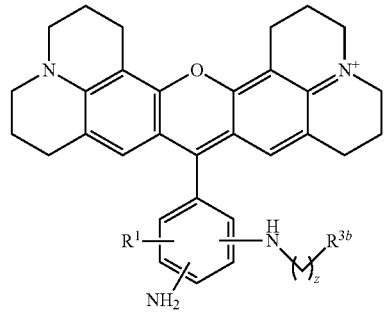

Formula VIIC

Formula VIIIC

Formula IXC

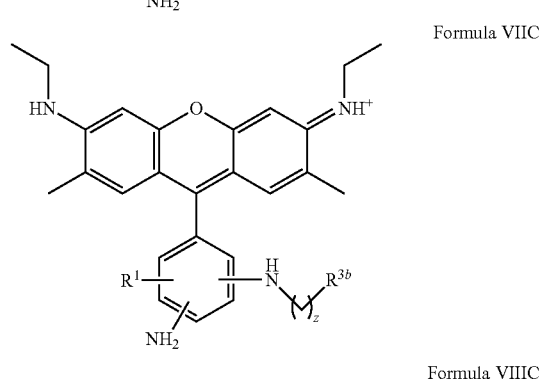

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkyl sulfinyl, lower alkyl sulfonyl, sulfonate, sulfonic acid, $N_3$, SH, $SCH_3$, $C(O)CH_3$, $CO_2CH_3$ and $CO_2H$;

$R^{3b}$ is

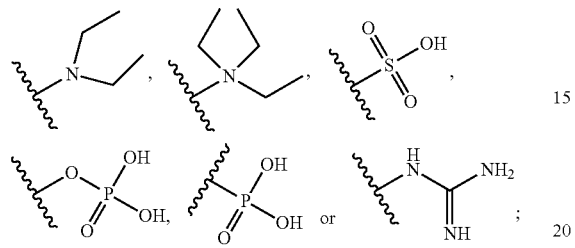

z=1-12;

and salts or solvates thereof.

In an embodiment, provided herein are compounds of Formula VD, VID, VIID, VIIID or IXD:

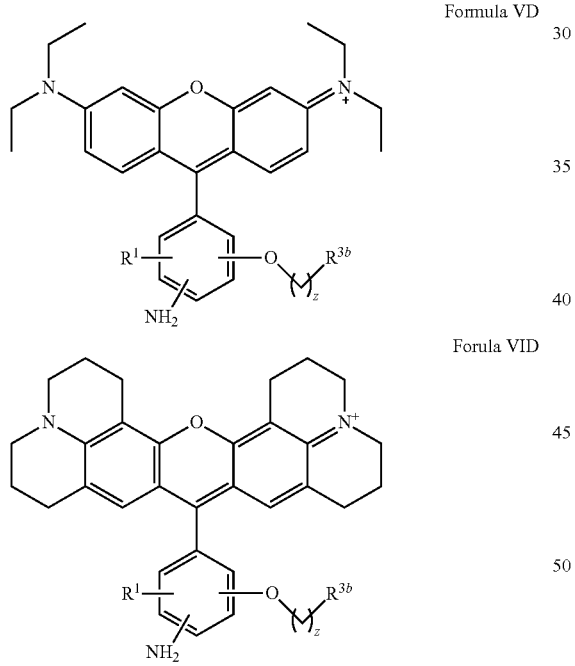

Formula VD

Forula VID

Formula VIID

Formula VIIID

Formula IXD

In an embodiment, provided herein are compounds of Formula VE, VIE, VIIE, VIIIE or IXE:

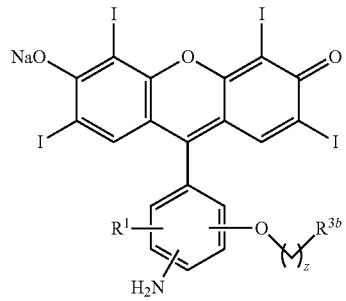

Formula VE

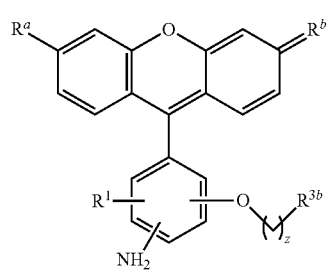

Formula IXD

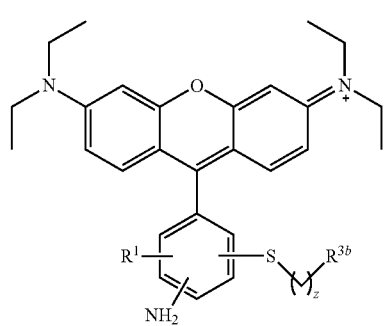

Forula VIE

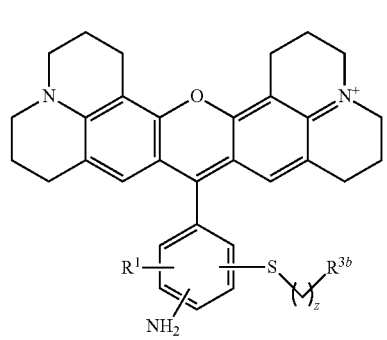

-continued

Formula VIIE

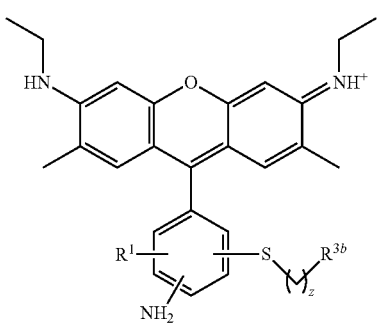

Formula VIIIE

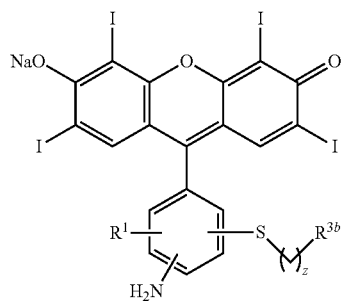

Formula IXE

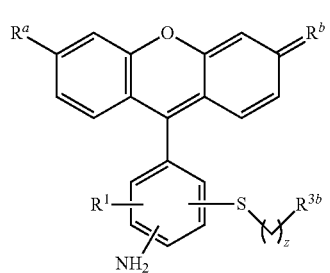

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

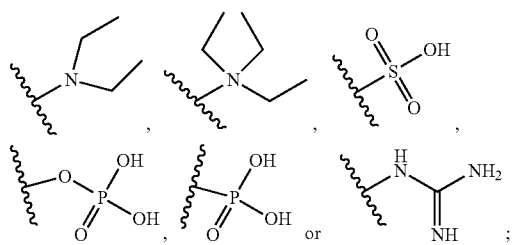

$z = 1-12$;

and salts or solvates thereof.

In addition, provided below are exemplary compounds (Table D) of the structural Formulas V, VI, VII, VIII and IX which can be useful for fluorescent labeling of glycans and subsequent analysis by means of liquid chromatography and mass spectrometry. The compounds of structural Formulas V, VI, VII, VIII and IX can be optionally substituted with any group that does not substantially reduce the fluorescence of the compound.

TABLE D

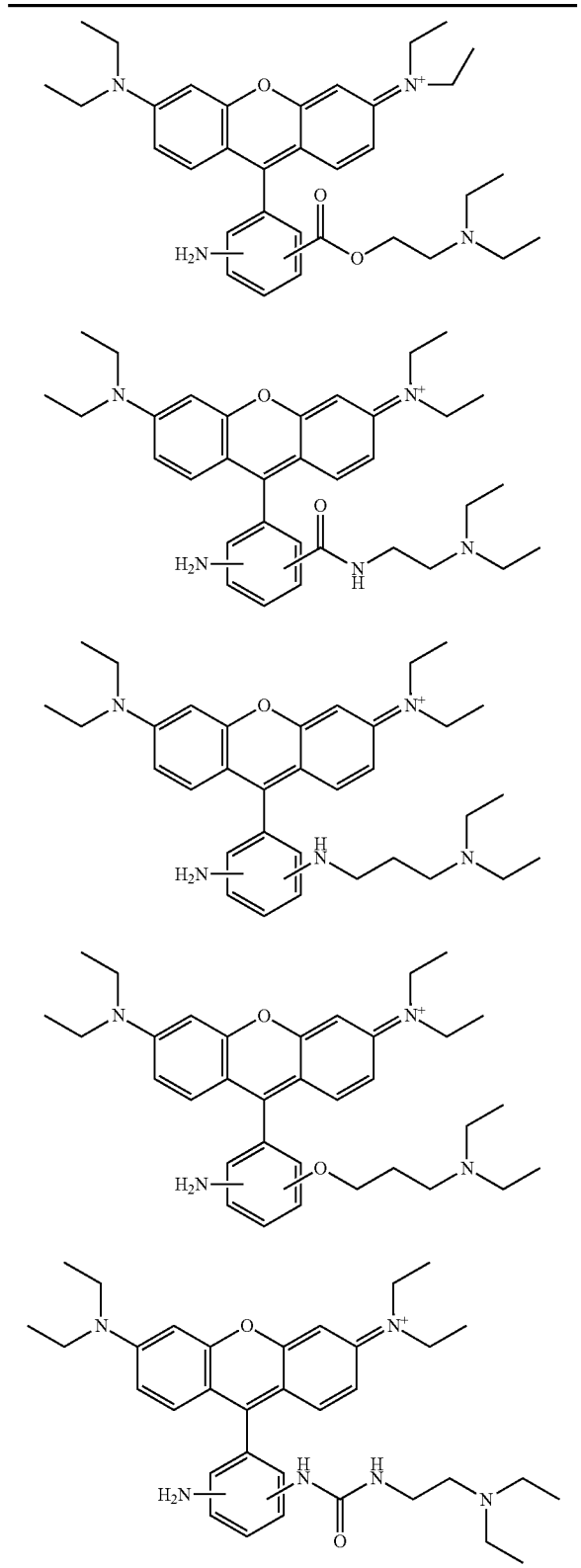

TABLE D-continued
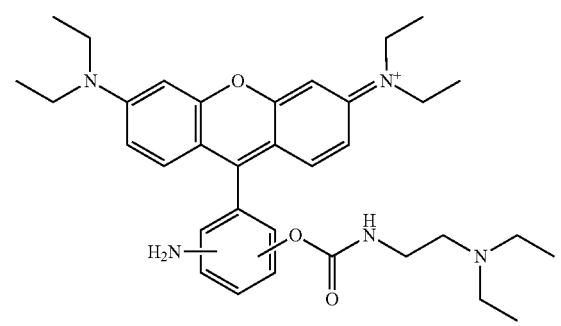
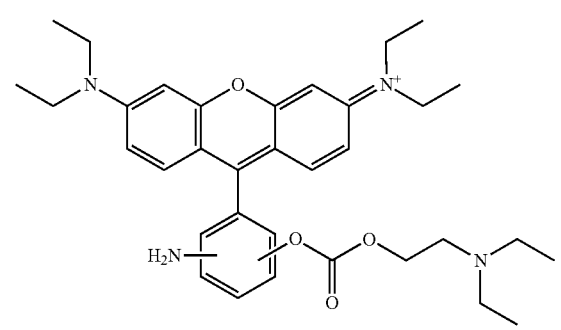
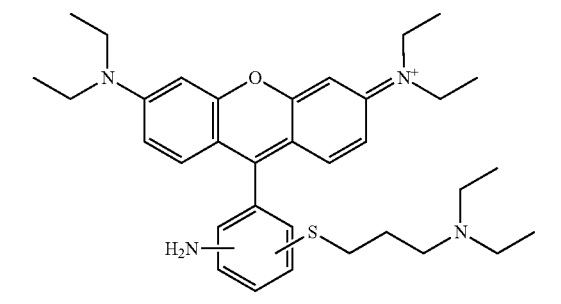
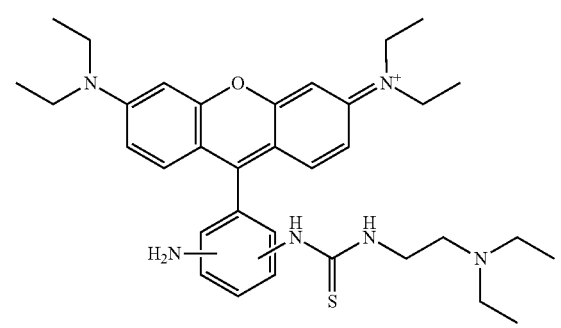
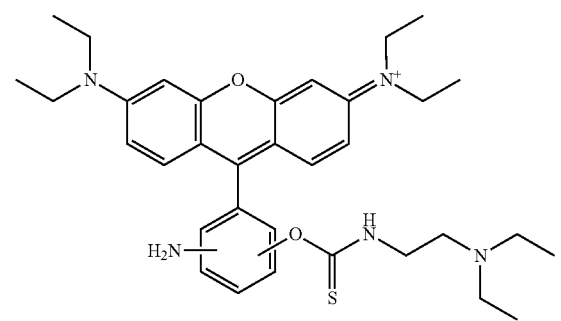
TABLE D-continued
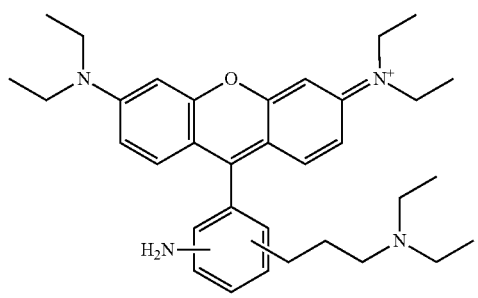
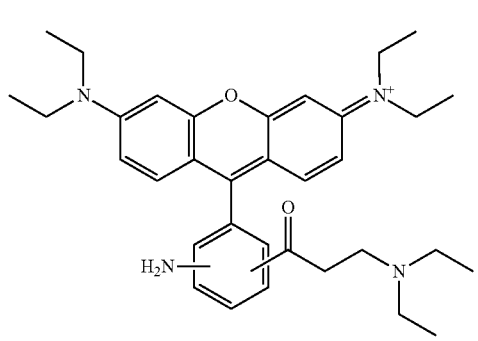
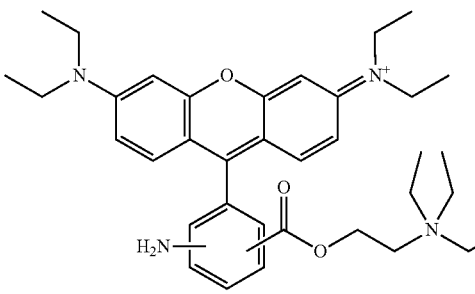
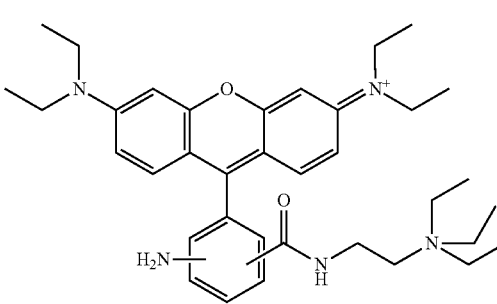
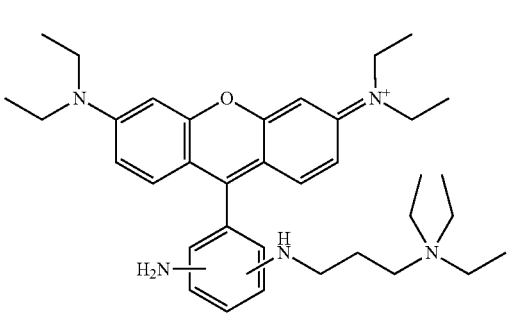

TABLE D-continued
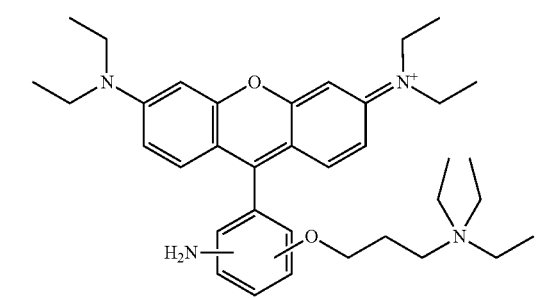
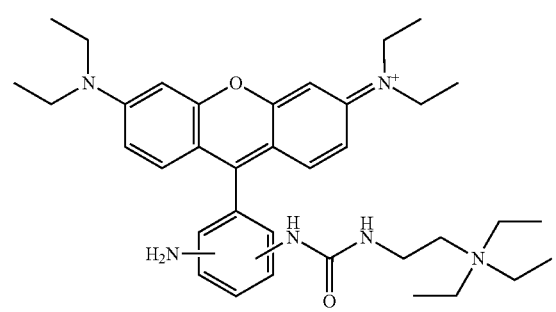
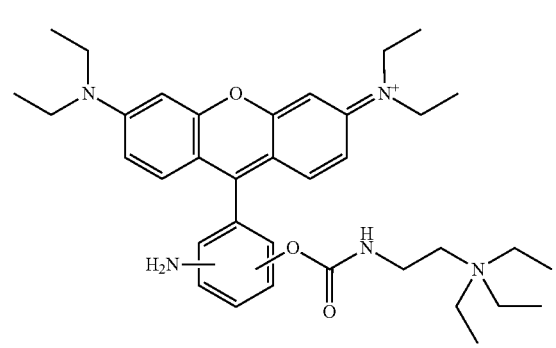
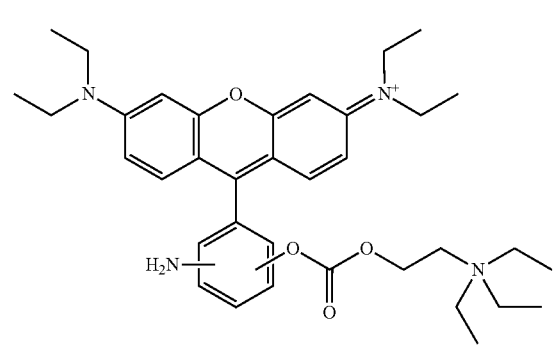
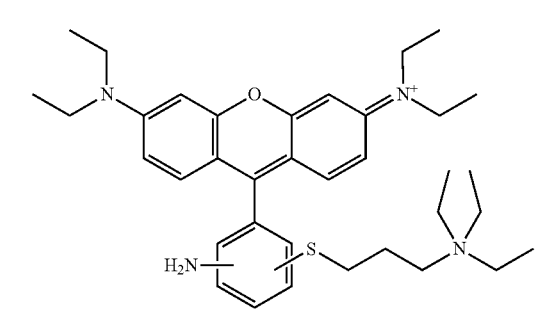
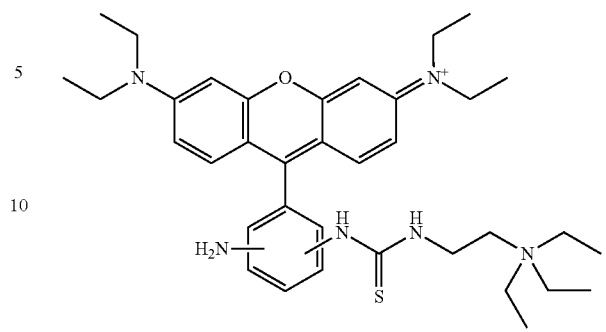
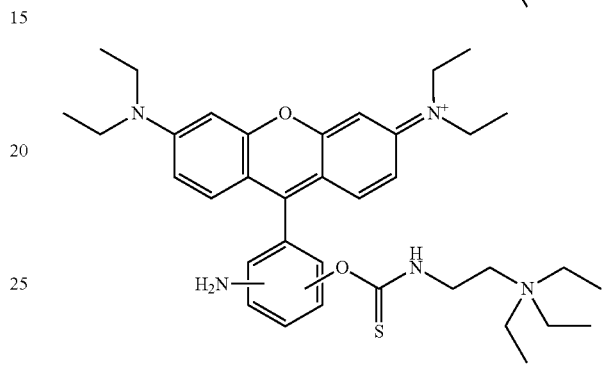
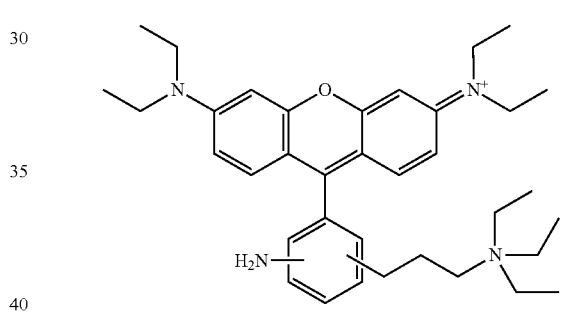
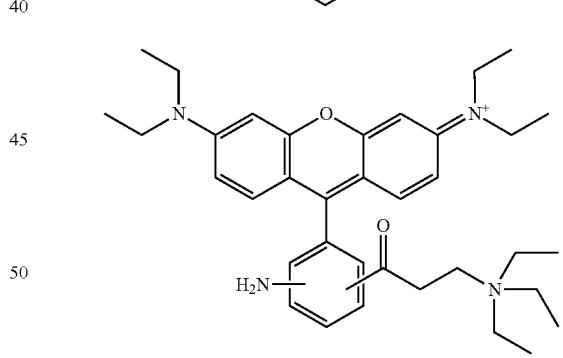
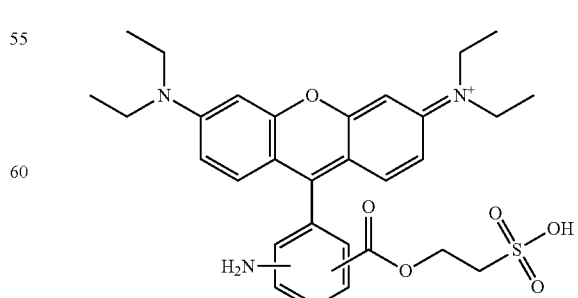

TABLE D-continued
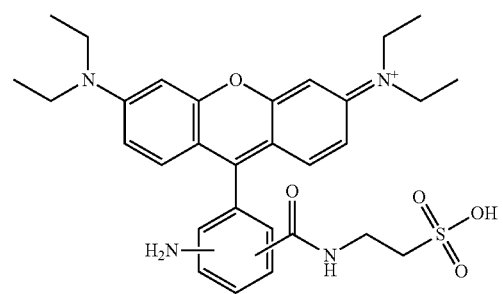
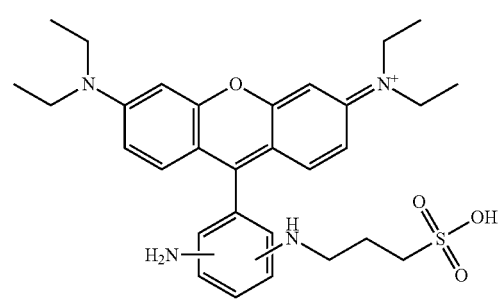
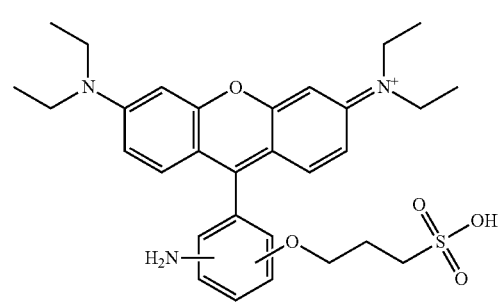
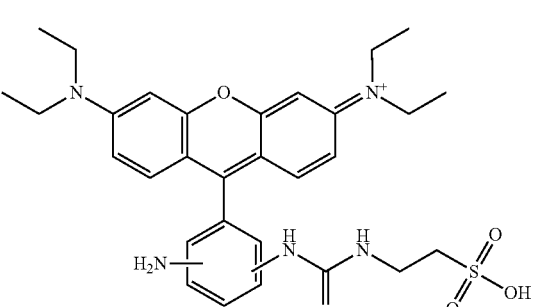
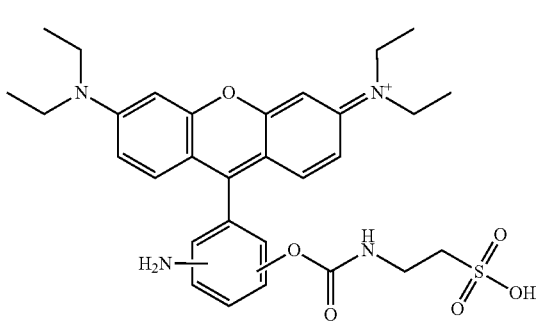
TABLE D-continued
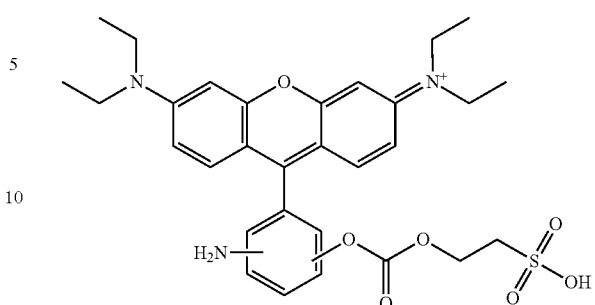
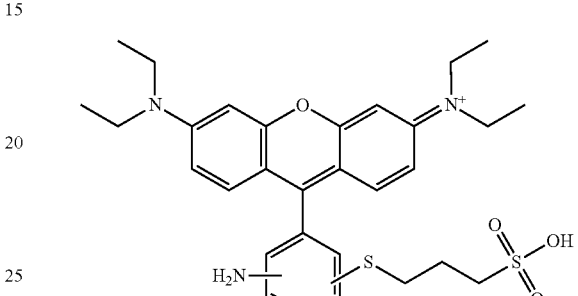
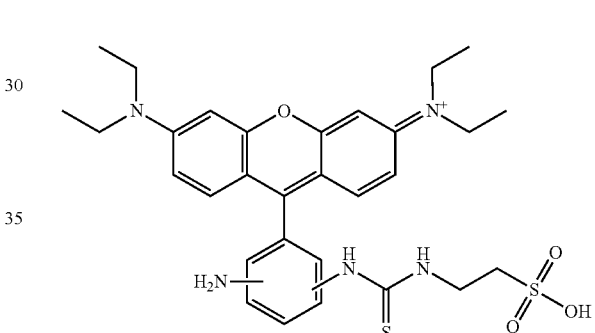
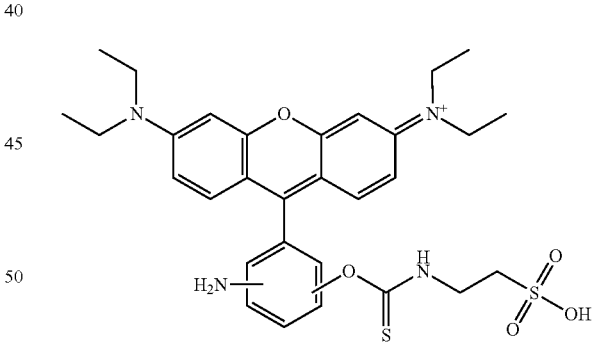
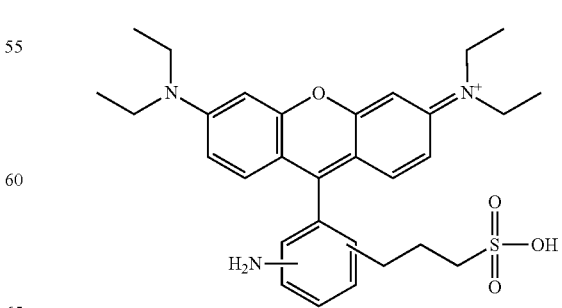

TABLE D-continued
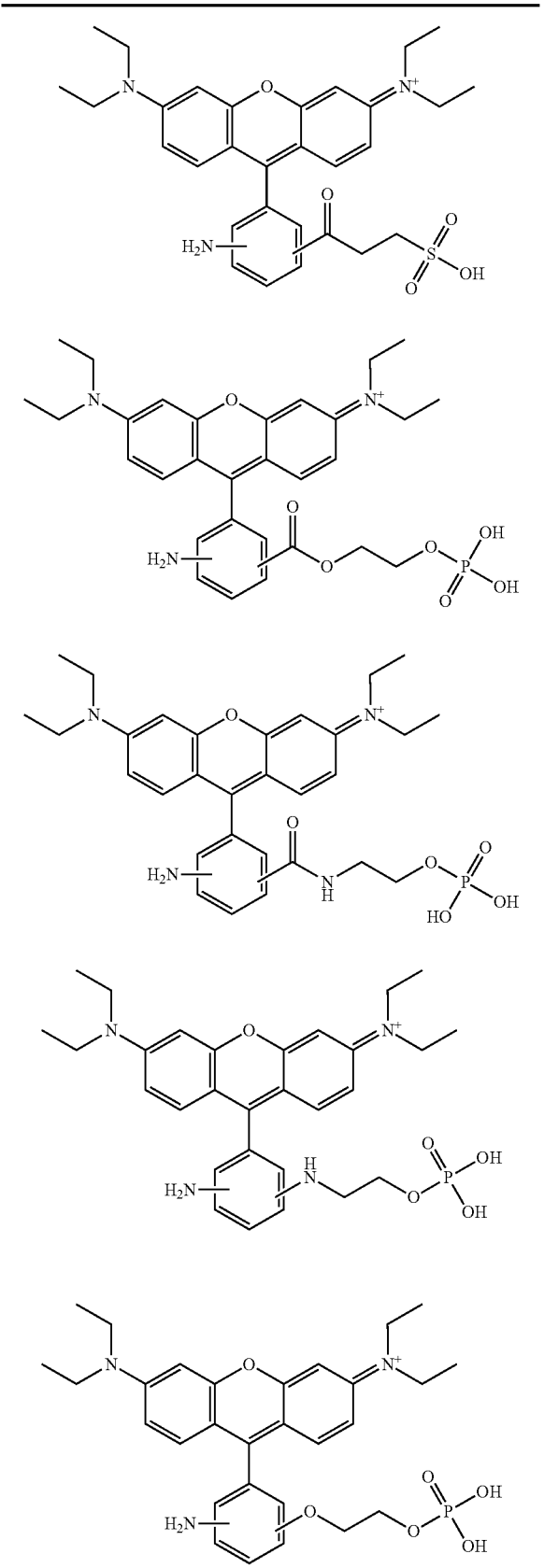
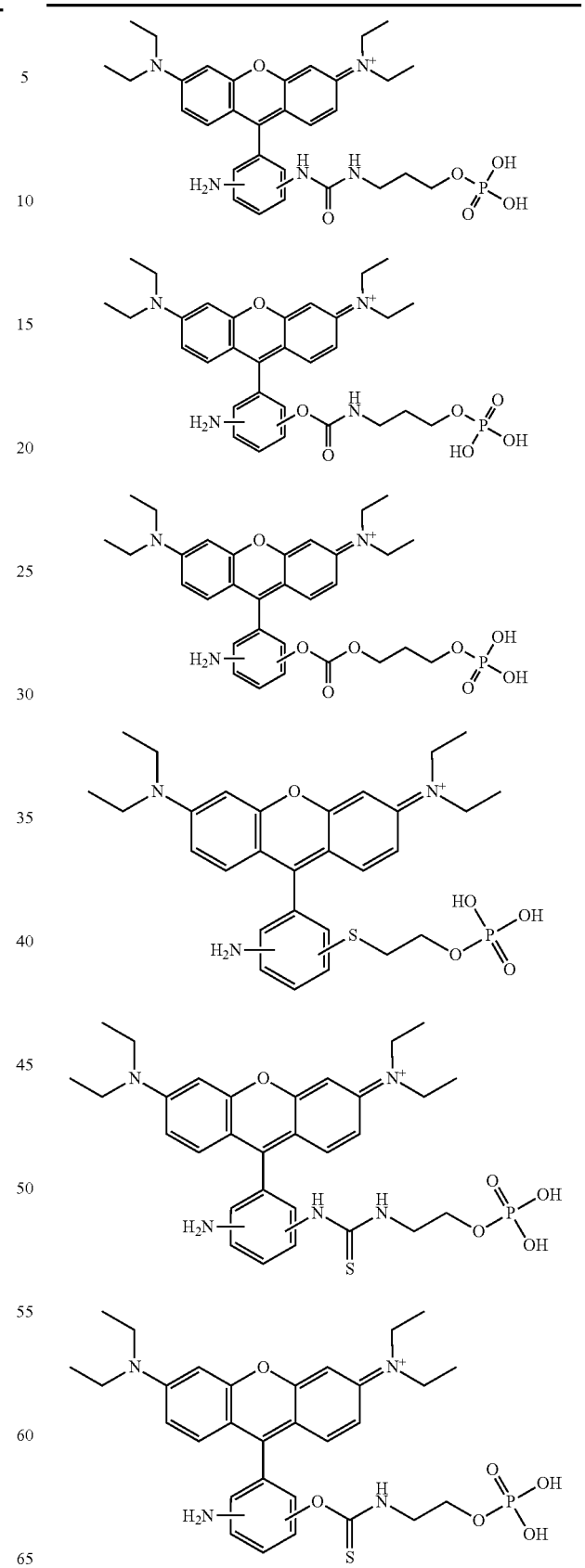

TABLE D-continued
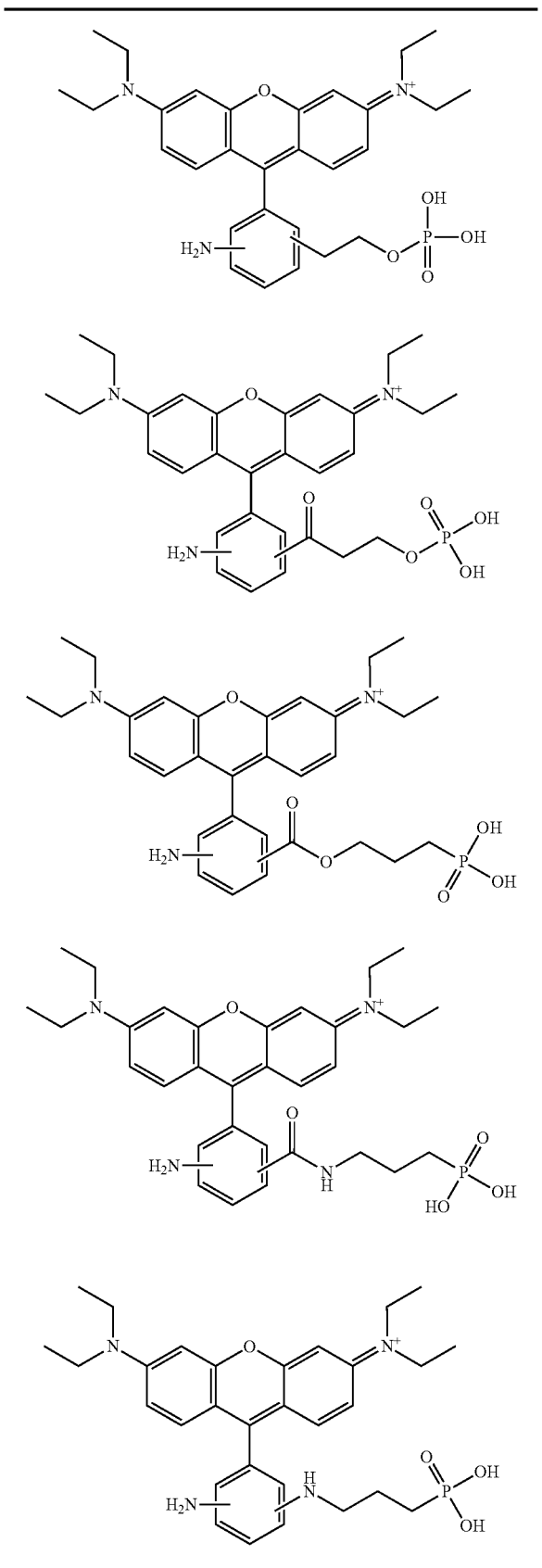
TABLE D-continued
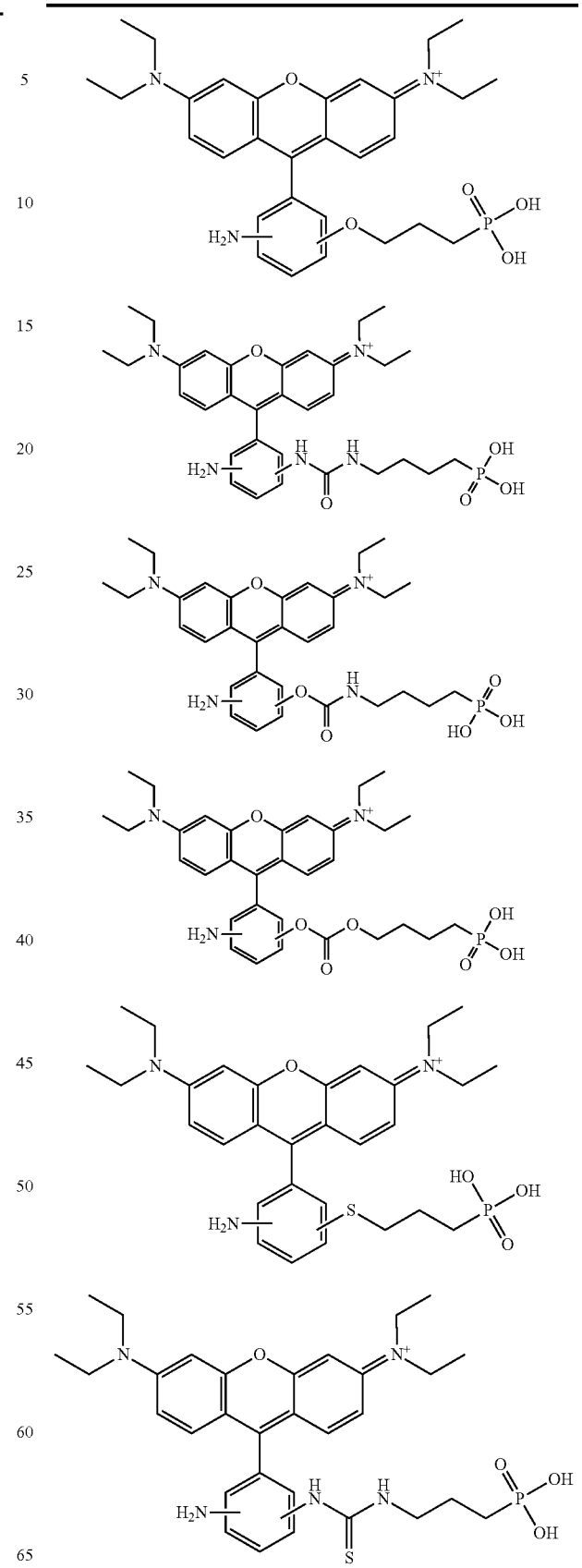

TABLE D-continued
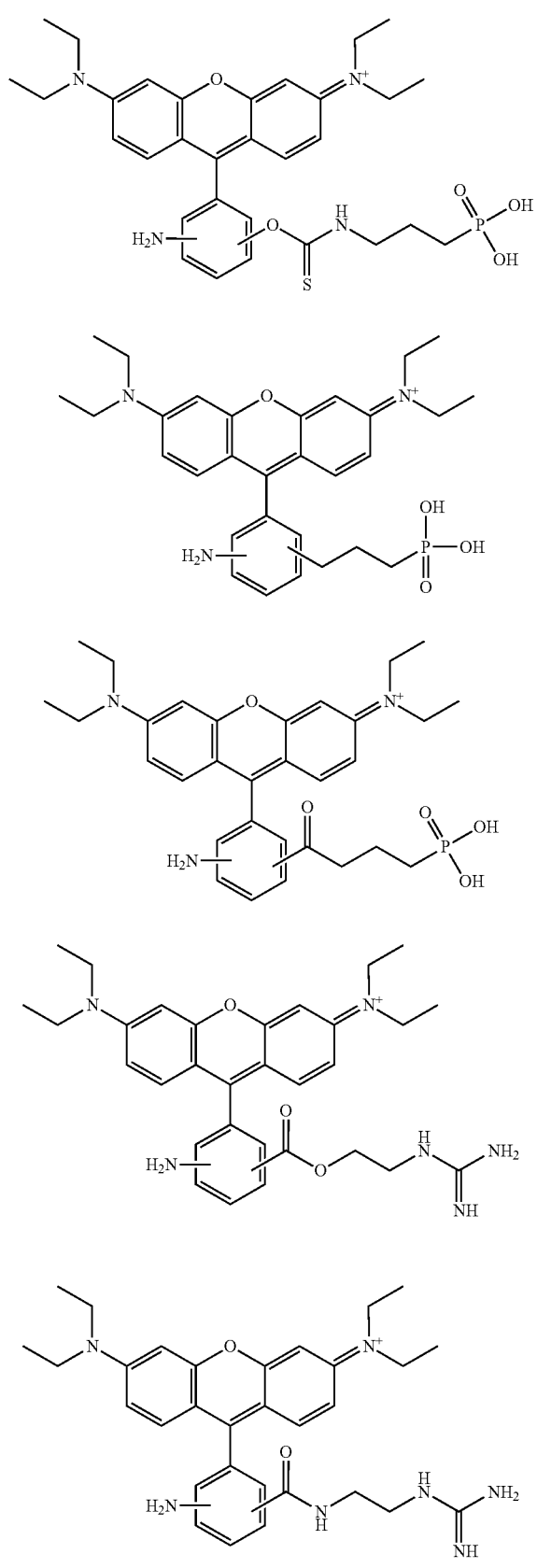
TABLE D-continued
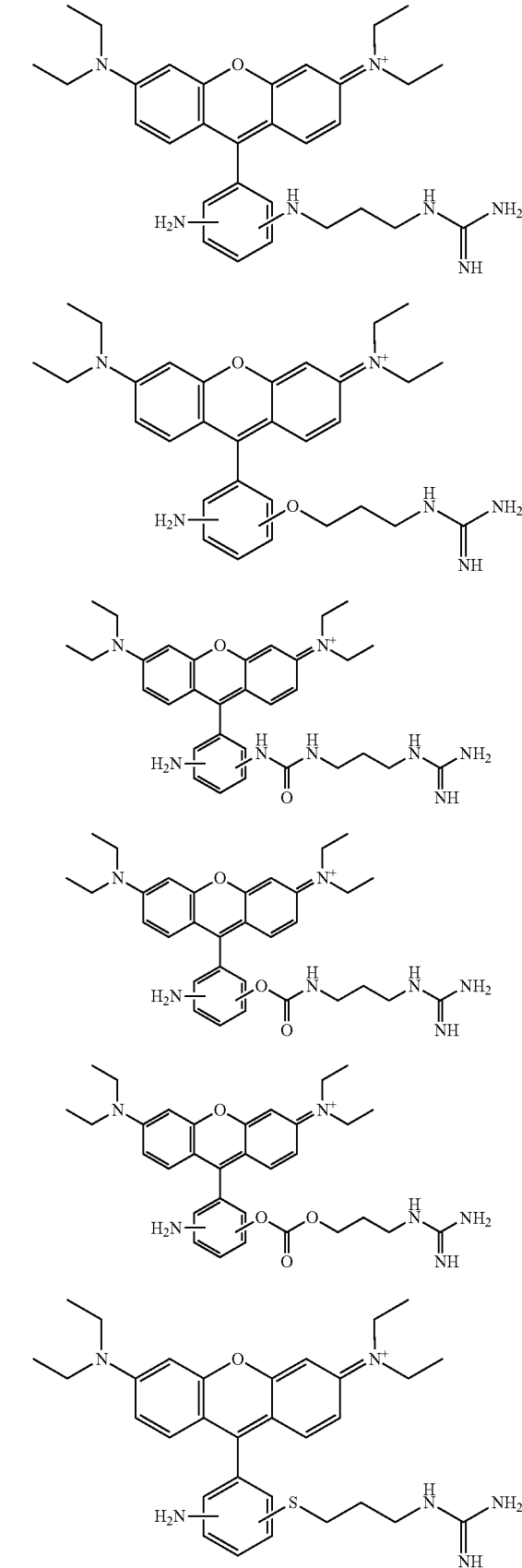

TABLE D-continued

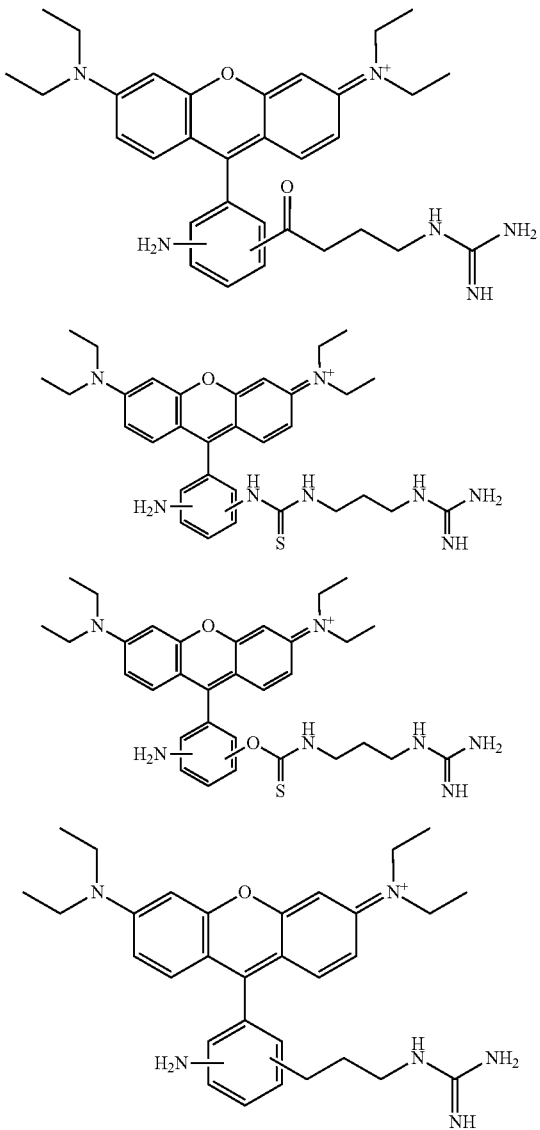

The compounds of Formula V, VI, VII, VIII or IX are provided wherein $R^1$ is hydrogen. In an embodiment, provided herein are compounds of Formula V, VI, VII, VIII or IX wherein $R^2$ is hydrogen. In an embodiment, provided herein are compounds of Formula V, VI, VII, VIII or IX wherein $R^1$ and $R^2$ are hydrogen.

Methods for tagging, derivatizing or conjugating glycans and other biomolecules containing at least one ketone group or an aldehyde group with a compound of Formula V, VI, VII, VIII or IX or a compound of Table D by reductive amination reaction are provided. The reaction between a compound of Formula V, VI, VII, VIII or IX or a compound of Table D and an aldehyde containing biomolecule, such as a glycan can be conducted under conditions that facilitate reductive amination in the presence of a reducing agent, such as from sodium cyanoborohydride or sodium triacetoxyborohydride. The reaction can be carried out in a solution or suspension of a compound of Formula V, VI, VII, VIII or IX or a compound of Table D in an acidic media, for example in citric acid or acetic acid, and mixing with a solution or suspension of a reducing agent such as cyanoborohydride or sodium triacetoxyborohydride in an organic solvent, for example, tetrohydrofuran or dimethylsulfoxide.

Methods are provided for analyzing a biomolecule containing an aldehyde group, such as a glycan, in a sample containing at least one biomolecule, such as a glycan, by means of liquid chromatography and mass spectrometry. The analytical method comprises the steps of labeling the biomolecule, such as a glycan, in the sample by reacting with a compound of Formula V, VI, VII, VIII or IX or a compound of Table D for a time and under conditions suitable to facilitate the labeling through reductive amination; and subjecting the labeled conjugate to liquid chromatography and mass spectrometry.

Analytical kits for assaying biomolecules, such as glycans, can include (i) a labeling module comprising a compound of Formula VI, VII, VIII, IX or a compound of Table D, and salts and solvate thereof; and optionally one or more of the following:
(i) a deglycosylation module comprising one or more endoglycosidases, a buffer, and one or more surfactants, or one or more compounds that can perform a chemical release of glycoprotein; and
(ii) a separation device for clean-up such as a solid phase extraction device or a centrifugal filtration device or the like.

Glycans conjugated to MS active fluorescent compounds of Formula V, VI, VII, VIII or IX, and salts or solvates thereof are also provided.

Phenyl Based MS Active Fluorescence Tagging Compounds

In another embodiment, analytical kits for assaying glycans and other biomolecules include (i) a labeling module comprising a compound of Formula X, XA, XB, XC, XD, XE, XF or XG and salts and solvate thereof; and optionally one or more of the following is provided:
(i) a deglycosylation module comprising one or more endoglycosidases, a buffer, and one or more surfactants, or one or more compounds that can perform a chemical release of glycoprotein; and
(ii) a separation device for clean-up such as a solid phase extraction device or a centrifugal filtration device or the like.

Kits comprising MS active, fluorescence tagging compounds can contain a phenyl derivative of Formula X:

Formula X

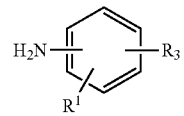

wherein $R_1$ is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^3$ is;

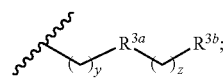

R$^{3a}$ is selected from ester, amide, amine, oxygen, urea, carbamate, carbonate, sulfur, thiourea, thiocarbamate, alkyl or carbonyl;
R$^{3b}$ is

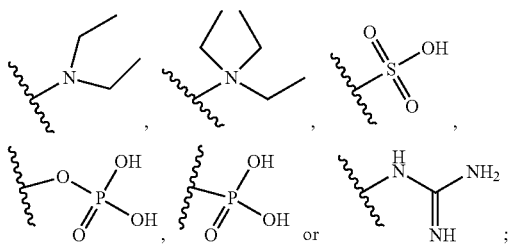

y=0-12;
z=1-12;
and salts or solvates thereof.

Kits comprising MS active, fluorescence tagging compounds can contain a phenyl derivative of Formula XA:

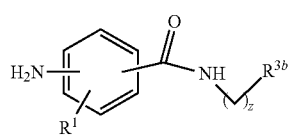

Formula XA wherein R$_1$ is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, N$_3$, SH, SCH$_3$, C(O)CH$_3$, CO$_2$CH$_3$ and CO$_2$H;
R$^{3b}$ is

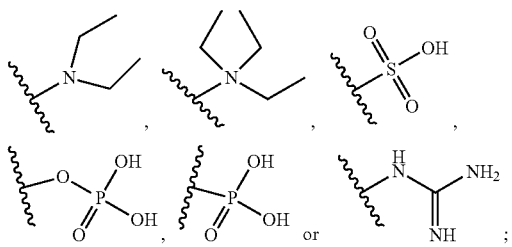

z=1-12;
and salts or solvates thereof.

Kits comprising MS active, fluorescence tagging compounds can contain a phenyl derivative of Formula XB:

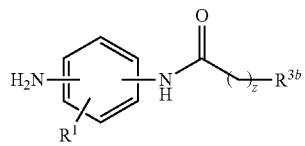

Formula XB wherein R$_1$ is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, N$_3$, SH, SCH$_3$, C(O)CH$_3$, CO$_2$CH$_3$ and CO$_2$H;
R$^{3b}$ is

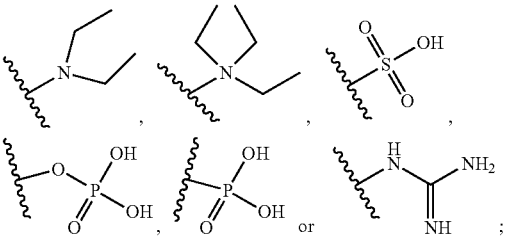

z=1-12;
and salts or solvates thereof.

Kits comprising MS active, fluorescence tagging compounds can contain a phenyl derivative of Formula XC:

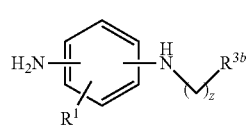

Formula XC wherein R$_1$ is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, N$_3$, SH, SCH$_3$, C(O)CH$_3$, CO$_2$CH$_3$ and CO$_2$H;
R$^{3b}$ is

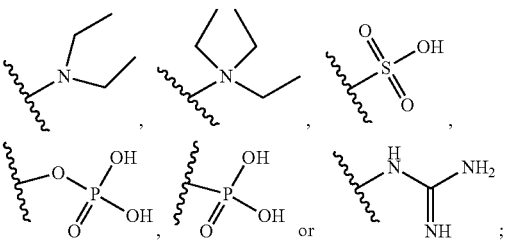

z=1-12;
and salts or solvates thereof.

Kits comprising MS active, fluorescence tagging compounds can contain a phenyl derivative of Formula XD:

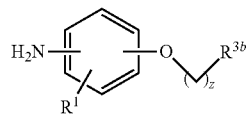

Formula XD wherein R$_1$ is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

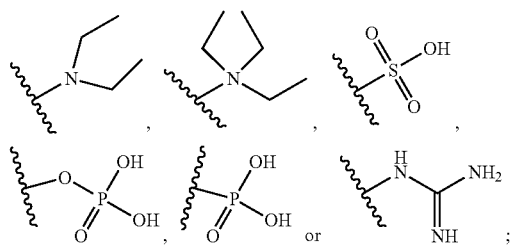

z=1-12;
and salts or solvates thereof.

Kits comprising MS active, fluorescence tagging compounds can contain a phenyl derivative of Formula XE:

Formula XE

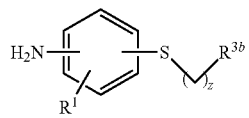

wherein $R_1$ is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

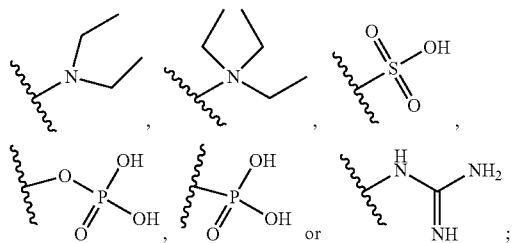

z=1-12;
and salts or solvates thereof.

Kits comprising MS active, fluorescence tagging compounds can contain a phenyl derivative of Formula XF:

Formula XF

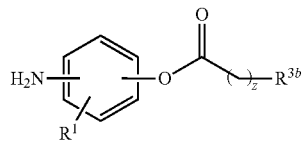

wherein $R_1$ is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl sulfonate, sulfonic acid, $N_3$, SH, $SCH_3$, $C(O)CH_3$, $CO_2CH_3$ and $CO_2H$;
$R^{3b}$ is

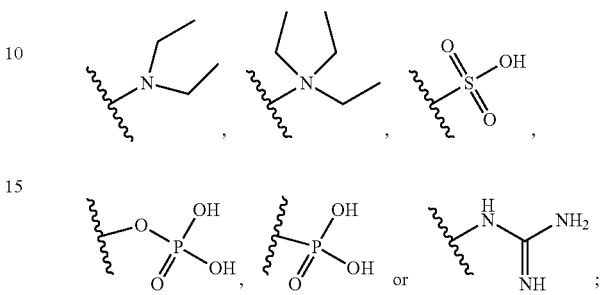

z=1-12;
and salts or solvates thereof.

Kits comprising MS active, fluorescence tagging compounds can contain a phenyl derivative of Formula XG:

Formula XG

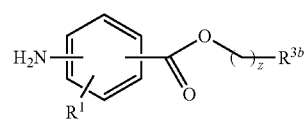

wherein $R_1$ is selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$; $R^{3b}$ is

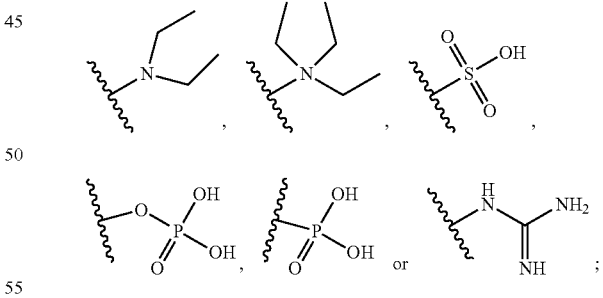

z=1-12;
and salts or solvates thereof.

In addition, provided below are kits containing exemplary compounds (Table E) of the structural Formulas X, XA, XB, XC, XD, XE, XF or XG which can be useful for fluorescent labeling of glycans and subsequent analysis by means of liquid chromatography and mass spectrometry. The compounds of structural formulas X, XA, XB, XC, XD, XE, XF or XG can be optionally substituted with any group that does not substantially reduce the fluorescence of the compound.

TABLE E
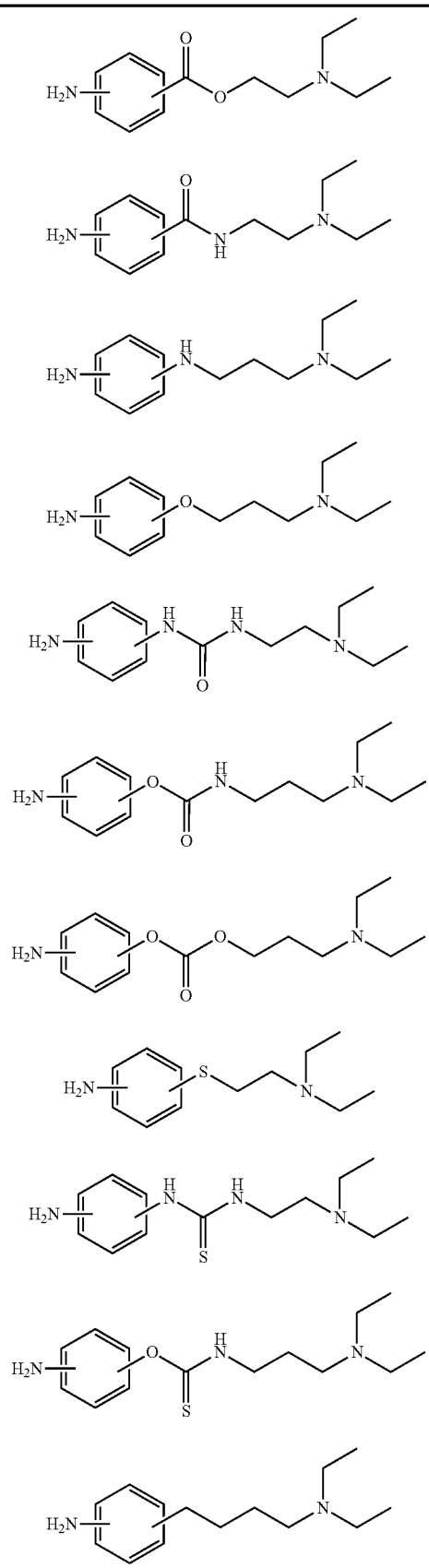
TABLE E-continued
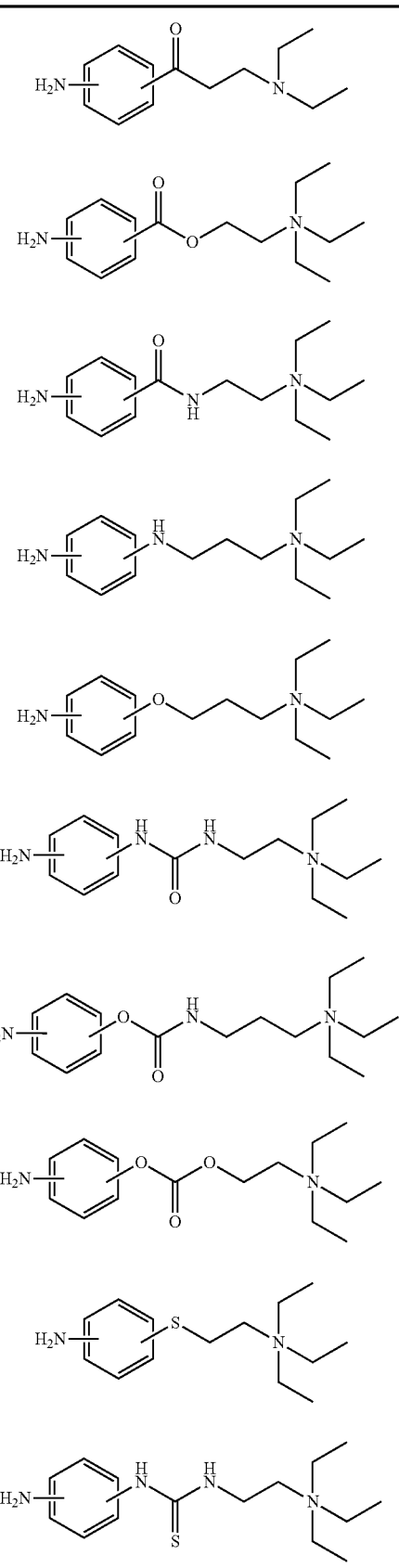

TABLE E-continued

TABLE E-continued
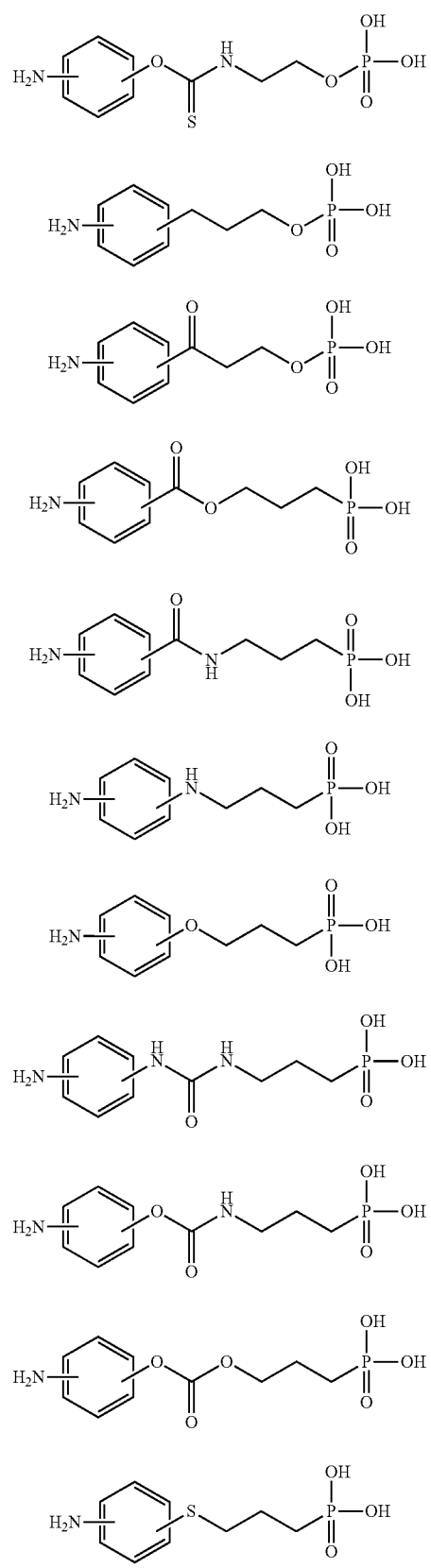
TABLE E-continued
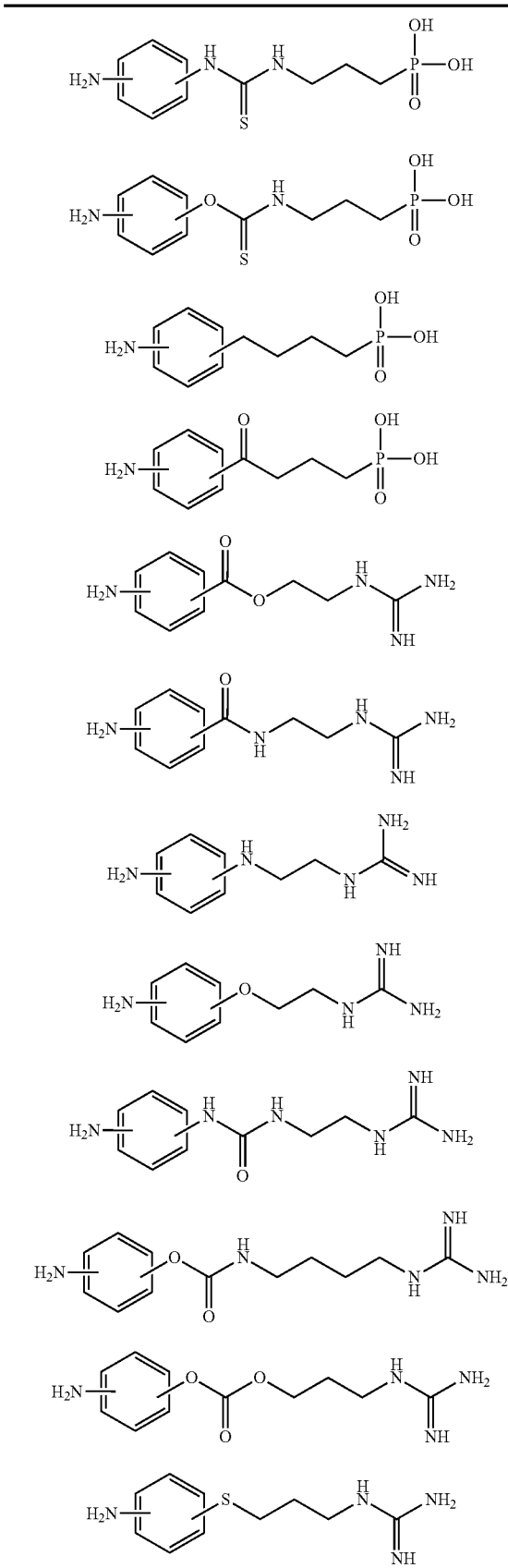

TABLE E-continued

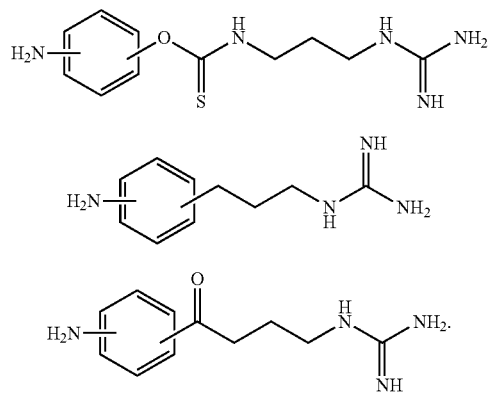

Methods for tagging, derivatizing or conjugating glycans and other biomolecules containing at least one ketone group or an aldehyde group with a compound of Formula XIV, XIVA, XIVB, XIVC, XIVD, XIVE, XIVF or XIVG by reductive amination reaction are provided. The reaction between the compound of Formula X and an aldehyde containing biomolecule, such as a glycan can be conducted under conditions that facilitate reductive amination in the presence of a reducing agent, such as sodium cyanoborohydride or sodium triacetoxyborohydride. The reaction can be carried out in a solution or suspension of a compound of Formula X, XA, XB, XC, XD, XE, XF or XG in an acidic media, for example in citric acid or acetic acid, and mixing with a solution or suspension of a reducing agent such as cyanoborohydride or sodium triacetoxyborohydride in an organic solvent, for example, tetrohydrofuran or dimethylsulfoxide.

Methods for analyzing glycans and other biomolecules containing an aldehyde group in a sample containing at least one biomolecule, such as a glycan, by means of liquid chromatography and mass spectrometry. These analytical methods include the step of labeling the biomolecule, such as a glycan, in the sample by reacting with a compound of Formula X, XA, XB, XC, XD, XE, XF or XG for a time and under conditions suitable to facilitate the labeling through reductive amination; and subjecting the labeled conjugate to liquid chromatography and mass spectrometry.

As provided herein, glycans can be conjugated to MS active fluorescent compounds of Formula X and salts or solvates thereof. The following schematic shows the tagging of a glycan using a compound of Formula X through reductive amination:

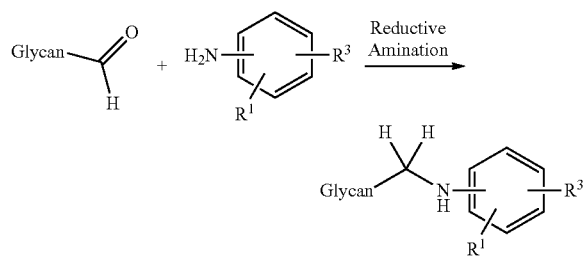

wherein FL $R^1$, $R^2$ and $R^3$ are as described above.

Methods of labeling the glycans with MS active fluorescent compounds of Formula X, as well as conjugates resulting therefrom are provided.

The following Scheme I and Scheme II can be used to make the compounds described herein.

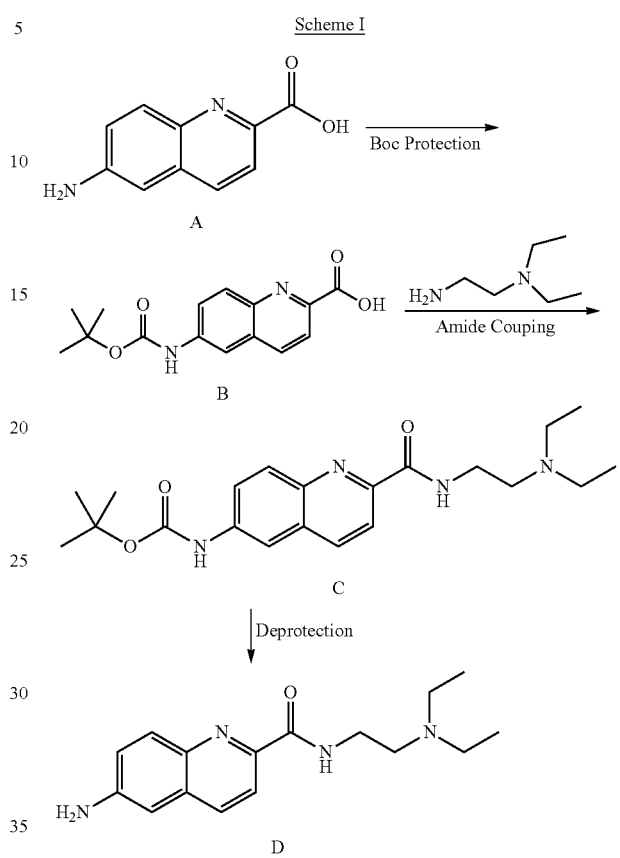

Preparation of 6-amino-N-[2-(diethylamino)ethyl]-2-quinolinecarboxamide (D)

40 mg of B was dissolved in 2.5 mL of a 1:4 mixture of dimethylformamide:dichloromethane in a 10 mL flask equipped with a stir bar and purged with $N_2$. 1.7 mg of dimethylaminopyridine and 181 µL of dicyclohexylcarbodiimide were then added to the flask. After stirring for 10 min, 2-(diethylamino)ethylamine (57 mg) in 3 mL of dichloromethane was added to the flask. This was then stirred at room temperature for 20 hours. After this time, 3 mL of water was added to the reaction flask. The organic layer was separated and the aqueous layer was extracted with 2 mL of dichloromethane. The organic phases were combined, dried, and then evaporated to dryness to provide the crude material. This was subjected to standard organic chemistry purification techniques to provide the desired material C in >95% purity.

1.8 g of C was dissolved in a mixture of 5.3 g of trifluoracetic acid in 30 mL of dichloromethane. The reaction mixture was stirred at room temperature for 48 hours. After removal of the solvent under reduced pressure, the crude material was dissolved in 30 mL of 0.5 N HCl. This mixture was then extracted with 50 mL aliquots of ethyl acetate. The organic phases were combined, dried, and then evaporated to dryness to yield 1.2 gram of the crude product. This was subjected to standard organic chemistry purification techniques to provide the desired material D in >98% purity.

Scheme II

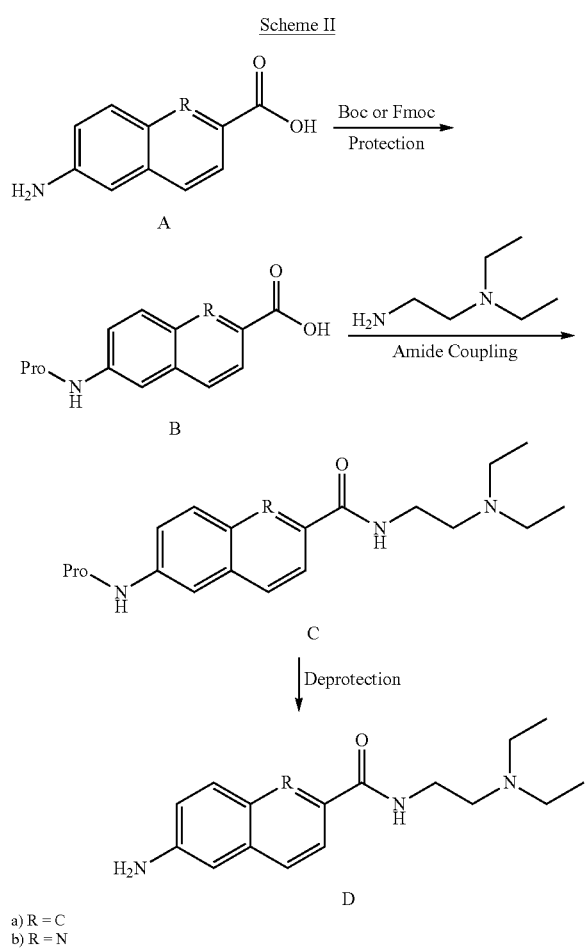

a) R = C
b) R = N

The method used for Scheme I is applicable to Scheme II for making the compounds presented herein.

Other Derivatization Methods

A number of alternative derivatization procedures have been developed to permit the assay of glycans by high performance liquid chromatographic and electrophoretic separations. Under certain conditions, the compounds presented herein can be subject to rapid tagging processes where reagent solution is added to released glycans at room temperature for four or five minutes, and then lyophilized and subsequently reconstituted in acetonitrile/water solution. Other possible derivatization methods that might be utilized to tag glycans with the reagents described herein include:

(1) The o-phthalaldehyde ("OPA")/mercaptan method. The OPA procedure can detect amino acids with a typical detectable level in the order of about 100 femtomole (fmol). Here, an adduct can be unstable and, therefore, should be prepared shortly before the detection step. Also, the reagent may not form a derivative with secondary amino acids.

(2) The 9-fluorenylmethylchloroformate ("FMOC") method. The FMOC procedure provides for stable derivatives having a minimum detectable level in the order of a few hundred fmol. Free tryptophan and cystine are sometimes difficult to quantitate. The derivatizing reagent is preferably removed from the reaction mixture by an extraction step because it is itself fluorescent. The reagent has also been reported to form multiple derivatives with histidine. The reagent can be hazardous to work with, because it is corrosive and is a lachrymator.

(3) The phenylisothiocyanate ("PITC") method. The PITC procedure yields stable derivatives which are formed rapidly. It can be used for both primary and secondary amino acids, as well as cystine. The method uses absorbance as the detection procedure, and can provide a minimum detection limit of 1 pmol. However, the derivatives are not fluorescent and detection must be performed at 254 nm, which does not allow for good detection selectivity.

(4) The dansyl chloride method. The dansyl chloride method provides stable derivatives with a minimum detectability in the order of about 1.5 pmol. It is able to detect secondary amines and cysteine, but it results in multiple derivatives.

(5) Fluorescent succinimidocarbamates are useful as derivatizing agents for amines, amino acids, peptides, phosphates and other classes of compounds. When the succinimidocarbamate reagent is used to tag a compound with a fluorescent group, a detection limit of about 1 pmol can be achieved. These reagents can be used in conjunction with modern separation techniques such as high performance liquid chromatography, thin layer chromatography or capillary electrophoresis.

Detection of Derivatized Glycans by MS and Fluorescence

Most amino acids and/or glycans are not readily detectable in the absence of a strong chromophore or fluorophore or MS active moiety. The absorbance and fluorescence response are quite weak. One tactic used to maximize the sensitivity of an assay is to convert the compound of interest into a derivative that exhibits a better response for the detection method being utilized. The selection of a derivatizing agent is an important choice in the development of an analytical procedure. The derivatizing agent affects the ultimate sensitivity and accuracy of the analysis by maximizing the sensitivity, yield and stability of the derivatized molecules.

Basically, the following determinations can be performed separately: (1) the glycosylated sites; (2) the glycosylated site occupancy; (3) the structure and amount of each glycan at each site: and (4) the number of glycoforms. Harvey, D. J., Identification of Protein-Bound Carbohydrates by Mass Spectrometry, 1 PROTEOMICS 311-319 (2001) at 312, incorporated herein by reference. In most situations, MS can provide the answers to each of these steps. Hence the need for enhanced MS signals. Because of the branched nature of the glycan, however, structural determination of the glycan is complicated. Here, the monosaccharide unit, the anomericity and ring size of each monosaccharide, the monosaccharide sequence and ring conformation together with identification of other groups must be determined. With the exception of ring conformation, MS can be used directly or indirectly to make these determinations using MALDI and/or ESI as the preferred MS technique. Id. at 313-316, incorporated herein by reference.

Compounds described herein are useful for derivatizing glycans because they can form stable, highly fluorescent MS derivative compounds and conjugate glycans. The general methodology for an analysis of a glycan or amino acid derivatized by these compounds include three closely related processes: (1) formation of derivatives in the sample; (2) separation of the derivatives; and (3) detection of the separated derivatives. The first step is generally performed by reacting a mixture with one of the present compounds as a reagent to yield a derivatized compound. The derivatives provide a fluorescent signal which can then be detected in the detection stage of the analysis.

The separation step is based upon the differences in the chemical structure of the derivatives. The derivatized compounds can differ from each other in the same way that the chemical structures of the precursor compounds differ. The derivatives must be separated so that the detector signal can be correctly related to the concentration of each derivative. The derivatized glycans can be separated and detected by chromatography, e.g., by high performance liquid chromatography ("HPLC") or capillary zone electrophoresis ("CZE").

The detection step is generally carried out using either an absorbance or fluorescence detector. As each derivative is eluted from the chromatographic column after separation, its presence and quantity is detected by a mass spectrometer and/or by the aborbance or emission of light. The sensitivity of the assay depends upon the strength of the signal produced.

Analytical methods of analyzing glycans have become considerably sophisticated. Exemplary analytical instrumentation includes CE-, HPAEC-PAD, HILIC-LC/FLR, RPLC/MS, and MALDI-MS. Liquid chromatography ("LC") separation with fluorescence detection is widely used in the pharmaceutical industry for the characterization of enzymatically/chemically released glycan, typically tagged with a fluorescent dye at the reducing end of a glycan. Kalyan R. Anumula & Shirish T. Dhume, *High Resolution and High Sensitivity Methods for Oligosaccharide Mapping and Characterization by Normal Phase High Performance Liquid Chromatography Following Derivatization with Highly Fluorescent Anthranilic Acid,* 8 GLYCOBIOLOGY 685 (1998); Karina Mariño et al., *A Systematic Approach to Protein Glycosylation Analysis: A Path Through the Maze,* 6 NATURE CHEMICAL BIOLOGY 713 (2010).

Fluorescent measurements are sensitive and quantitative; the low detection limit is in the low femtomoles. With recent advancements in mass spectrometry instrumentation, the combination of liquid chromatography, fluorescence and MS has gained more popularity as an analytical instrument platform for routine characterization of fluorescently labeled N-linked glycans. Therefore, relative quantitation and molecular weight measurements can be done in a single analysis. Shigeo Suzuki et al., *Comparison of the Sensitivities of Various Derivatives of Oligosaccharides in LC/MS with Fast Atom Bombardment and Electrospray Ionization Interfaces,* 1006 ANAL CHEM 2073 (1996). However, a challenge has been that glycans do not ionize efficiently via electro-spray-ionization ("ESI").

Additional Uses for the Compounds Presented Herein

Absorbance detection is generally used in protein mapping work. Two different detection processes which are often used for this purpose are: a) detection at 210-215 nm using a single wavelength detector; and b) broadband spectral detection using a photodiode array (PDA) detector. In the first method, all peptides absorb at that wavelength, thus the user can ensure that all peptides eluted from the column are detected. One difficulty with this technique is that a wide variety of compounds absorb in this region of the spectrum, and extreme care must be taken to ensure that all reagents, eluents, glassware, etc. are scrupulously clean to ensure that the observed signal is solely from the peptides. In the second method, the PDA detector collects the spectra of the eluent at specific time intervals (e.g. a spectrum between 200 and 350 nm is collected every second). This provides more information than a single wavelength and thus can assist in distinguishing between peptides which can elute with similar retention times.

Sample Preparation

To obtain high quality mass spectra, the condition of the sample is important. Compounds other than analyte will generally have an adverse effect on ion yield and are preferably removed. Indeed, while small amounts of sodium are essential for ionization by MALDI, carbohydrates are particularly susceptible to the effects of salts. Moreover, many carbohydrates occur as mixtures. Therefore, it is important to ensure that isolation and purification techniques do not cause fractionation of the sample with a loss of quantitative information.

We claim:

1. A compound of Formula II or a salt or solvate thereof;

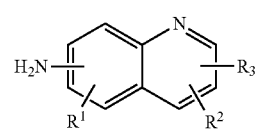

Formula II wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^3$ is

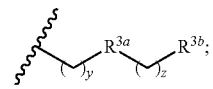

$R^{3a}$ is selected from ester, amide, amine, oxygen, urea, carbamate, carbonate, sulfur, thiourea, thiocarbamate, alkyl or carbonyl;

$R^{3b}$ is

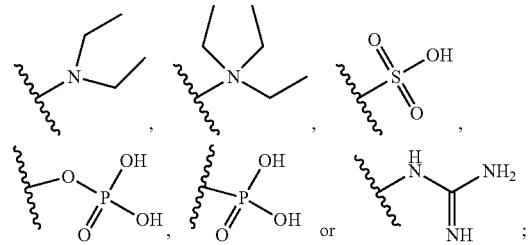

y=0–12;

z=1–12;

and salts or solvates thereof;

with the proviso that said compound of Formula II is other than 6-amino-N-[2-(diethylamino)ethyl]-2-quinolinecarboxamide;

with the proviso that when y is one, $R^{3a}$ is other than amide;

with the proviso that when y is zero, $R^{3a}$ is amine, oxygen or sulfur and z is two, $R^{3b}$ is other than

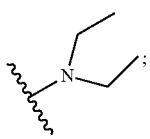 [SMILES: *N(CC)CC]

with the proviso that when y is zero, $R^{3a}$ is amine, and z is three, $R^{3b}$ is other than

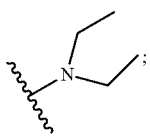

and with the proviso that when y is one, $R^{3a}$ is amide, and z is two or three, $R^{3b}$ is other than

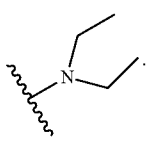 [SMILES: *N(CC)CC]

2. A compound having the formula:

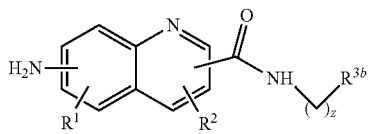

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

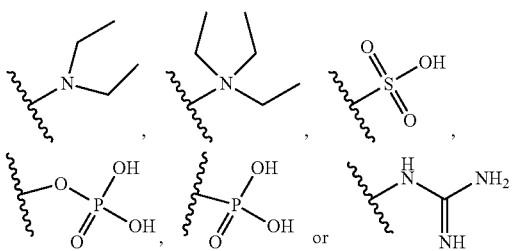

z=1-12;

and salts or solvates thereof;

with the proviso that said compound is other than 6-amino-N-[2-(diethylamino)ethyl]-2-quinolinecarboxamide.

3. A compound having the formula:

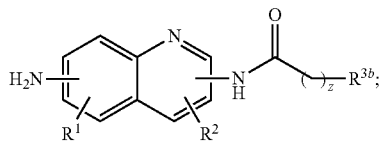

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

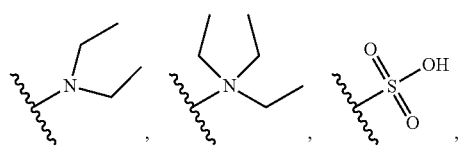

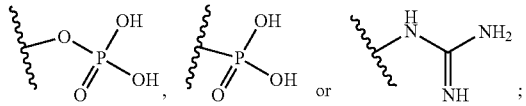

z=1-12;

and salts or solvates thereof.

4. A compound of claim 1 having the formula:

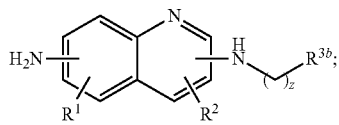

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

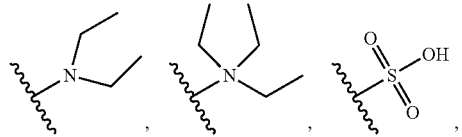

-continued

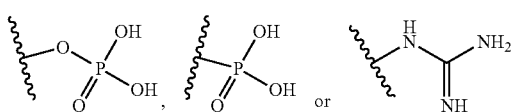

z=1–12;
and salts or solvates thereof;
with the proviso that when z is two or three, $R^{3b}$ is other than

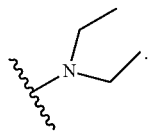 [SMILES: *N(CC)CC]

5. A compound according to claim 1 having the formula:

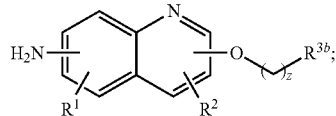

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

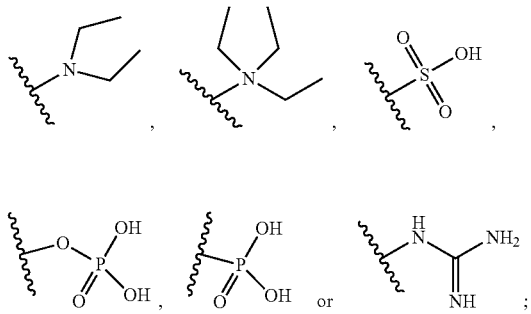

z=1–12;
and salts or solvates thereof;
with the proviso that when z is two, $R^{3b}$ is other than

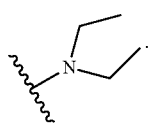 [SMILES: *N(CC)CC]

6. A compound according to claim 1 having the formula:

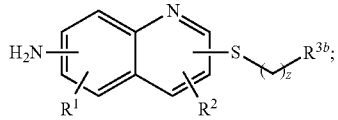

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

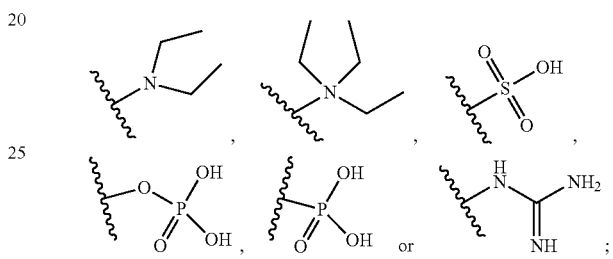

z=1–12;
and salts or solvates thereof;
with the proviso that when z is two, $R^{3b}$ is other than

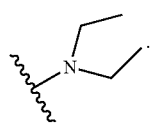

7. A compound having the formula:

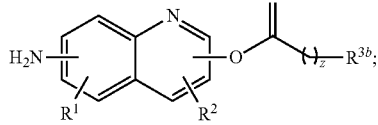

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;
$R^{3b}$ is

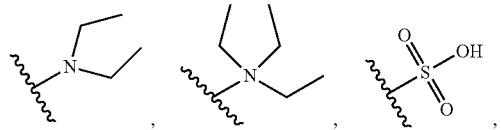

-continued

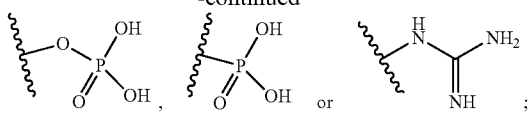

z=1–12;
and salts or solvates thereof.

8. A compound having the formula:

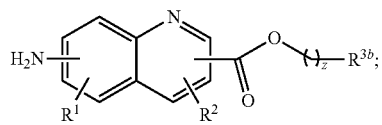

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

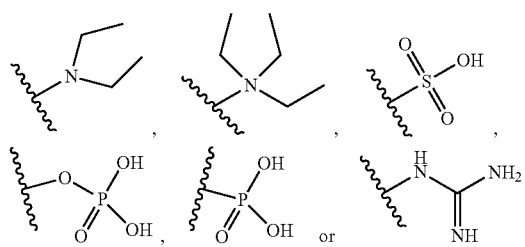

z=1–12;
and salts or solvates thereof.

9. A compound according to claim 1 wherein $R^1$ is hydrogen.

10. A compound according to claim 1 wherein $R^2$ is hydrogen.

11. A compound of Formula II or a salt or solvate thereof;

Formula II

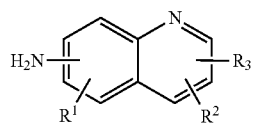

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^3$ is

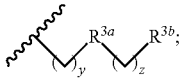

$R^{3a}$ is selected from ester, amide, amine, oxygen, urea, carbamate, carbonate, sulfur, thiourea, thiocarbamate, alkyl or carbonyl;

$R^{3b}$ is

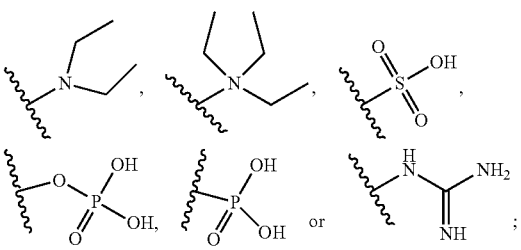

y=0–12;
z=1–12;
and salts or solvates thereof;
with the proviso that said compound of Formula II is other than 6-amino-N-[2-(diethylamino)ethyl]-2-quinolinecarboxamide;
with the proviso that when y is one, $R^{3a}$ is other than amide;
with the proviso that when y is zero, $R^{3a}$ is amine, oxygen or sulfur and z is two, $R^{3b}$ is other than

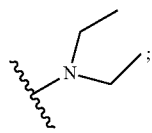 [SMILES: *N(CC)CC]

with the proviso that when y is zero, $R^{3a}$ is amine, $R^{3b}$ is other than

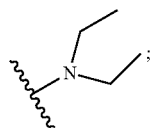 [SMILES: *N(CC)CC]

and
with the proviso that when y is one, $R^{3a}$ is amide, and z is two or three, $R^{3b}$ is other than

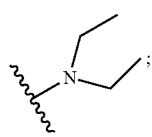 [SMILES: *N(CC)CC]

and one or more of the following:
a deglycosylation module comprising endoglycosidase and one or more surfactants;

one or more compounds that can chemically cleave a glycoprotein;

a separation device; and a buffer.

12. The analytical kit according to claim 11 wherein said compound of Formula II is selected from Formula IIA, Formula IIB, Formula IIC, Formula IIC, Formula IID, Formula IIE, Formula IIF or Formula IIG:

Formula IIA

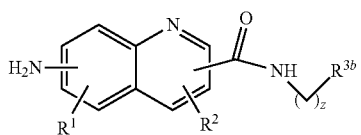

Formula IIB

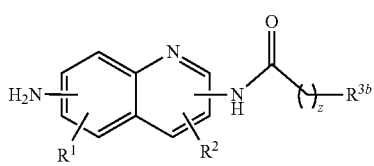

Formula IIC

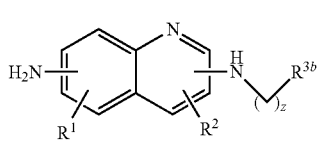

Formula IID

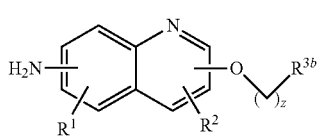

Formula IIE

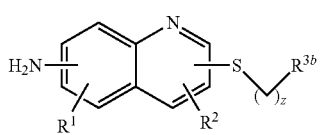

Formula IIF

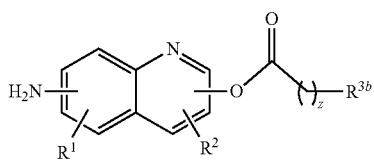

Formula IIG

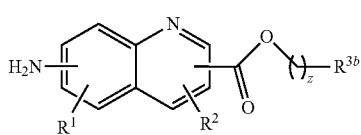

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^{3b}$ is

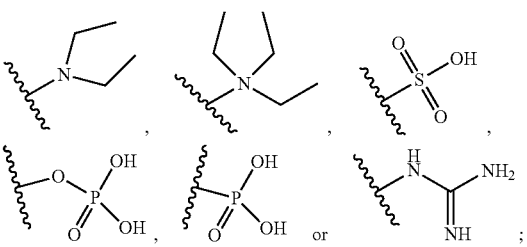

z=1-12;

and salts or solvates thereof.

13. The analytical kit of claim 12 wherein said compound of Formula IIA is:

[structure]

and salts or solvates thereof.

14. A conjugate of a compound of Formula II and a glycan depicted below:

[structure]

wherein each $R_1$ and $R_2$ is independently selected from hydrogen, halogen, lower alkyl, lower alkenyl, lower alkynyl, lower alkanoyl, lower haloalkyl, lower haloalkenyl, lower haloalkynyl, lower cycloalkyl, lower acyloxy, hydroxy, amino, lower alkylamino, amido, nitro, lower alkylthio, lower alkylsulfinyl, lower alkylsulfonyl, sulfonate, sulfonic acid, $N_3$, SH, $SCH_3$, $C(O)CH_3$, $CO_2CH_3$ and $CO_2H$;

$R^3$ is

[structure]

$R^{3a}$ is selected from ester, amide, amine, oxygen, urea, carbamate, carbonate, sulfur, thiourea, thiocarbamate, alkyl or carbonyl;

$R^{3b}$ is

[structure]

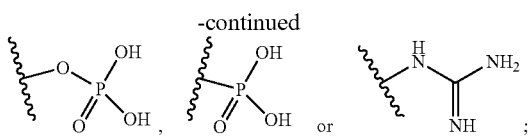

y=0-12;
z=1-12;
and salts or solvates thereof.

15. The conjugate according to claim 14 wherein said compound of Formula II is:

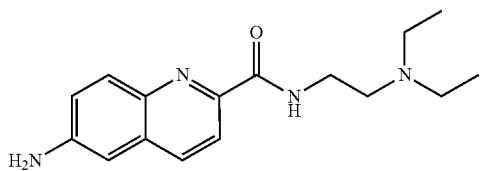 [SMILES: CCN(CC)CCNC(=O)c1ccc2cc(N)ccc2n1]

and salts and solvates thereof.

16. The conjugate of claim 14 wherein said glycan is selected from A2, FA2, M5, FA1G1, A2G1, FA2G1, FA2G2, FA2G1Ga1, FA2G2Ga1, FA2G2Sg1, FA2G1Ga2, FA2G2GaSg1, mannobiose (Man2), mannotriose (Man3), mannotetraose (Man4), mannopentaose (Man5), mannohexaose (Man6) and mannoheptaose (Man7).

17. The kit of claim 11, comprising:
a deglycosylation module comprising endoglycosidase and one or more surfactants, and/or one or more compounds that can chemically cleave a glycoprotein.

18. The kit of claim 11, comprising:
a separation device; and/or
a buffer.

19. The kit of claim 11, comprising:
a deglycosylation module comprising endoglycosidase and one or more surfactants,
one or more compounds that can chemically cleave a glycoprotein,
a separation device, and
a buffer.

* * * * *